(12) United States Patent
DeHaan et al.

(10) Patent No.: US 10,806,871 B2
(45) Date of Patent: **\*Oct. 20, 2020**

(54) INHALABLE DRY POWDERS

(71) Applicant: Pulmatrix Operating Company, Inc., Lexington, MA (US)

(72) Inventors: Wesley H. DeHaan, Chelmsford, MA (US); Jean C. Sung, Cambridge, MA (US); Diana Manzanedo, Cambridge, MA (US); Ciaran Lawlor, Cambridge, MA (US); Michael Tauber, Allston, MA (US)

(73) Assignee: Pulmatrix Operating Company, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,841

(22) Filed: Jan. 27, 2020

(65) Prior Publication Data

US 2020/0261667 A1 Aug. 20, 2020

Related U.S. Application Data

(60) Continuation of application No. 15/495,450, filed on Apr. 24, 2017, now Pat. No. 10,589,039, which is a (Continued)

(51) Int. Cl.
*A61M 15/00* (2006.01)
*A61K 9/16* (2006.01)
(Continued)

(52) U.S. Cl.
CPC ....... *A61M 15/0001* (2014.02); *A61K 9/0075* (2013.01); *A61K 9/1611* (2013.01);
(Continued)

(58) Field of Classification Search
None
See application file for complete search history.

(56) References Cited

U.S. PATENT DOCUMENTS 4,233,405 A 11/1980 Neubeck
4,637,815 A 1/1987 Lemole
(Continued)

FOREIGN PATENT DOCUMENTS

CN 1240349 1/2000
CN 1422154 A 6/2003
(Continued)

OTHER PUBLICATIONS

Ghoroi et al., "Dispersion of fine and ultrafine powders through surface modification and rapid expansion," Chemical Engineering Science, vol. 85, Jan. 14, 2013, pp. 11-24.
(Continued)

*Primary Examiner* — Kyung S Chang
(74) *Attorney, Agent, or Firm* — Hogan Lovells US LLP

(57) ABSTRACT

The invention related to dry powders that contain a therapeutic agent. The dry powders have characteristics, e.g., they are processable and/or dense in therapeutic agent that provide advantages for formulating and delivering therapeutic agents to patients.

14 Claims, 9 Drawing Sheets

Related U.S. Application Data division of application No. 14/378,453, filed as application No. PCT/US2013/028261 on Feb. 28, 2013, now abandoned.

(60) Provisional application No. 61/605,083, filed on Feb. 29, 2012, provisional application No. 61/607,928, filed on Mar. 7, 2012, provisional application No. 61/645,927, filed on May 11, 2012, provisional application No. 61/648,506, filed on May 17, 2012, provisional application No. 61/707,071, filed on Sep. 28, 2012.

(51) Int. Cl.
*A61K 9/00* (2006.01)
*A61K 31/137* (2006.01)
*A61K 31/69* (2006.01)
*A61K 31/5383* (2006.01)
*A61K 31/56* (2006.01)
*A61K 31/46* (2006.01)

(52) U.S. Cl.
CPC .......... *A61K 9/1617* (2013.01); *A61K 31/137* (2013.01); *A61K 31/46* (2013.01); *A61K 31/5383* (2013.01); *A61K 31/56* (2013.01); *A61K 31/69* (2013.01); *A61M 15/0045* (2013.01); *A61M 15/0065* (2013.01); *A61M 15/0091* (2013.01); *A61M 2202/064* (2013.01)

(56) References Cited

U.S. PATENT DOCUMENTS

| | | |
|---|---|---|
| 4,828,844 A | 5/1989 | Rontgen-Odenthal et al. |
| 5,175,152 A | 12/1992 | Singh |
| 5,230,884 A | 7/1993 | Evans et al. |
| 5,466,680 A | 11/1995 | Rudy |
| 5,571,535 A | 11/1996 | Flowers et al. |
| 5,612,053 A | 3/1997 | Baichwal et al. |
| 5,633,003 A | 5/1997 | Cantor |
| 5,654,007 A | 8/1997 | Johnson et al. |
| 5,709,202 A | 1/1998 | Lloyd |
| 5,785,049 A | 7/1998 | Smith et al. |
| 5,817,028 A | 10/1998 | Anderson |
| 5,855,913 A | 1/1999 | Hanes et al. |
| 5,883,084 A | 3/1999 | Peterson et al. |
| 5,898,037 A | 4/1999 | Marx |
| 5,981,559 A | 11/1999 | Nagaoka et al. |
| 5,985,309 A | 11/1999 | Edwards et al. |
| 6,083,922 A | 7/2000 | Montgomery |
| 6,165,463 A | 12/2000 | Platz et al. |
| RE37,053 E | 2/2001 | Hanes et al. |
| 6,214,536 B1 | 4/2001 | Boucher |
| 6,254,854 B1 | 7/2001 | Edwards et al. |
| 6,447,752 B2 | 9/2002 | Edwards et al. |
| 6,451,352 B1 | 9/2002 | Yvin et al. |
| 6,475,523 B1 | 11/2002 | Staniforth |
| 6,572,849 B2 | 6/2003 | Shahinian, Jr. |
| 6,582,728 B1 | 6/2003 | Platz et al. |
| 6,635,283 B2 | 10/2003 | Edwards et al. |
| 6,669,959 B1 | 12/2003 | Adjei et al. |
| 6,732,732 B2 | 5/2004 | Edwards et al. |
| 6,749,835 B1 | 6/2004 | Lipp et al. |
| 6,830,764 B2 | 12/2004 | Inui et al. |
| 7,008,644 B2 | 3/2006 | Batycky et al. |
| 7,112,572 B2 | 9/2006 | Deadman et al. |
| 7,182,961 B2 | 2/2007 | Batycky et al. |
| 7,192,919 B2 | 3/2007 | Tzannis et al. |
| 7,306,787 B2 | 12/2007 | Tarara et al. |
| 7,384,649 B2 | 6/2008 | Batycky et al. |
| 7,556,798 B2 | 7/2009 | Edwards et al. |
| 7,575,761 B2 | 8/2009 | Bennett et al. |
| 7,838,532 B2 | 11/2010 | Surber et al. |
| 7,879,358 B2 | 2/2011 | Jackson et al. |
| 8,187,637 B2 | 5/2012 | Edwards et al. |
| 8,591,866 B2 | 11/2013 | Edwards et al. |
| 2001/0008632 A1 | 7/2001 | Freund et al. |
| 2001/0038858 A1 | 11/2001 | Roser et al. |
| 2002/0034477 A1 | 3/2002 | Edwards et al. |
| 2002/0177562 A1 | 11/2002 | Weickert et al. |
| 2003/0055034 A1 | 3/2003 | Montgomery |
| 2003/0129139 A1 | 7/2003 | Batycky et al. |
| 2003/0138403 A1 | 7/2003 | Drustrup |
| 2003/0186894 A1 | 10/2003 | Kuo et al. |
| 2003/0232019 A1 | 12/2003 | Basu et al. |
| 2004/0009128 A1 | 1/2004 | Rabinowitz et al. |
| 2004/0047810 A1 | 3/2004 | Staniforth et al. |
| 2004/0105821 A1 | 6/2004 | Bernstein et al. |
| 2005/0004020 A1 | 1/2005 | Yu et al. |
| 2005/0054682 A1 | 3/2005 | Phillips |
| 2005/0123509 A1 | 6/2005 | Lehrman et al. |
| 2005/0211244 A1 | 9/2005 | Nilsson et al. |
| 2005/0220720 A1 | 10/2005 | Edwards et al. |
| 2005/0255049 A1 | 11/2005 | Slowey et al. |
| 2005/0276845 A1 | 12/2005 | Roser et al. |
| 2005/0281740 A1 | 12/2005 | Gong et al. |
| 2006/0073173 A1 | 4/2006 | Banach et al. |
| 2006/0142208 A1 | 6/2006 | Boucher |
| 2006/0147520 A1 | 7/2006 | Ruegg |
| 2006/0276483 A1 | 12/2006 | Surber et al. |
| 2007/0053844 A1 | 3/2007 | Watanabe et al. |
| 2007/0092535 A1 | 4/2007 | Watts |
| 2007/0104657 A1 | 5/2007 | Batycky et al. |
| 2007/0202051 A1 | 8/2007 | Schuschnig |
| 2007/0270502 A1 | 11/2007 | Edwards et al. |
| 2007/0275091 A1 | 11/2007 | King et al. |
| 2007/0292454 A1 | 12/2007 | Bell et al. |
| 2008/0038207 A1 | 2/2008 | Edwards et al. |
| 2008/0063722 A1 | 3/2008 | Ward et al. |
| 2008/0127972 A1 | 6/2008 | Morton |
| 2008/0152764 A1 | 6/2008 | Kremer et al. |
| 2008/0190424 A1 | 8/2008 | Lucking et al. |
| 2009/0208999 A1 | 8/2009 | Groenendaal et al. |
| 2009/0232744 A1 | 9/2009 | Keller et al. |
| 2010/0159007 A1 | 6/2010 | Staniforth |
| 2010/0285142 A1 | 11/2010 | Staniforth et al. |
| 2011/0192397 A1 | 8/2011 | Saskar et al. |
| 2011/0236492 A1 | 9/2011 | Morton |
| 2012/0070417 A1 | 3/2012 | Batycky |
| 2012/0107414 A1 | 5/2012 | Lipp |
| 2013/0004542 A1 | 1/2013 | Martyn |

FOREIGN PATENT DOCUMENTS

| | | |
|---|---|---|
| CN | 1446877 | 10/2003 |
| CN | 101237853 | 3/2007 |
| CN | 101106975 | 1/2008 |
| EP | 0367723 | 5/1990 |
| EP | 0652011 | 5/1995 |
| EP | 0681833 | 11/1995 |
| EP | 1466610 | 10/2004 |
| JP | 05123398 | 5/1993 |
| JP | 2004-503482 | 2/2004 |
| JP | 2004-532217 | 10/2004 |
| JP | 2005511628 A | 4/2005 |
| JP | 2007506500 | 3/2007 |
| KR | 1020050056622 | 6/2005 |
| NZ | 328476 | 5/1999 |
| NZ | 305168 | 8/1999 |
| NZ | 530123 | 1/2007 |
| WO | 199206695 | 4/1992 |
| WO | 199612470 | 5/1996 |
| WO | 96/31221 | 10/1996 |
| WO | 199736574 | 10/1997 |
| WO | 199744013 | 11/1997 |
| WO | 98/16205 | 4/1998 |
| WO | 199951096 | 10/1999 |
| WO | 199964014 | 12/1999 |
| WO | 200013677 | 3/2000 |
| WO | 200086206 | 11/2000 |
| WO | 01/13892 | 3/2001 |
| WO | 2001/13892 | 3/2001 |
| WO | 2001/76610 | 10/2001 |

(56) References Cited

FOREIGN PATENT DOCUMENTS

| WO | 200185136 | 11/2001 | | |
|---|---|---|---|---|
| WO | 200185137 | 11/2001 | | |
| WO | 01/95874 | 12/2001 | | |
| WO | 200195874 | 12/2001 | | |
| WO | 200209574 | 2/2002 | | |
| WO | 02/083079 | 10/2002 | | |
| WO | 03/043585 | 5/2003 | | |
| WO | 2003035028 | 5/2003 | | |
| WO | 2003/092654 | 11/2003 | | |
| WO | 2003103632 | 12/2003 | | |
| WO | 2004/002551 | 1/2004 | | |
| WO | WO2004/30659 A1 | 4/2004 | | |
| WO | 2004096204 | 11/2004 | | |
| WO | 2005004852 | 1/2005 | | |
| WO | 200541922 | 5/2005 | | |
| WO | 2005041921 | 5/2005 | | |
| WO | 2005092289 | 10/2005 | | |
| WO | WO2007/057714 | 5/2007 | | |
| WO | 2008025560 | 6/2008 | | |
| WO | 2006102438 | 9/2008 | | |
| WO | 2009/037503 | 3/2009 | | |
| WO | WO2009/140587 | 11/2009 | | |
| WO | 2010/111641 | 9/2010 | | |
| WO | 2010/111644 | 9/2010 | | |
| WO | 2010/111650 | 9/2010 | | |
| WO | 2010111640 | 9/2010 | | |
| WO | WO2010/111680 A2 | 9/2010 | | |
| WO | 2011048379 A1 | 4/2011 | | |
| WO | WO2011/048379 A2 | 4/2011 | | |
| WO | 2012/030645 | 3/2012 | | |
| WO | 2012030647 | 3/2012 | | |
| WO | 2012030864 | 3/2012 | | |
| WO | WO2012/030664 A1 | 3/2012 | | |
| WO | WO-2012044736 A1 * | 4/2012 | ......... | A61K 2300/00 |
| WO | WO2013/104892 | 7/2013 | | |

OTHER PUBLICATIONS

Kaye, et al., "Simultaneously Manufactured Nano-In-Micro(SIMANIM) Particles for Dry-Powder Modified-ReleaseDelivery of Antibodies," Pharmaceutics, Preformulations and Drug Delivery, 98:11:4055-4068, 2009.
Kilpatrick, et al., "Calcium Chloride and Adrenaline as Bronchial Dilators Compared by Sequential Analysis," British Medical Journal (1954), pp. 1388-1391.
King, "Rheology of cystic fibrosis sputum after in vitro treatment with hypertonic saline alone and in combination with recombinant human deoxyribonuclease I" Am. J. Respir. Crit. Care Med., 156(1):173-7 (1997).
King and Tarsitamo, "The effect of structured and unstructured pre-operative teaching: a replication", Nurs. Res., 31(6):324-9 (1982).
King, et al., "The role of mucus gel viscosity, spinnability, and adhesive properties in clearance by simulated cough", Biorheology, 26:737-745 (1989).
King, M., et al., "Mucomodulator Therapy in Cystic Fibrosis: Balancing Mucus Clearability Against the Spread of Airborne Pathogens," Pediatric Pulmonolgy, 2004, pp. 77-79, Supp. 26.
Kirkness, et al., "Decreased surface tension of upper airway mucosal lining liquid increases upper airway patency in anaesthetised rabbits", J. Physiol., 547(Pt 2):603-11(2003).
Kurashima, et al., "A pilot study of surfactant inhalation for the treatment of asthmatic attack" Arerugi, 40(2):160-3 (1991).
Lipp, et al., "Solving medical problems with chemical engineering", Chemtech, 42-57 (Mar. 1997).
Macosko, C.W. "Linear Viscoelasticity", in Rheology. Principles, Measurements, and Applications, Wiley-VCH, New York, pp. 109-133 1994).
Mai, X.-M, et al., "Hypertonic saline challenge tests in the diagnosis of bronchial hyperresponsiveness and asthma in children," Pediatric Allergy & Immunology, Oct. 2002, 13(5), pp. 361-3267.

Makker, et al., "Relation of hypertonic saline responsiveness of the airways to exercise induced asthma symptom severity and to histamine or methacholine reactivity," Thorax, 1993, 48, pp. 142-147.
Marriott, et al., "Changes in the Gel Properties of Tracheal Mucus Induced bu Divalent Cations," Biorheology, 1979, pp. 331-337, vol. 16.
The Merck Index, 12th edition, Merck &Co., Inc., Whitehouse Station, NJ, p. 1089, 1996, pp. 177 & 1614-1615.
Merck Manual Home Edition, "Asthma: Lung and Airway Disorders," accessed at www.merck.com/mmhe/print/sec04/ch044a/html accessed on May 5, 2010.
Merck Manual Home Edition, "Chronic Obstructive Pulmonary Disease," accessed at www.merck.com/mmhe/print/sec04/ch045a/html accessed on Mar. 21, 2010.
Merck Manual Home Edition, "Acute Respiratory Distress Syndrome (ARDS)," accessed on Nov. 17, 2011 at www.merckmanuals.com/home/lung_and_airway_disorders/respiratory_filure_and_acute_respiratory_distress_syndrome/acute_respiratory/distress_syndrome_ards.html#v727948.
The Online Merck Manual Medical Second Home Edition article, entitled, "Influenza"—accessed on Feb. 22, 2010 at www.merck.com/mmhe/print/sec17/ch198/ch198d.html.
Miller, M.J., "Assessing the use of Pharmacokinetic Models in Risk Assessments on Inhaled Toxicants", School of Public Health Sciences, Environmental Health, and Toxicology (1992). 6 parts.
Modler, "Calcium as an Adjuvant for Spray-Drying Acid Whey," Journal of Dairy Science, 61:294-299, 1978.
Morrison, F.A., "Introduction, How Much Do I Need to Learn about Rheology?" In Understanding Rheology, Oxford University Press, New York, pp. 1-11 (2001).
Mouro, D., et al. "Enhancement of Xcelodose Capsule-Filling Capabilities Using Roller Compaction," Pharmaceutical Technology, Feb. 2006.
Nanaumi, et al., "Properties of mixed monolayers of DPCC and viscoelasticity-giving substances", Colloids & Surfaces B: Bioinformatics, 17:167-174 (2000).
Nannini, L.J., et al., "Magnesium Sulfate as a Vehicle for Nebulized Salbutamol in Acute Asthma", Am. J. Med., 108:193-197 (2000).
Oneda, et al., "The Effect of Formulation Variables on the Dissolution and Physical Properties of Spray-Dried Microspheres Containing Organic Salts," Powder Technology, 130:377-384, 2003.
Takebayashi, et al., "Role of tachykinins in airway responses to ozone in rats" J Appl Physiol 85:442-450 (1998).
Papineni and Rosenthal, "The size distribution of droplets in the exhaled breath of healthy human subjects", J. Aerosol Med., 10(2):105-116 (1997).
Patton and Platz, "Pulmonary delivery of peptides and proteins for systemic action", Adv. Drug Del. Rev., 8:179-196 (1992).
Paul, Fundamental Immunology, Raven Press, New York, pp. 699-716, 1984.
Perry's Chemical Engineers' Handbook, 7th ed., 1997, pp. 2-10, 2-11, 2-120, 2-121.
Piret, et al., "Sodium lauryl sulfate, a microbicide effective against enveloped and nonenveloped viruses" Curr. Drug Targets. 3(1):17-30 (2002).
Rabbini, et al., "The Influence of formulation components on the aerosolisation properties of spray dried powders," J. of Controlled Release, 110:130-140, 2005.
Raynal, et al., "Calcium-dependent Protein Interactions in MUC5B Provide Reversible Cross-links in Salivary Mucus," The Journal of Biological Chemistry, Aug. 2003, pp. 28703-28710, vol. 278 (31).
Riedler, J., et al. "Inhaled hypertonic saline increases sputum expectoration in cystic fibrosis," J. Pediatr Child Health, 32:48-50 (1996).
Robinson, M., et al., "Effect of hypertonic saline amiloride, and cough on mucociliary clearance in patients with cystic fibrosis," Am J. Respir. Crit. Care Med., 153:1503-1509 (1996).
Robinson, M., et al., "Effect of increasing doses of hypertonic saline on mucociliary clearance in patients with cystic fibrosis," Thorax, 52:900-903 (1997).

(56) References Cited

OTHER PUBLICATIONS

Robinson, M., et al., The effect of inhaled mannitol on bronchial mucus clearance in cystic fibrosis patients: a pilot study, Eur. Respir. J., 14:678-685 (1999).
Rosenblum, E. E. ("fish." Grolier Multimedia Encyclopedia, 2006, Grolier Online, accessed Nov. 21, 2006 (gme.grolier.com/cgi-bin/article?assetid=0106750-0).
Rote Liste Service, "Rote Liste 2002" (2002), Editor Cantor Verlag, Frankfurt/Main, XP002416908, par. [72087], par. [28005].
Rudt and Muller, "In vitro Phagocytosis Assay of Nano- and Microparticles by chemiluminescence. I. Effect of Analytical Parameters, Particle Size and Particle Concentration", J. Controlled Release, 22:263-272 (1992).
Sanders, et al., "Cystic fibrosis sputum: a barrier to the transport of nanospheres", Am J Respir Crit Care Med., 162:1905-1911 (2000).
Sarrell, et al., "Nebulized 3% Hypertonic Saline Solution Treatment in Ambulatory Children with Viral Bronchiolitis Decreases Symptoms," Chest, 2002, 122, pp. 2015-2020.
Schelling G., et al., Biophyiscal Journal, 66:134-140 (1994).
Schurch, et al., "Surfactant displaces particles toward the epithelium in airways and alveoli", Respir Physiol., 80:17-32 (1990).
Serrano, P., et al., "New Data on Pharmacological Properties and Indications of Magnesium," In New Perspectives in Magnesium Research, Springher-Verglag, London, pp. 127-139 (2007).
Seville, et al., "Spray-Dried Powders for Pulmonary Drug Delivery," Crit. Rev. in Therapeutic Drug Carrier Systems, 24(4), 307-360, 2007.
Shigeta, et al. "Synergistic Anti-Influenza Virua A (H1N1) Activities of PM-523 (Polyoxometalate) and Ribavarin In Vitro and In Vivo," Antimicrobial Agents & Chemotherapy, 1997, 41, pp. 1423-1427.
Suara, et al., "Effect of Zinc Salts on Respiratory Syncytial Virus Replication," Antimicrobial Agents and Chemotherapy, Mar. 2004, pp. 783-790, vol. 48 (3).
Tabata and Ikada, "Macrophage phagocytosis of biodegradable microspheres composed of L-lactic acid/glycolic acid homo- and copolymers", J. Biomed. Mater. Res., 22:837-858 (1988).
Problemy Tuberkuleza, 58(1):40-41 (1980).
International Search Report dated Feb. 9, 2012 from corresponding PCT Application No. PCT/US2011/049435.
Jagdeep et al., "Cospray-Dried Unfractionated Heparin With L-Leucine as a Dry Powder Inhaler Mucolytic for Cystic Fibrosis Therapy," Journal of Pharmaceutical Sciences, 97 4857-4888 (2008).
International Search Report dated Jul. 1, 2013 from corresponding PCT Application No. PCT/US2013/028261.
Adi, et al., "Agglomerate strength and dispersion of pharmaceutical powders," Journal of Aerosol Science, 42:285-294, 2011.
Adjei and Garren, "Pulmonary delivery of peptide drugs: effect of partical size on bioavailability of leuprolide acelate in healthy male volunteers", J.Pharm. Res., 7 565-569 (1990).
Aldrich Catalog pp. 1502, 1998-1999.
Anderson, et al., "Effect of cystic fibrosis on inhaled aerosol boluses" Am. Rev. Raspir. Dis., 140: 1317-1324 (1989).
Bergeron, et al., "Controlling droplet deposition with polymer additives" Nature. 405:772-775 (2000).
Boren, "The development of a molecular model of lung" Arch Intern Med 126(3):491-495 (1970).
Broadhead, et al., The Spray Drying of Pharmaceuticals, Drug Development and Industrial Pharmacy, 18 (11&12):1169-1206, 1992.
Bromberg and Klibanov, "Transport of proteins in organic solvents across biomimetic membranes", Proc. Natl. Acad. Sci. USA, 92(5):1262-6 (1995).
Bucca, C. and G. Rolla, "Nebulised magnesium in asthma: the right solution for an old remedy?" The Lancet, 361:2095-2096 (2003).
Burg, et al., "Cellular Response to Hyperosmotic Stresses." Am. Physiological Soc., 87,1441-1474 (2007).
Cataldo, et al., "Induced sputum: comparison between isotonic and hypertonic saline solution inhalation in patients with asthma" Chest, 120(6) 1615-21 (2001).

Chan, H., "Spray Dried Powders and Powder Blends of Recombinant Human Deoxyribonuclease (rhDNase) for Aerosol Delivery," Pharmaceutical Research, 14(4): 431-437, 1997.
Jaffari, et al., "Rapid characterisation of the inherent dispersibility of respirable powders using dry dispersion laser diffraction," International Journal of Pharmaceuticals, 447:124-131, 2013.
Chiou, et al., "A novel production method for inhalable cyclosporine A powders by confined liquid impinging jet precipitation," Journal of Aerosol Science, 39:500-509, 2008.
Choi, et al., "Inhalation delivery of proteins from ethanol suspensions" Proc. Natl. Acad. Sci. 98 11103-11107 (2001).
Clarke, et al., "Resistance to two-phase-gas-liquid flow in airways" J. Appl. Physiol.29(4):464-471 (1970).
Copp, et al., "Hypertonic Shock Inhibits Growth Factor Receptor Signaling, Induces Caspase-3 Activation, and Causes Reversible Fragmentation of the Mitocholdrial Network," Am. J. Physiol, 288:C403-C415 (2005).
Costello, B., et al , "Use of the Du Nouy Ring with a Rotational Rheometer to Measure Rheology Properties", Annual Transactions of the Nordic Rheology Society. 2006, 14.
Crowder, et al., "2001 an Odyssey in Inhaler Formulation and Design," Pharmaceutical Technology, 99-113, Jul. 2001.
Davis, et al., "Charged Polymers Modulate Retrovirus Transduction via Membrane Charge Neutralization and Virus Aggregation", Biophys J,86:1234-1242 (2004).
Dawson, et al., "Enhanced viscoelasticity of human cystic fibrotic sputum correlates with Increasing microheterogeneity in particle transport", J. of Biol. Chem., 278(50):50393-50401.
Denn, M.M., "Viscoelasticity", In Process Fluid Mechanics, Prentice-Hall, Englewood Cliffs, New Jersey, pp. 358-373 (1980).
Edwards, et al., "Inhaling to mitigate exhaled bioaerosols," PNAS (2004), vol. 101, pp. 17383-17388.
Edwards, "The macrotransport of aerosol particles in the lung: aerosol deposition phenomena" J. Aerosol Sci., 26 293-317 (1995).
Edwards, et al., "Novel Inhalants for Control and Protection Against Airborne Infections," Respiratory Drug Delivery, 2006, pp. 41-48.
Eng Pa, et al., "Short-term efficacy of ultrasonically nebulized hypertonic saline in cystic fibrosis," Pediatr. Pulmonol., 21:77-83 (1996).
"European Search Report from corresponding EP Appl. No. 11177874 dated Nov. 21, 2011 (Ref.: 083277-0171; PUL 103EP-DIV2".
Evrensel, et al., "Viscous airflow through a rigid tube with compliant lining: A simple model for the air-mucus interaction in pulmonary pathways", J.Biomech. Eng., 115:262-267 (1993).
Feng, et al., "Improved clearability of cystic fibrosis sputum with dextran treatment in vitro," Am J. Respir. Crit. Care Med., 157(3):710-714 (1998).
Ferguson, et al., "Transmission Intensity and impact of control policies on the foot and mouth epidemic in Great Britain", Nature, 414(6881):329 (2001).
Fiegel et al., "Airborne Infectious Disease and the Suppression of Pulmonary Bioaerolsols," DDT, Jan. 2006, 11 (1/2), pp. 51-57.
Finlay, The Mechanics of Inhaled Pharmaceutical Aerosols, Academic Press, 143-149 (2001).
French, et al., "The influence of formulation on emission, deaggregation and deposition of dry powders for inhalation", J. Aerosol Sci., 27:769-783 (1996).
Friedmen, et al. "A Randomized, Prospective, Double-Blind Study on the Efficacy of Dead Sea Salt Nasal Irrigations," The Laryngoscope, 2006, pp. 878-882, 116.
Fuge, et al., "The geochemistry of iodine—a review", Environmental Geochemistry and Health, 8(2):31-54 (1986).
Gad-El-Hak, et al., "On the interaction of compliant coatings with boundary layer flows", J. Fluid Mech., 140:257.280 (1984).
Ganderton, "The generation of respirable clouds from coarse powder aggregates", Biopharmaceutical Sciences,3:101-105 (1992).
Geller, et al., "Development of a DPI Tobramycin Formulation using Pulmosphere Technology," J. of Aerosol Medicine and Pulmonary Drug Delivery, 24 175-182, 2011.
Ghoroi, et al., "A novel production method for inhalable cyclosporine A powders by confined liquid impinging jet precipitation," 85:11-24, 2013.

(56) References Cited

OTHER PUBLICATIONS

Goldberg, et al., "Mechanism of enhancement of microbial cell hydrophobicity by cationic polymers", J. Bacteriology, 172:5850-5654 (1990).

Gonda, "Aerosols for delivery of therapeutic and diagnostic agents to the respiratory tract", Critical Reviews in Therapeutic Drug Carrier Systems, 6:273-313 (1990).

Guo-Zhong Tao, et al., "Hyposmotic Stress Induces Cell Growth Arrest Via Proteasome Activation and Cyclin/Cyclin-Dependent Kinase Degradation," J. Biological Chemistry, 277(22): 19295-19303 (2002).

Hardy, et al. "Sensitivity of aerosol bolus behavior to Methacholine-induced bronchoconstriction", Chest, 114 (2):404-10 (1998).

Hatch, G.E., "Comparative Biochemistry of Airway Lining Fluid," In: Parent, R.A., Ed., Treatise on Pulmonary Toxicology, vol. 1: Comparative Biology of the Normal Lung, CRC Press, Boca Raton, Florida (1992).

Hawley's Condensed Chemical Dictionary, 14th edition John Wiley & Sons, 2001, pp. 161 and 977.

Heyder J., et al., "Deposition of particles in the human respiratory tract in the size range 0.005-15µm" J. Aerosol Sci., 17:811-825 (1986).

Hirschman, et al., "Inhibition of human immunodeficiency virus type 1 replication by nonionic block polymer surfactants" J. Med. Virol. 42(3):249-54 (1994).

* cited by examiner

INHALABLE DRY POWDERS

RELATED APPLICATIONS

This application is a continuation of U.S. application Ser. No. 15/495,450, filed Apr. 24, 2017, which is a divisional of U.S. application Ser. No. 14/378,453, filed Aug. 13, 2014, which is the U.S. National Stage of International Application No. PCT/US2013/028261, filed Feb. 28, 2013, published in English, which is a continuation of U.S. application Ser. No. 15/495,450, filed Apr. 24, 2017, which is a divisional of U.S. application Ser. No. 14/378,453, filed Aug. 13, 2014, which is the U.S. National Stage of International Application No. PCT/US2013/028261, filed Feb. 28, 2013, published in English, which claims the benefit of U.S. Patent Application No. 61/707,071, filed on Sep. 28, 2012, U.S. Patent Application No. 61/648,506, filed on May 17, 2012, U.S. Patent Application No. 61/645,927, filed on May 11, 2012, U.S. Patent Application No. 61/607,928, filed on Mar. 7, 2012, and U.S. Patent Application No. 61/605,083, filed on Feb. 29, 2012, the entire contents of each of which are incorporated herein by reference.

BACKGROUND

Several dry powder technologies, including lactose carrier particle blends, porous particles, and active inhaler (e.g., to deliver poorly dispersible powders), for delivery of therapeutic agents to the respiratory track exist, but each have limitations.

Lactose carrier particle blends use relatively large lactose particles, e.g. 40 micrometers to 250 micrometers, as a means of deagglomeration and aerosolization of micronized therapeutic agent. This leads to 1) dry powder formulations that have a low amount of therapeutic agents per unit of powder volume, and 2) dry powder formulations in which a relatively high percent of the therapeutic agent in the formulation adheres to and does not separate from the lactose carrier before the lactose carrier impacts the back of the patient's throat during inhalation and is swallowed. This latter point leads to high loss of therapeutic agent that never reaches the respiratory tract, thus requiring a significantly higher nominal dose to be administered than would otherwise be needed. The impaction in the upper throat can lead to hoarseness and oropharyngeal candidiasis, especially for corticosteroids. Additionally, digestion or exposure to therapeutic agents in the gastrointestinal tract leads to increased chance of undesired side effects. A third disadvantage to lactose blends is that the variety of therapeutic agents that are compatible with lactose blends is limited. It is well known that in general drugs should be crystalline when formulated with lactose blends. A fourth disadvantage of the lactose blending technology is that it has proven difficult to maintain uniform dosing to different areas of the respiratory tract, especially when the dry powder includes more than one therapeutic agent e.g., double and especially triple combinations. This is due to the fact that the various therapeutic agents are simply blended with the lactose, but the therapeutic agents are also bound to each other (e.g., homotypic and heterotypic binding), thus potentially resulting in different therapeutics depositing at different sites in the respiratory tract.

Porous particles tend to produce relatively homogenous dry powders. However, due to the porous nature of the powder, e.g., tap density of less than 0.4 $g/cm^3$, and often about 0.1 $g/cm^3$, the mass density and therefore therapeutic density, the amount of therapeutic agent per unit volume of powder, is also low. This means that in general a relatively large volume of dry particles that are porous is required to deliver an effective dose of therapeutic agent. A second drawback of porous particles in that they have poor processability. In fact, it is so difficult to process porous particles that primarily capsule-based technologies have been promoted in the attempt to commercialize porous particle platforms for therapeutic drug delivery. Some processability problems the porous particles face include, e.g., 1) bridging of the particles, e.g., across the opening of a receptacle, which limits the ability to fill receptacles with the dry powders for storage, distribution and/or dosing; across the receptacle, and 2) a tendency of the porous particles to aerosolize during filling processes and not settle into the desired receptacle for storage, distribution and later dosing.

Active inhalers use an energy source, other than the patient's breathing, to disperse the dry powder during administration. With this approach, poorly dispersible powders, such as micronized therapeutic agents, should be suitably dispersed for administration to the lungs. Although these devices held a lot of promise based on the theory of their operation, in practice they have not lived up to this promise. Due to their highly technical design, often including electronic circuitry, active inhalers have shown poor durability in tests that simulate ordinary wear and tear. Some active inhalers have used large volumes to disperse the dry powder, such as Nektar's Exubera device. However, the relatively large size of such devices is undesired by patients, and potentially leads to poor patient compliance.

There is a need for improved dry powder technology.

SUMMARY OF THE INVENTION

The invention relates to dry powders that contain a therapeutic agent. The dry powders have characteristics, e.g., they are processable and/or dense in therapeutic agents that provide advantages for formulating and delivering therapeutic agents to patients.

In some aspects, the respirable dry powder comprises respirable dry particles that contain at least one therapeutic agent and at least one metal cation salt, such as a sodium salt, a potassium salt, a magnesium salt, or a calcium salt, and that have a volume median geometric diameter (VMGD) about 10 micrometers or less. These dry particles can be further characterized by a tap density at least about 0.45 $g/cm^3$ to about 1.2 $g/cm^3$, at least about 0.55 $g/cm^3$ to about 1.1 $g/cm^3$, or at least about 0.65 $g/cm^3$ to about 1.0 $g/cm^3$; and a total content of therapeutic agent or agents of at least 25%, at least 35%, at least 50%, at least 65%, or at least 80% by weight (i.e., dry weight relative to the total dry weight of dry powder). The powders can be further characterized by an angle of repose of 50° or less, 40° or less, or 30° or less. The particles can be further characterized by a dispersibility ratio (1 bar/4 bar) of less than about 2 as measured by laser diffraction (RODOS/HELOS system), less than about 1.7, less than about 1.4, or less than about 1.2. The particles can be further characterized by a fine particle fraction (e.g., FPF<5.6, <5.0, <4.4 or <3.4) of 30% or greater, 40% or greater, 50% or greater, or 60% or greater.

The respirable dry powders comprising respirable dry particles, described in the aspects above, are preferably "processable." For example, the dry powders can be deposited or filled into a sealable receptacle that has a volume of about 12 cubic millimeters ($mm^3$) or less, a volume of about 9 $mm^3$ or less, a volume of about 6 $mm^3$ or less, a volume of about 3 $mm^3$ or less, a volume of about 1 $mm^3$ or less, or a volume of about 0.5 $mm^3$ or less, preferably to substantially fill the volume of the receptacle. Alternatively or in addition, the powders can be deposited or filled into a sealable receptacle to provide a mass of about 1 mg or less, about 0.75 mg or less, about 0.5 mg or less, about 0.3 mg or less, about 0.1 mg or less, or about 0.05 mg or less of powder in the receptacle.

The respirable dry powders consisting of respirable dry particles can be deposited into receptacles to provide a total dry powder mass of between about 5 mg to about 15 mg, between about 5 mg and less than 10 mg, between about 5 mg and about 9 mg, between about 5 mg and about 8 mg, or between about 5 mg and about 8 mg. The receptacles that contain the dry powder mass can be sealed if desired.

The dry powders comprising respirable dry particles can be deposited into receptacles to provide a total dry powder mass of about 5 mg or less, about 4 mg or less, about 3 mg or less or about 2 mg or less, and provide about 1 mg or more, wherein the total dry powder mass contains 1.5 mg or more, or about 2 mg or more of one or more therapeutic agents. In such embodiments, the receptacle will contain between 1.5 mg and about 5 mg or less, or about 2 mg and about 5 mg or less of total dry powder mass. The receptacles that contain the dry powder mass can be sealed if desired.

Preferably, the total content of therapeutic agent or agents in the respirable dry powder is at least 20%, at least 25%, at least 35%, at least 50%, at least 65%, or at least 80% by weight (i.e., dry weight relative to the total dry weight of dry powder). The one or more metal cation salt can be present in the respirable dry particles in any desired amount, such as about 3% by weight or more of the respirable particles, 5% by weight of the respirable particles, 10% by weight of the respirable particles, 15% by weight of the respirable particles, or in 20% by weight of the respirable particles. The one or more metal cation salt can independently be selected from the group consisting of a sodium salt, a potassium salt, a magnesium salt, and a calcium salt.

The respirable dry powder is filled or deposited into receptacles using standard filling equipment such as a vacuum dosator, for example, a rotating drum vacuum dosator, e.g., the Omnidose TT (Harro Hofliger, Germany). The volume of the receptacle into which the respirable dry powder is filled can be 400 microliters or less, 330 microliters or less, 250 microliters or less, 150 microliters or less, 70 microliters or less, 40 microliters or less, or 20 microliters or less. In one aspect, the respirable dry powder can be filled into two or more receptacles that are physically attached to each other or in an array, for example, using an interconnected blister piece comprising 30 blisters or more, 60 blisters or more, 90 blisters or more, or 120 blisters or more. Each receptacle or array of receptacles (e.g., an interconnected blister piece) can be filled at a rate of about every 10 seconds or less, about every 8 seconds or less, about every 6 seconds or less, about every 4 seconds or less, about every 2 seconds or less, or about every 1 second or less. Preferably, the relative standard deviation (RSD) is about 3% or less, about 2.5% or less, about 2% or less, or about 1.5% or less. A dry powder inhaler (DPI) that contains the receptacles can be any suitable DPI, such as a multi-dose blister DPI, a single-dose capsule DPI, or other DPI. The angle of repose of the respirable dry powder that is filled into the receptacles can be 50° or less, 40° or less, or 30° or less. The processable powder may be essentially free of non-respirable carrier particles, such as lactose, that have a VMGD that is greater than 10 micrometers, about 20 micrometers or greater, 30 micrometers or greater, or 40 micrometers or greater.

In other examples, the processable powders can be metered in a multi-dose reservoir dry powder inhaler (DPI), the metering achieved by a dosing cup, disk, or other structure for dosing in the reservoir DPI itself. Unit doses can be metered which are 100 cubic millimeters or less, 75 cubic millimeters or less, 50 cubic millimeters or less, 35 cubic millimeters or less, 20 cubic millimeters or less, 10 cubic millimeters or less, 5 cubic millimeters or less, or 2.5 cubic millimeters or less. In some aspects, the metering mechanism can possess one receptacle to measure a unit dose, and in other aspects, the metering mechanism can possess multiple receptacles to measure a unit dose. Alternatively or in addition, the processable powders can further be characterized as processable in that the mass of the metered dose from a multi-dose reservoir DPI is within 80% to 120% of a target mass 85% or more of the time, or within 85% to 115% of a target mass 90% of the time, or within 90% to 110% of a target mass 90% of the time. Preferably, the mass of the metered dose from a multi-dose reservoir DPI is within 85% to 115% of a target mass 90% or more of the time, or within 90% to 110% of a target mass 90% or more of the time.

The processable dry powders can be further be characterized by an angle of repose of 50° or less, 40° or less, 30° or less. Angle of repose is a characteristic that can describe both respirable dry powder as well as the powder's processability.

In addition or alternatively to any of the forgoing processability characteristics, the processable powders can further be filled into a receptacle for use in a DPI at a rate of one receptacle about every 10 seconds or less, about every 8 seconds or less, about every 6 seconds or less, about every 4 seconds or less, about every 2 seconds or less, about every 1 second or less, or about every 0.5 seconds or less; and/or filled into receptacles for use in a DPI at a rate of 300 receptacles every hour, 500 receptacles every hour, 750 receptacles every hour, 1100 receptacles every hour, 1500 receptacles every hour, 2000 receptacles every hour, 2500 receptacles every hour, or 3000 receptacles every hour. The rate of filling the receptacles can also be 800 receptacles or more every hour, 1600 receptacles or more every hour or 2400 receptacles or more every hour. Preferably, at least 70% of the receptacles are filled within 80% to 120% of the target fill weight, at least 80% of the receptacles are filled within 85% to 115% of the target fill weight, or 85% of the receptacles are filled within 90% to 110% of the target fill weight. More preferably, at least 85% of the receptacles are filled within 90% to 110% of the target fill weight.

In addition or alternatively to any of the forgoing processability characteristics, the processable powders can further be filled into a receptacle for use in a DPI at a rate of 300 receptacles or more every hour, 500 receptacles or more every hour, 750 receptacles or more every hour, 1100 receptacles or more every hour, 1500 receptacles or more every hour, 2000 receptacles or more every hour, 2500 receptacles or more every hour, or 3000 receptacles or more every hour. Preferably, at least 70% of the receptacles are filled within 80% to 120% of the target fill weight, at least 80% of the receptacles are filled within 85% to 115% of the target fill weight, or at least 85% of the receptacles are filled within 90% to 110% of the target fill weight. In addition or alternatively, the relative standard deviation of the fill weight is 3% or less, 2.5% or less, 2% or less, or 1.5% or less. Filling equipment that may be used include pilot scale equipment and commercial scale equipment.

The respirable dry powders are processable and preferably dispersible. Such dry powders can contain a proportionately large mass of one or more therapeutic agents (e.g., 50% or more (w/w) by dry weight) and be administered to a subject to deliver an effective amount of the therapeutic agent to the respiratory tract. For example, a unit dosage form of the dry powder, provided as a small volume receptacle (e.g., capsule or blister) with the dry powder disposed therein or as a reservoir-based DPI metered to dispense a small volume, can be used to deliver an effective amount of the therapeutic agent to the respiratory tract of a subject in need thereof. In one aspect, at least 20 milligrams of one or more therapeutic agent can be delivered to the respiratory tract from a small volume unit dosage form. For example, at least about 25 milligrams, at least about 30 milligrams, at least about 45 milligrams, at least about 60 milligrams, at least about 80 milligrams, at least about 100 milligrams, at least about 130 milligrams, at least about 160 milligrams, or at least about 200 milligrams of one or more therapeutic agent can be delivered to the respiratory tract from a unit dosage form provided as a small volume receptacle (e.g., volume of about 400 microliters or less, about 370 microliters or less, less than 370 microliters, about 300 microliters or less, less than about 300 microliters, preferably, about 370 microliters, or about 300 microliters) with the dry powder disposed therein. Preferably, the receptacle is a size 2 or a size 3 capsule. Suitable therapeutic agents that can be formulated as this type of dry powder and administered to the respiratory tract in this way include, but are not limited to, antibiotics (e.g., levofloxacin, tobramycin), antibodies (e.g., therapeutic antibodies), hormones (e.g. insulin), chemokines, cytokines, vaccines, growth factors, and combinations thereof. The most preferred therapeutic agent is an antibiotic, e.g., levofloxacin, tobramycin (Tobi®), aztreonam (Cayston®), gentamicin, and colistimethate sodium (Colobreathe®), ciprofloxacin, fosfomycin, and combinations thereof, e.g., gosfomycin and tobramycin. Other suitable therapeutic agents include, but are not limited to, long-acting beta2 agonists (LABA), e.g., formoterol, salmeterol; short-acting beta2 agonists, e.g., albuterol; corticosteroids, e.g., fluticasone; long-acting muscarinic anagonists (LAMA), e.g., tiotropium, glycopyrrolate, and Muscarinic Antagonist-Beta2 Agonists (MABA), e.g., GSK961081, AZD 2115, LAS190792, PF4348235, and PF3429281. Preferred therapeutic agents include, but are not limited to, LABAs (e.g., formoterol, salmeterol), short-acting beta agonists (e.g., albuterol), corticosteroids (e.g., fluticasone), LAMAs (e.g., tiotropium, glycopyrrolate), MABAs (e.g., GSK961081, AZD 2115, and LAS190792, PF4348235 and PF3429281), antibiotics (e.g., levofloxacin, tobramycin), antibodies and antigen-binding fragments of antibodies (e.g., therapeutic antibodies and antigen-binding fragments thereof, such as Fab, F(ab)'$_2$ and scFv fragments), hormones (e.g. insulin), chemokines, cytokines, growth factors, and combinations thereof. Preferred combinations of therapeutic agents include i) a corticosteroid and a LABA; ii) a corticosteroid and a LAMA; iii) a corticosteroid, a LABA and a LAMA; and iv) a corticosteroid and a MABA.

Features of the dry powders, receptacle and/or inhaler can be adjusted to achieve the desired delivery of an effective amount of the therapeutic agent to the respiratory tract of a subject in need thereof. Such features include 1) the therapeutic agent load in the dry particles or dry powder; 2) the bulk density of the dry powder, 3) the degree to which the receptacle is filled with the dry powder, and 4) the processability and dispersibility of the dry powder. The therapeutic agent load in the dry powder is generally at least about 25%, at least about 35%, at least about 50%, at least about 65%, at least about 80%, or at least about 90% by weight, on a dry basis. The bulk density of the dry powder is generally greater than 0.1 g/cc, between about 0.2 g/cc and about 0.9 g/cc, and preferably, at least about 0.3 g/ml, at least about 0.4 g/ml, or at least 0.5 g/ml. The bulk density, also referred to as the apparent density, is a measure that indicates how much dry powder can be filled into a fixed volume without the intense compaction experienced when determining the tap density of a dry powder. The receptacle is generally filled with dry powder to be at least 50% full, preferably, at least 60% full, at least 70% full, or at least 90% full. The processability and dispersibility of the dry powder can be altered, as desired, by including appropriate amounts of one or more monovalent and/or divalent metal cation salts, (e.g., a sodium salt, a potassium salt, a magnesium salt, a calcium salt, or a combination thereof, total metal cation salts less than about 75%, equal to or less than about 60%, about 50%, about 40%, about 30%, about 20%, about 10%, about 5%), and optionally, one or more other excipients (e.g., carbohydrates, sugar alcohols, and/or amino acids, total excipients equal to or less than about 70%, about 55%, about 40%, about 30%, about 20%, about 10%, about 5%) in the dry powders or dry particles. If desired, the therapeutic agent load may be at least about 20% by weight, on a dry basis. Although it is preferable that the receptacle is filled at least 50%, the receptacle can be filled to any desired degree, such as at least 10% filled, at least 20% filled, at least 30% filled, or at least 40% filled.

It is preferred that the dry powders are homogenous, i.e., contain one type of dry particle. In one preferred embodiment, the one or more metal cation salt consist of a sodium salt, a magnesium salt, and combinations thereof. In another embodiment, the one or more therapeutic agents do not include a calcium salt. In another preferred embodiment, the one or more metal cation salt consist of one or more sodium salt. In another preferred embodiment, the one or more metal cation salt consist of one or more magnesium salt.

Further features that can be adjusted to achieve the desired delivery of an effective amount of the therapeutic agent to the respiratory tract of a subject in need thereof include the fine particle dose (FPD<4.4 and/or <4.7) and the powder aerodynamic properties. The Andersen Cascade Impactor (ACI) is an apparatus that is commonly used to assess aerosol deposition in the respiratory tract. At a standardized testing condition, a pressure drop across the impactor of 4 kPa is employed to determine the fine particle dose of less than 4.4 micrometers (FPD(<4.4)), which indicates the mass of powder that has an aerodynamic diameter of less than 4.4 micrometers, and is representative of the mass which deposits in the lung. A cascade impactor, e.g. the ACI, can also be run at a challenge testing condition, where the pressure drop across the impactor is just 1 kPa and provides the fine particle dose of less than 4.7 micrometers (FPD(<4.7)), which indicates the mass of powder that has an aerodynamic diameter of less than 4.7 micrometers, representative of the mass which deposits in the lung. Generally, under standard conditions, the one or more therapeutic agents have an FPD(<4.4) under the standard testing conditions of at least about 25 milligrams, preferably at least about 30 milligrams, 40 milligrams, 50 milligrams, or 60 milligrams. Generally, the one or more therapeutic agents have an FPD(<4.7) under the challenge testing conditions of at least about 15 milligrams, preferably at least about 20 milligrams, 25 milligrams, 30 milligrams, 40 milligrams, or 50 milligrams.

It is preferred that the respirable dry particles described herein are further characterized by a capsule emitted powder mass of at least 80% when emitted from a passive dry powder inhaler that has a resistance of about 0.036 sqrt (kPa)/liters per minute under the following conditions: an inhalation energy of 1.15 Joules at a flow rate of 30 LPM using a size 3 capsule that contains a total mass of 25 mg, the total mass consisting of the respirable dry particles that comprise a divalent metal cation salt, and wherein the volume median geometric diameter of the respirable dry particles emitted from the inhaler is 5 microns or less.

Both the standard and challenge testing condition give insight into both how well the dry powder fluidizes in the capsule after actuation in the DPI, (an indications of powder processability), and how well the fluidized dry powder aerosolizes, (an indication of the powder dispersibility). Some representative capsule-based DPI units are RS-01 (Plastiape, Italy), Turbospin (PH&T, Italy), Breezhaler (Novartis, Switzerland), Aerolizer (Novartis, Switzerland), Podhaler (Novartis, Switzerland), and Handihaler (Boehringer Ingelheim, Germany). Some representative blister-based DPI units are Diskus (GlaxoSmithKline (GSK), UK), Diskhaler (GSK), Taper Dry (3M, Minnisota), Gemini (GSK), Twincer (University of Groningen, Netherlands), Aspirair (Vectura, UK), Acu-Breathe (Respirics, Minnisota, USA), Exubra (Novartis, Switzerland), Gyrohaler (Vectura, UK), Omnihaler (Vectura, UK), Microdose (Microdose Therapeutix, USA). Some representative reservoir-based DPI units are Clickhaler (Vectura), Next DPI (Chiesi), Easyhaler (Orion), Novolizer (Meda), Pulmojet (sanofi-aventis), Pulvinal (Chiesi), Skyehaler (Skyepharma), and Taifun (Akela).

Some preferred capsule-based DPI units are RS-01 (Plastiape, Italy), Turbospin (PH&T, Italy), Aerolizer (Novartis, Switzerland), Podhaler (Novartis, Switzerland), and Handihaler (Boehringer Ingelheim, Germany). Some preferred blister-based DPI units are Diskus (GlaxoSmithKline, UK), Taper Dry (3M, Minnisota), Gemini (GSK), Aspirair (Vectura, UK), Acu-Breathe (Respirics, Minnisota, USA), Gyrohaler (Vectura, UK), Omnihaler (Vectura, UK). Some preferred reservoir-based DPI units are Clickhaler (Vectura), Next DPI (Chiesi), Easyhaler (Orion), Novolizer (Meda), Flexhaler (AstraZeneca), and Pulmojet (Sanofi-Aventis).

In addition to FPD, an indirect measure of the aerodynamic properties of a respirable dry powder comprised of respirable dry particles can be accessed through the combination of the volumetric median geometric diameter (VMGD) and the tap density, which together give an indication of the aerodynamic diameter of the dry particles by means of the formula: the aerodynamic diameter equals the geometric diameter multiplied by the square root of the tap density. The VMGD of the dry particles is 10 micrometers or less. Preferably, it is between about 7 micrometers and 0.5 micrometers, between 5 micrometers and 0.75 micrometer, more preferably between 4.0 micrometers and 1.0 micrometer, between 3.5 micrometers and 1.5 micrometers, or between 2.5 micrometers and 1.0 micrometer. The tap density of the dry powder comprising dry particles is 0.45 $g/cm^3$ or greater. Preferably, it is between about 0.45 $g/cm^3$ to about 1.2 $g/cm^3$, between about 0.55 $g/cm^3$ to about 1.1 $g/cm^3$, more preferably between about 0.65 $g/cm^3$ to about 1.0 $g/cm^3$. Alternatively, the tap density is greater than 0.4 $g/cm^3$.

Another measure of processability for the respirable dry powder is angle of repose. The angle of repose is 50° or less, 40° or less, or 30° or less.

Respirable dry powders comprising respirable dry particles that are also processable provide advantages for patient use and enable new and useful areas of dry powder inhaler design and development. The respirable dry powder and particles are a robust platform that allows a wide array of therapeutic agents to be formulated as dry powders, thus greatly expanding the choice of therapeutics available for respiratory tract delivery. Furthermore, since the dry particles are substantially homogenous, i.e., each particle contains all components of the formulation (e.g., therapeutic agent, metal cation salt), the dose content of the powders, even in multiple therapeutic agent combination formulations (e.g., double and triple combination), is substantially uniform.

For example, respirable dry particles described herein are highly dispersible and can be dense (e.g., in total mass and/or have high therapeutic agent content (e.g., 25% or more by weight)). Thus, a relatively small mass and/or volume of powder needs to be administered to a patient, in comparison to other powder technologies, to achieve the desired therapeutic effects. This is a significant advantage for patients who are unable to adequately inhale larger volumes of dry powders, such as young children and patients with diminished lung function.

The dry powders described herein also provide significant advantages for patients who require therapeutic agents that produce or can produce undesired side effects, because the nominal dose that will be administered is lower than with other dry powder technologies. The dry powders described herein generally do not include non-respirable carrier particles (although such carrier particles can be incorporated for certain applications if desired), therefore no deagglomeration step is required to remove the therapeutic agent from the carrier. The high level of processability and dispersibility of the therapeutic dry particles leads to significantly higher levels of therapeutic agent reaching the respiratory tract when administer to a patient, thus requiring a lower nominal dose than with other dry powder technologies, such as lactose blend technology, and lowering the risk and/or incidence of side effects.

Exemplary dry powders that provide these advantages include, for example, those that contain particles that contain one or more therapeutic agent and at least one metal cation salt, are dispersible, are mass dense, e.g., 0.45 g/cm3 or greater, and preferably 0.55 $g/cm^3$ or 0.65 $g/cm^3$ or greater; and may be high in therapeutic agent content. Preferably, such respirable dry powders and particles are also highly processable, and are characterized by 1) low tendency to form particle bridges, and/or 2) they settle into small volume receptacles for storage and/or dosing.

Preferably, the dry particles are highly dispersible, and can be delivered to the respiratory tract of a patient using a passive DPI solely relying on the patient's own breathing pattern. Furthermore, the delivery of the respirable dry particles to the respiratory tract is preferably relatively independent of patient's inspiratory flowrate, meaning that the delivered dose is very similar for patients breathing in at a relatively high or low flow rates. Additionally, since the DPI can be a simple, passive device, i.e., it only relies on the patient's breathing pattern for energy, it can be made robust and able to withstand ordinary use testing.

These and other advantages of the respiratory dry powder and respiratory dry particles described herein, open up a new horizon of opportunity in the DPI field. The dry powders can be filled at low fill masses and/or fill volumes due to their high processability, while still containing high therapeutic agent content due to their mass density and/or therapeutic agent density. This enables therapeutically effective amounts of dry powder to be stored and dosed from small blisters and capsules. Consequently, smaller and/or more convenient DPIs (e.g., multi-dose blister DPI and single-dose capsule DPI) to be designed, for example, DPI that are smaller and/or contain more doses in a similar geometry to conventional DPI. Additionally, due to the same features of processability and high amount therapeutic agent per unit volume, the dry powder may be used in a multi-dose reservoir DPI. A key to successfully utilizing the reservoir DPI is to have consistent metering of the therapeutic dose. The high processability of the respirable dry powder makes it well suited for use in such a multi-dose reservoir DPI.

The combined properties of therapeutic dense per unit volume and high processability makes the therapeutic dry powder and therapeutic dry particles of the invention an enabling technology to advance the field of dry powder inhalation.

In certain embodiments, provided herein are respirable dry powders comprising respirable dry particles that comprise levofloxacin, a monovalent or divalent metal cation salt and optionally an excipient, wherein the dry particles comprise on a dry basis about 70% to about 90% levofloxacin, about 3% to about 25% metal cation salt and up to about 27% excipient, and wherein the respirable dry particles have a volume median geometric diameter (VMGD) about 10 micrometers or less, and a tap density at least about 0.45 g/cc. Preferably, the metal cation salt is a sodium salt and if an excipient is desired, preferably the ratio of sodium salt to excipient is about 1:2 on a weight basis (weight:weight). In other embodiments, the ratio of sodium salt to excipient is about 1:1 or about 2:1 (weight:weight). In yet other embodiments, the ratio of sodium salt to excipient is from about 1:1 to about 1:2 or from about 1:1 to about 2:1 on a weight basis (weight:weight). A preferred dry powder comprises respirable dry particles that comprise about 75% to about 90% levofloxacin, about 5% to about 10% sodium salt and about 10% to about 20% excipient. Another preferred metal cation salt is a magnesium salt. Preferably, if an excipient is desired, the ratio of magnesium salt to excipient is about 5:1 on a weight basis (weight:weight). In other embodiments, the ratio of magnesium salt to excipient is about 4:1, about 3:1, about 2:1 or about 1:1 (weight:weight). In yet other embodiments, the ratio of magnesium salt to excipient is from about 1:1 to about 5:1 or from about 1:1 to about 1:5 (weight:weight). A preferred dry powder comprises respirable dry particles that comprise about 70% to about 80% levofloxacin, about 15% to about 25% magnesium salt and about 0% to about 15% excipient. Preferred excipients are amino acids, preferably leucine but not limited thereto. For example, other amino acids suitable as excipients include alanine. Other preferred excipients are maltodextrin, mannitol, and trehalose. Exemplary dry powders comprising respirable dry particles are dry powders that comprise respirable dry particles that consist of either a) 75% levofloxacin, 25% magnesium lactate, b) 75% levofloxacin, 25% magnesium citrate, c) 75% levofloxacin, 25% magnesium sulfate, d) 70% levofloxacin, 25% magnesium lactate and 5% leucine, e) 70% levofloxacin, 25% magnesium lactate and 5% maltodextrin, and f) 82% levofloxacin, 6.3% sodium chloride and 11.7% leucine. Also provided herein are dry powder inhalers and receptacles comprising levofloxacin formulations described herein, e.g. one of the levofloxacin formulations of a) to f). The invention also relates to methods of treating a disease as described herein using the levofloxacin dry powder formulations, to the use of the levofloxacin dry powder formulations for treating disease, in therapy and in the preparation of medicaments for treating a disease as described herein.

BRIEF DESCRIPTION OF THE DRAWINGS

FIG. 7A and FIG. 7B are graphs showing a comparison in capsule emitted powder mass (CEPM) (7A) and volume median diameter (VMD) (7B) also referred to Dv50 of Formulation IX vs. a pure levofloxacin spray dried powder over a range of flow rates through a dry powder inhaler.

DETAILED DESCRIPTION

Definitions

Figure 1:
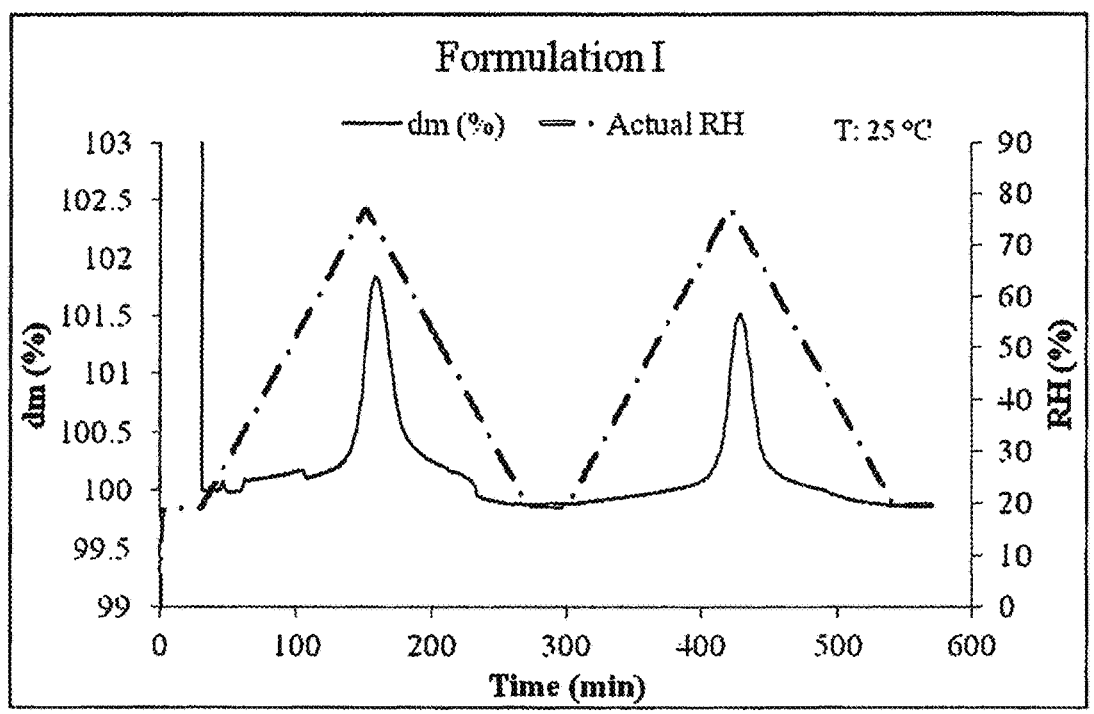
FIG. 1 is a plot of a dynamic vapor sorption (DVS) ramp mode experiment for Formulation I. See, Example 1.

The term "dry powder" as used herein refers to a composition that contains respirable dry particles that are capable of being dispersed in an inhalation device and subsequently inhaled by a subject. Such a dry powder may contain up to about 25%, up to about 20%, or up to about 15% water or other solvent, or be substantially free of water or other solvent, or be anhydrous.

The term "dry particles" as used herein refers to respirable particles that may contain up to about 25%, up to about 20%, or up to about 15% water or other solvent, or be substantially free of water or other solvent, or be anhydrous.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

The term "small" as used herein to describe respirable dry particles refers to particles that have a volume median geometric diameter (VMGD) of about 10 microns or less, preferably about 5 microns or less. VMGD may also be called the volume median diameter (VMD), ×50, or Dv50.

As used herein, the terms "administration" or "administering" of respirable dry particles refers to introducing respirable dry particles to the respiratory tract of a subject.

As used herein, the term "respiratory tract" includes the upper respiratory tract (e.g., nasal passages, nasal cavity, throat, and pharynx), respiratory airways (e.g., larynx, trachea, bronchi, and bronchioles) and lungs (e.g., respiratory bronchioles, alveolar ducts, alveolar sacs, and alveoli).

The term "dispersible" is a term of art that describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, VMGD at 0.5 bar divided by the VMGD at 4 bar as measured by HELOS/RODOS, VMGD at 0.2 bar divided by the VMGD at 2 bar as measured by HELOS/RODOS, or VMGD at 0.2 bar divided by the VMGD at 4 bar as measured by HELOS/RODOS. These quotients are referred to herein as "1 bar/4 bar," "0.5 bar/4 bar," "0.2 bar/2 bar," and "0.2 bar/4 bar," respectively, and dispersibility correlates with a low quotient. For example, 1 bar/4 bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a 1 bar/4 bar or 0.5 bar/4 bar ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by a subject. Dispersibility can also be assessed by measuring the size emitted from an inhaler as a function of flow rate. VMGD may also be called the volume median diameter (VMD), ×50, or Dv50.

An example of dispersibility measured with the size emitted from an inhaler as a function of flow rate is the VMGD (Dv50) at either 15 LPM or 20 LPM, measured as emitted from an actuated dry powder inhaler (DPI) by laser diffraction, divided by the measured Dv50 at either 60 LPM. One example of this measurement is the Dv50 measured emitting from an RS-01 HR DPI (Plastiape, Italy) at 15 LPM/60 LPM or 20 LPM/60 LPM, using a Spraytec diffractometer (Malvem, Inc., Westborough, Mass.). These quotients are referred to herein as "15 LPM/60 LPM," "20 LPM/60 LPM," respectively, and dispersibility correlates with a low quotient. For example, 15 LPM/60 LPM refers to the Dv50 of respirable dry particles or powders emitted from the RS-01 DPI (or equivalent DPI) at about 15 LPM, as measured by a Spraytec or other laser diffraction system, divided the Dv50 of the same respirable dry particles or powders measured at 60 LPM by the Spraytec. Thus, a highly dispersible dry powder or dry particles will have a 15 LPM/60 LPM ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by a subject.

An example of an equivalent DPI to the RS-01 DPI is one that has a resistance that is within about 20%, within about 10%, or within about 5% of about 0.036 sqrt(kPa)/liters per minute.

The terms "FPF (<5.6)," "FPF (<5.6 microns)," and "fine particle fraction of less than 5.6 microns" as used herein, refer to the fraction of a sample of dry particles that have an aerodynamic diameter of less than 5.6 microns. For example, FPF (<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD(<5.6)," where TD means total dose. A similar measurement can be conducted using an eight-stage ACI. The eight-stage ACI cutoffs are different at the standard 60 L/min flow rate, but the FPF_TD(<5.6) can be extrapolated from the eight-stage complete data set. The eight-stage ACI result can also be calculated by the USP method of using the dose collected in the ACI instead of what was in the capsule to determine FPF.

The terms "FPF (<5.0)", "FPF<5 µm", "FPF (<5.0 microns)," and "fine particle fraction of less than 5.0 microns" as used herein, refer to the fraction of a mass of respirable dry particles that have an aerodynamic diameter of less than 5.0 micrometers. For example, FPF (<5.0) can be determined by using an eight-stage ACI at the standard 60 L/min flow rate by extrapolating from the eight-stage complete data set. This parameter may also be identified as "FPF_TD(<5.0)," where TD means total dose. When used in conjunction with a geometric size distribution such as those given by a Malvern Spraytec, Malvern Mastersizer or Sympatec HELOS particle sizer, "FPF (<5.0)" refers to the fraction of a mass of respirable dry particles that have a geometric diameter of less than 5.0 micrometers.

The terms "FPD (<4.4)", 'FPD<4.4 µm", FPD (<4.4 microns)" and "fine particle dose of less than 4.4 microns" as used herein, refer to the mass of respirable dry powder particles that have an aerodynamic diameter of less than 4.4 micrometers. For example, FPD<4.4 µm can be determined by summing the mass deposited on the filter, and stages 6, 5, 4, 3, and 2 for a single dose of powder actuated into the ACI. Preferably the methods of section <601> of the United States Pharmacopeia (30th edition) are followed, by using a cascade impactor at a pressure drop across of 4 kPa. For example using an eight-stage ACI and a RS-01 HR dry powder inhaler under the standard condition of 4 kPa pressure drop corresponds to a flow rate of 60 L/min through the inhaler and FPD<4.4 µm is quantified by summing the mass deposited on the filter, and stages 6, 5, 4, 3, and 2 for a single dose of powder actuated into the ACI.

The terms "FPD (<4.7)", 'FPD<4.7 µm", FPD (<4.7 microns)" and "fine particle dose of less than 4.7 microns" as used herein, refer to the mass of respirable dry powder particles that have an aerodynamic diameter of less than 4.7 micrometers. For example, FPD<4.7 µm can be determined by the methods of section <601> of the United States Pharmacopeia (30th edition), by using a cascade impactor at a challenge pressure drop across of 1 kPa rather than the standard condition pressure drop of 4 kPA. For example using an eight-stage ACI and a RS-01 HR dry powder inhaler under the challenge condition of 1 kPa pressure drop corresponds to a flow rate of 28.3 L/min through the inhaler, and FPD<4.7 µm is quantified by summing the mass deposited on the filter, and stages 7, 6, 5, 4, and 3, for a single dose of powder actuated into the ACI.

The terms "FPF (<3.4)," "FPF (<3.4 microns)," and "fine particle fraction of less than 3.4 microns" as used herein, refer to the fraction of a mass of respirable dry particles that have an aerodynamic diameter of less than 3.4 microns. For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD(<3.4)," where TD means total dose. A similar measurement can be conducted using an eight-stage ACI. The eight-stage ACI result can also be calculated by the USP method of using the dose collected in the ACI instead of what was in the capsule to determine FPF.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, Md., $13^{th}$ Revision, 222-225, 2007. This method utilizes an in vitro device set up to mimic patient dosing.

The term "capsule emitted powder mass" or "CEPM" as used herein, refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The capsule emitted powder mass (CEPM) as measured at a high inhalation flow rate of 60 liters per minutes (LPM) through an dry powder inhaler (DPI) by laser diffraction (e.g., Spraytec system), compared to a low inhalation flow rate of 15 LPM, is influenced by both processability and dispersibility. The particles are preferably characterized by a CEPM Ratio (60 LPM/15 LPM) of less than 1.5, less than 1.4, and preferably, less than 1.3, less than 1.2, or less than 1.15. Another parameter that combines processability with dispersibility is the volumetric median geometric diameter (VMGD), also referred to as Dv(50), as measured at a high inhalation flow rate of 60 LPM through a DPI as measured by laser diffraction (e.g., Spraytec system), compared to a low inhalation flow rate of 15 LPM. The particles are preferably characterized by a Dv(50) from DPI Ratio (15 LPM/60 LPM) of less than 5, less than 4, and preferably, less than 3, less than 2.5, less than 2, or less than 1.5. The lower flowrate for the CEPM Ratio and the Dv(50) from DPI Ratio may also be calculated at 20 LPM. The values for these ratios are similar to the values given above. These two ratio values, CEPM Ratio and Dv(50) from DPI Ratio reflect a dry powder's ability to be processed from a packed bed of dry powder into a fluidized bed and then to disperse and aerosolize into individual particles.

The term "effective amount," as used herein, refers to the amount of therapeutic agent needed to achieve the desired therapeutic or prophylactic effect, such as an amount that is sufficient to reduce pathogen (e.g., bacteria, virus) burden, reduce symptoms (e.g., fever, coughing, sneezing, nasal discharge, diarrhea and the like), reduce occurrence of infection, reduce viral replication, or improve or prevent deterioration of respiratory function (e.g., improve forced expiratory volume in 1 second $FEV_1$ and/or forced expiratory volume in 1 second $FEV_1$ as a proportion of forced vital capacity $FEV_1$/FVC, reduce bronchoconstriction), produce an effective serum concentration of a therapeutic agent, increase mucociliary clearance, reduce total inflammatory cell count, or modulate the profile of inflammatory cell counts. The actual effective amount for a particular use can vary according to the particular dry powder or dry particle, the particular therapeutic agent(s), the mode of administration, and the age, weight, general health of the subject, and severity of the symptoms or condition being treated. Suitable amounts of dry powders and dry particles to be administered, and dosage schedules for a particular patient can be determined by a clinician of ordinary skill based on these and other considerations.

The term "pharmaceutically acceptable excipient" as used herein means that the excipient can be taken into the lungs with no significant adverse toxicological effects on the lungs. Such excipients are generally regarded as safe (GRAS) by the U.S. Food and Drug Administration.

All references to salts (e.g., sodium containing salts) herein include anhydrous forms and all hydrated forms of the salt. All weight percentages are given on a dry basis.

Dry Powders and Dry Particles

The respirable dry powders and dry particles described herein contain one or more metal cation salts, which can be monovalent metal cation salts, divalent metal cation salts, or combinations thereof. For example, the respirable dry powders and dry particles can contain one or more salts selected from the group consisting of sodium salts, potassium salts, magnesium salts, calcium salts, and combinations thereof.

Monovalent metal cation salts suitable for use in the dry powders and dry particles of the invention include, for example, a sodium salt, a potassium salt, a lithium salt and any combination thereof.

Suitable sodium salts that can be present in the dry particles include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, dibasic sodium phosphate, sodium phosphate, sodium bisulfite, sodium borate, sodium gluconate, sodium metasilicate, sodium propionate and the like.

Suitable potassium salts include, for example, potassium chloride, potassium citrate, potassium bromide, potassium iodide, potassium bicarbonate, potassium nitrite, potassium persulfate, potassium sulfite, potassium sulfate, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium tartrate and any combination thereof.

Suitable lithium salts include, for example, lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate or any combination thereof.

Divalent metal cation salts suitable for use in the dry powders and dry particles of the invention include, for example, a calcium salt, a potassium salt, a beryllium salt, a strontium salt, a barium salt, a radium salt, an a iron (ferrous) salt, and combinations thereof.

Suitable calcium salts that can be present in the dry particles described herein include, for example, calcium chloride, calcium sulfate, calcium lactate, calcium citrate, calcium carbonate, calcium acetate, calcium phosphate, calcium alginate, calcium stearate, calcium sorbate, calcium gluconate and the like.

Suitable magnesium salts that can be present in the dry particles described herein include, for example, magnesium fluoride, magnesium chloride, magnesium bromide, magnesium iodide, magnesium lactate, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof.

Suitable beryllium salts include, for example, beryllium phosphate, beryllium acetate, beryllium tartrate, beryllium citrate, beryllium gluconate, beryllium maleate, beryllium succinate, sodium beryllium malate, beryllium alpha brom camphor sulfonate, beryllium acetylacetonate, beryllium formate or any combination thereof.

Suitable strontium salts include, for example, strontium chloride, strontium phosphate, strontium sulfate, strontium carbonate, strontium oxide, strontium nitrate, strontium acetate, strontium tartrate, strontium citrate, strontium gluconate, strontium maleate, strontium succinate, strontium malate, strontium aspartate in either L and/or D-form, strontium fumarate, strontium glutamate in either L- and/or D-form, strontium glutarate, strontium lactate, strontium L-threonate, strontium malonate, strontium ranelate (organic metal chelate), strontium ascorbate, strontium butyrate, strontium clodronate, strontium ibandronate, strontium salicylate, strontium acetyl salicylate or any combination thereof.

Suitable barium salts include, for example, barium hydroxide, barium fluoride, barium chloride, barium bromide, barium iodide, barium sulfate, barium sulfide (S), barium carbonate, barium peroxide, barium oxide, barium nitrate, barium acetate, barium tartrate, barium citrate, barium gluconate, barium maleate, barium succinate, barium malate, barium glutamate, barium oxalate, barium malonate, barium naphthenate, barium acetylacetonate, barium formate, barium benzoate, barium p-t-butylbenzoate, barium adipate, barium pimelate, barium suberate, barium azelate, barium sebacate, barium phthalate, barium isophthalate, barium terephthalate, barium anthranilate, barium mandelate, barium salicylate, barium titanate or any combination thereof.

Suitable radium salts include, for example, radium fluoride, radium chloride, radium bromide, radium iodide, radium oxide, radium nitride or any combination thereof.

Suitable iron (ferrous) salts include, for example, ferrous sulfate, ferrous oxides, ferrous acetate, ferrous citrate, ferrous ammonium citrate, ferrous gluconate, ferrous oxalate, ferrous fumarate, ferrous maleate, ferrous malate, ferrous lactate, ferrous ascorbate, ferrous erythrobate, ferrous glycerate, ferrous pyruvate or any combination thereof.

If desired, the formulations, dry powders or dry particles may comprise a salt other than a monovalent or divalent metal cation salt. For example, the formulation may comprise a trivalent or other multivalent salt, such as one or more non-toxic salts of the elements aluminum, silicon, scandium, titanium, vanadium, chromium, cobalt, nickel, copper, manganese, zinc, tin, silver and the like.

Preferably, the dry particles contain at least one divalent metal cation salt, at least one monovalent metal cation salt, or at least one divalent metal cation salt and at least one monovalent metal cation salt. Preferably, the monovalent metal cation salt is a sodium or potassium salt, and the divalent metal cation salt is a calcium or magnesium salt. Preferred sodium salts are sodium citrate, sodium chloride, sodium lactate, and sodium sulfate. Preferred potassium salts are potassium citrate and potassium sulfate. Preferred calcium salts are calcium lactate, calcium sulfate, calcium citrate, and calcium carbonate. Preferred magnesium salts are magnesium sulfate, magnesium lactate, magnesium chloride, magnesium citrate, and magnesium carbonate.

If desired, at least one divalent metal cation salt, at least one monovalent cation salt, or combinations thereof contain chloride, lactate, citrate or sulfate as a counter ion. In one embodiment, the preferred counter ion is lactate. In another embodiment, the preferred counter ion is citrate. In another embodiment, the preferred counter ion is sulfate.

If desired, the dry particles can contain a divalent metal cation salt (e.g., calcium salt or magnesium salt) which provides divalent cation (e.g., $Ca^{2+}$ or $Mg^{2+}$), a monovalent salt (e.g., sodium salt, lithium salt, potassium salt) which provides monovalent cation (e.g., $Na^+$, $Li^+$, $K^+$), or combinations thereof. The one or more cations can be present in a low amount, e.g., less than 20%, in a medium amount, e.g., 20% to 40%, or in a high amount, e.g., greater than 40%, with all values representing the total weight percentage of the cations present in the dry particles, on a dry weight basis. For example, the dry particles can include low amounts of a divalent metal cation salt (e.g., calcium salt or magnesium salt) which provides divalent cation (e.g., $Ca^{2+}$ or $Mg^{2+}$), a monovalent salt (e.g., sodium salt, potassium salt) which provides monovalent cation (e.g., $Na^+$, $K^+$), or combinations thereof, in an amount 17.5% or less, 15% or less, 12.5% or less, 10% or less, 8% or less, 6% or less, 5% or less, 4% or less, 3% or less, 2% or less, 1% or less; medium amounts in an amount 25% up to 40%, 30% up to 40%, 35%, up to 40%, 20% up to 35%, 20% up to 30%, 20% up to 25%, or 22.5% to 37.5%, 25% to 35%, 27.5% to 32.5%; or high amounts in an amount greater than 45%, greater that 50%, greater than 55%, greater than 60%, all by weight percent of the dry particles. In a preferred embodiment, the divalent metal cation, monovalent metal cation, or combinations thereof is present in the dry particles in a low amount, e.g., less than 20%, 15% or less, 10% or less, or 5% or less, all by weight percent of the dry particles.

In another preferred embodiment, the divalent metal cation, monovalent metal cation, or combination thereof is present in the dry particles in a low amount, e.g., between about 1% and about 20%, between about 2% and about 20%, between about 3% and about 20%, between about 3% and about 15%, between about 3% and about 10%, between about 3% and about 5%, between about 5% and about 20%, between about 5% and about 15%, or between about 5% and about 10%, all by weight percent of the dry particles.

If desired, the dry particles can contain a divalent metal cation salt which provides divalent cation (e.g., $Ca^{2+}$, $Be^{2+}$, $Mg^{2+}$, $Sr^{2+}$, $Ba^{2+}$, $Fe^{2+}$), a monovalent salt (e.g., sodium salt, lithium salt, potassium salt) which provides monovalent cation (e.g., $Na^+$, $Li^+$, $K^+$), or combinations thereof, the salt being present in the dry particles in various ranges. The one or more metal cation salt can be present in a low amount, e.g., less than 30%, in a medium amount, e.g., 30% to 60%, or in a high amount, e.g., greater than 60%, with all values representing the total weight percentage of the salts present in the dry particles, on a dry weight basis. For example, the dry particles can include low amounts of a divalent metal cation salt (e.g., calcium salt or magnesium salt), a monovalent salt (e.g., sodium salt, potassium salt), or combinations thereof, in an amount 27.5% or less, 25% or less, 22.5% or less, 20% or less, 17.5% or less, 15% or less, 12.5% or less, 10% or less, 7.5% or less, 5% or less, 2.5% or less; medium amounts in an amount 35% up to 60%, 40% up to 60%, 45%, up to 60%, 50% up to 60%, 30% up to 55%, 30% up to 50%, 30% up to 45%, 30% up to 40%, or 32.5% to 57.5%, 35% to 55%, 37.5% to 52.5%, 40% to 50%, 42.5% to 47.5%; or high amounts in an amount greater than 65%, greater that 70%, greater than 75%, greater than 80%, greater than 90%, all by weight percent of the dry particles. In a preferred embodiment, the divalent metal cation salt, monovalent metal cation salt, or combinations thereof are present in the dry particles in a low amount, e.g., less than 30%, 25% or less, 20% or less, 15% or less, 10% or less, 5% or less, all by weight percent of the dry particles.

In another preferred embodiment, the divalent metal cation salt, monovalent metal cation salt, or combination thereof is present in the dry particles in a low amount, e.g., between about 1% and about 30%, between about 2% and about 30%, between about 3% and about 30%, between about 4% and about 30%, between about 5% and about 30%, between about 5% and about 25%, between about 3% and about 20%, between about 5% and about 15%, between about 5% and about 10%, between about 10% and about 30%, between about 10% and about 25%, between about 10% and about 20%, or between about 10% and about 15%, all by weight percent of the dry particles.

If desired, the dry particles can contain a divalent metal cation salt and a monovalent cation salt, where the weight ratio of divalent cation to monovalent cation is about 50:1 (i.e., about 50 to about 1) to about 0.02:1 (i.e., about 0.02 to about 1). The weight ratio of divalent metal cation to monovalent cation, is based on the amount of divalent metal cation and monovalent cation that are contained in the divalent metal cation salt and monovalent salts, respectively that are contained in the dry particle. In particular examples, the weight ratio of divalent metal cation to monovalent cation is about 50:1 to about 40:1, about 40:1 to about 30:1, about 30:1 to about 20:1, about 20:1 to about 10:1, about 10:1 to about 5:1, 5:1 to about 2:1, about 2:1 to about 1:1, about 1:1 to about 1:2, about 1:2 to about 1:5, about 1:5 to about 1:10, about 1:10 to about 1:20, about 1:20 to about 1:30, about 1:30 to about 1:40, about 1:40 to about 1:50.

In particular examples, divalent metal cation and monovalent cation, respectively, are present in the dry particles in a mole ratio of about 8.0:1, about 7.5:1, about 7.0:1, about 6.5:1, about 6.0:1, about 5.5:1, about 5.0:1, about 4.5:1, about 4.0:1, about 3.5:1, about 3.0:1, about 2.5:1, about 2.0:1, about 1.5:1, about 1.0:1, about 0.77:1, about 0.65:1, about 0.55:1, about 0.45:1, about 0.35:1, about 0.25:1, about 0.2:1; or about 8.0:1 to about 1.5:1, about 7.0:1 to about 1.5:1, about 6.0:1 to about 1.5:1, about 5.0:1 to about 1.5:1, about 4.0:1 to about 1.5:1, about 3.5:1 to about 1.5:1, about 3.0 to about 1.5:1, about 8.0:1 to about 2.0:1, about 2.0:1 to about 2.0:1, about 6.0:1 to about 2.0:1, about 5.0:1 to about 2.0:1, about 4.0:1 to about 2.0:1, about 3.5:1 to about 2.0:1, about 3.0 to about 2.0:1, about 4.0:1. In one embodiment, the divalent metal cation, as a component of one or more divalent metal cation salts, is present in an amount of at least 5% by weight of the dry particle.

If desired, the ratio of divalent metal cation (e.g., $Ca^{2+}$, $Be^{2+}$, $Mg^{2+}$, $Sr^{2+}$, $Ba^{2+}$, $Fe^{2+}$) to monovalent cation (e.g., $Na^+$, $Li^+$, $K^+$) mole:mole can be about 16.0:1.0 to about 1.5:1.0, about 16.0:1.0 to about 2.0:1.0, about 8.0:1.0 to about 1.5:1.0, about 8.0:1.0 to about 2.0:1.0, about 4.0:1.0 to about 1.5:1.0, about 5:0:1.0 to about 2.0:1.0. More preferably, the divalent metal cation and monovalent cation are present in the dry particles in a mole ratio of about 8.0:1.0 to about 2.0:1.0 or about 5.0:1.0 to about 3.0:1.0. Most preferably, the divalent metal cation is $Ca^{2+}$ and the monovalent cation is $Na^+$.

If desired, dry particles can contain a high percentage of monovalent metal cation salt (e.g., a sodium salt and/or potassium salt) in the composition. The dry particles may contain 3% or more, 5% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more monovalent metal cation salt (e.g., sodium salt or potassium salt) by weight.

If desired, the dry particles can contain a monovalent metal cation salt (e.g., sodium salt or potassium salt), which provides monovalent cation (e.g., $Na^+$ or $K^+$) in an amount of at least about 1% by weight of the dry particles. For example, the dry particles can include a sodium salt or potassium salt which provides $Na^+$ or $K^+$, in an amount of at least about 3% by weight, at least about 5% by weight, at least about 7% by weight, at least about 10% by weight, at least about 11% by weight, at least about 12% by weight, at least about 13% by weight, at least about 14% by weight, at least about 15% by weight, at least about 17% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight or at least about 70% by weight of the dry particles.

If desired, the dry particles can contain one or more monovalent metal cation salts (e.g., sodium salts and potassium salts), divalent metal cation salts (e.g. calcium salts and magnesium salts), or a combination thereof, in a total amount of about 1% to about 20% by weight of the dry particles, greater than about 20% to about 60% by weight of the dry particles, or greater than about 60% to about 100% by weight of the dry particles. For example, the dry particles can include one or more of the monovalent metal cation salts, the divalent metal cation salts, or a combination thereof, in a total amount of between about 1% and about 5%, greater than about 5% to about 10%, greater than about 10% to about 15%, greater than about 15% to about 20%, greater than about 20% to about 30%, greater than about 30% to about 40%, greater than about 40% to about 50%, greater than about 50% to about 60%, greater than about 60% to about 70%, greater than about 70% to about 80%, greater than about 80% to about 90%, or greater than about 90% to 95%, greater than about 95% to about 99%, or greater than about 99% to about 100%, all percentages are by weight of the dry particles.

If desired, the dry particles can contain a total salt content (e.g., of monovalent and/or divalent cation salts) of less than about 51% by weight of the dry particles. For example, the dry particles can include one or more of the salts in a total amount of less than about 45%, less than about 40%, less than about 35%, less than about 30%, less than about 25%, less than about 20%, less than about 15%, less than about 10%, less than about 9%, less than about 8%, less than about 5%, or less than about 3% by weight of the dry particles. In certain embodiments, the divalent metal cation is present at less than 3% by weight of dry particle.

Therapeutic Agents

Therapeutic Agents suitable for the formulations, dry powders and dry particles described herein include any pharmaceutical, veterinary product, agrochemical, and or cosmetic substance. In particular aspects of the invention, a Therapeutic Agent includes any biologically or pharmacologically active substance or antigen-comprising material; the term includes drug substances which have utility in the treatment or prevention of diseases or disorders affecting animals or humans, or in the regulation of any animal or human physiological condition and it also includes any biologically active compound or composition which, when administered in an effective amount, has an effect on living cells or organisms.

Aspects of the invention include dry particles that contain one or more monovalent metal cation salts, such as a sodium salt and/or a potassium salt, and/or one or more divalent metal cation salts, such as a calcium salt and/or magnesium salt, and further contain one or more therapeutic agents, such as any of the therapeutic agents described herein.

The dry particles can contain a large amount of therapeutic agent, e.g., 5% or more, 10% or more, 20% or more, 30% or more, 40% or more, 50% or more, 60% or more, 70% or more, 80% or more, 90% or more, 95% or more, or 97% or more by weight of the dry particle. When an excipient is included in the dry particles, the excipient may comprise about, 50% or less by weight, about 40% or less by weight, about 30% or less by weight, about 20% or less by weight, about 12% or less by weight, about 10% or less by weight, about 8% or less by weight, about 5% or less by weight, about 3% or less by weight, about 2% or less by weight or about 1% or less by weight. For example, the excipient may comprise about 1% to about 50%, about 2% to about 50%, about 3% to about 50%, about 5% to about 50%, about 10% to about 50%, about 20% to about 50%, about 5% to about 40%, about 5% to about 30%, about 5% to about 20%, or about 1% to about 10%, all by weight percent of the dry particles.

The dry particles can contain a therapeutic agent in the following weight ranges: about 5% to about 15%, about 15% to about 25%, about 25% to about 35%, about 35% to about 45%, about 45% to about 55%, about 55% to about 65%, about 65% to about 75%, about 75% to about 85%, about 85% to about 95%; or about 10%, about 20%, about 30%, about 40%, about 50%, about 60%, about 70%, about 80%, or about 90% by weight.

Any of the therapeutic agents may be administered in the form of a salt, ester, amide, pro-drug, active metabolite, isomer, analog, fragment, and the like, provided that the salt, ester, amide, pro-drug, active metabolite, isomer, analog or fragment, is pharmaceutically acceptable and pharmacologically active in the present context. Salts, esters, amides, pro-drugs, metabolites, analogs, fragments, and other derivatives of the therapeutic agents may be prepared using standard procedures known to those skilled in the art, for example the art of synthetic organic chemistry, and described, for example, by J. March, Advanced Organic Chemistry: Reactions, Mechanisms and Structure, 4th Edition (New York: Wiley-Interscience, 1992).

For example, acid addition salts are prepared from a drug in the form of a free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties that may be present on a therapeutic agent may be carried out in a similar manner using a pharmaceutically acceptable base such as sodium hydroxide, potassium hydroxide, ammonium hydroxide, calcium hydroxide, trimethylamine, and the like. Preparation of esters involves transformation of a carboxylic acid group via a conventional esterification reaction involving nucleophilic attack of an RO-moiety at the carbonyl carbon. Esterification may also be carried out by reaction of a hydroxyl group with an esterification reagent such as an acid chloride. Esters can be reconverted to the free acids, if desired, by using conventional hydrogenolysis or hydrolysis procedures.

Amides may be prepared from esters, using suitable amine reactants, or they may be prepared from an anhydride or an acid chloride by reaction with ammonia or a lower alkyl amine. Pro-drugs and active metabolites may also be prepared using techniques known to those skilled in the art or described in the pertinent literature. Pro-drugs are typically prepared by covalent attachment of a moiety that results in a compound that is therapeutically inactive until modified e.g. by an individual's metabolic system.

Other derivatives and analogs of the therapeutic agents may be prepared using standard techniques known to those skilled in the art of synthetic organic chemistry, or may be deduced by reference to the pertinent literature. In addition, chiral therapeutic agents may be in isomerically pure form, or they may be administered as a racemic mixture of isomers.

International Patent Application No. PCT/US2011/053829, filed on Sep. 29, 2011, and titled "Monovalent Metal Cation Dry Powders", paragraphs 96 to 153 which list suitable therapeutic agents, is incorporated by reference herein.

Suitable therapeutic agents for use in the respirable dry powders and respirable dry particles include mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF).

Preferred therapeutic agents include, but are not limited to, LABAs (e.g., formoterol, salmeterol), short-acting beta agonists (e.g., albuterol), corticosteroids (e.g., fluticasone), LAMAs (e.g., tiotropium), MABAs (e.g., GSK961081, AZD 2115, and LAS190792), antibiotics (e.g., levofloxacin, tobramycin), antibodies (e.g., therapeutic antibodies), hormones (e.g. insulin), chemokines, cytokines, growth factors, and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof. In certain embodiments, the therapeutic agent(s) can be blended with the respirable dry particles described herein, or co-formulated (e.g., spray dried) as desired. Preferred therapeutic agents include, but are not limited to, LABAs (e.g., formoterol, salmeterol), short-acting beta agonists (e.g., albuterol), corticosteroids (e.g., fluticasone), LAMAs (e.g., tiotropium, glycopyrrolate), MABAs (e.g., GSK961081, AZD 2115, and LAS190792, PF4348235 and PF3429281), antibiotics (e.g., levofloxacin, tobramycin), antibodies (e.g., therapeutic antibodies), hormones (e.g. insulin), chemokines, cytokines, growth factors, and combinations thereof. Preferred combination of two or more therapeutic agents include, but are not limited to, a corticosteroid and a LABA, a corticosteroid and a LAMA, a corticosteroid, a LABA and a LAMA, and a corticosteroid and a MABA.

In some embodiments, the respirable dry particles and respirable dry powders can contain an agent that disrupts and/or disperses biofilms. Suitable examples of agents to promote disruption and/or dispersion of biofilms include specific amino acid stereoisomers, e.g., D-leucine, D-methionine, D-tyrosine, D-tryptophan, and the like. (Kolodkin-Gal, I., D. Romero, et al. "D-amino acids trigger biofilm disassembly." Science 328(5978): 627-629.) For example, all or a portion of the leucine in the dry powders described herein which contain leucine can be D-leucine.

Examples of suitable mucoactive or mucolytic agents include MUC5AC and MUC5B mucins, DNase, N-acetylcysteine (NAC), cysteine, nacystelyn, dornase alfa, gelsolin, heparin, heparin sulfate, P2Y2 agonists (e.g. UTP, INS365), nedocromil sodium, hypertonic saline, and mannitol.

Suitable surfactants include L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, and alkylated sugars.

If desired, the respirable dry particles and respirable dry powders can contain an antibiotic. The antibiotic can be suitable for treating any desired bacterial infection. The respirable dry particles and respirable dry powders that contain an antibiotic can be used to reduce the spread of infection, either within a patient or from patient to patient. For example, the respirable dry particles and respirable dry powders for treating bacterial pneumonia or VAT, can further comprise an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-mycobacterium antibiotics and the like.

If desired, the respirable dry particles and respirable dry powders can contain an agent for treating infections with mycobacteria, such as *Mycobacterium tuberculosis*. Suitable agents for treating infections with mycobacteria (e.g., *M. tuberculosis*) include an aminoglycoside (e.g. capreomycin, kanamycin, streptomycin), a fluoroquinolone (e.g. ciprofloxacin, levofloxacin, moxifloxacin), isozianid and isozianid analogs (e.g. ethionamide), aminosalicylate, cycloserine, diarylquinoline, ethambutol, pyrazinamide, protionamide, rifampin, and the like.

If desired, the respirable dry particles and respirable dry powders can contain a suitable antiviral agent, such as oseltamivir, zanamavir, amantidine, rimantadine, ribavirin, gancyclovir, valgancyclovir, foscavir, Cytogam® (Cytomegalovirus Immune Globulin), pleconaril, rupintrivir, palivizumab, motavizumab, cytarabine, docosanol, denotivir, cidofovir, and acyclovir. The respirable dry particles and respirable dry powders can contain a suitable anti-influenza agent, such as zanamivir, oseltamivir, amantadine, or rimantadine.

Suitable antihistamines include clemastine, asalastine, loratadine, fexofenadine and the like.

Suitable cough suppressants include benzonatate, benproperine, clobutinal, diphenhydramine, dextromethorphan, dibunate, fedrilate, glaucine, oxalamine, piperidione, opiods such as codeine and the like.

Suitable brochodilators include short-acting $beta_2$ agonists, long-acting $beta_2$ agonists (LABA), long-acting muscarinic anagonists (LAMA), combinations of LABAs and LAMAs, methylxanthines, short-acting anticholinergic agents (may also be referred to as short acting anti-muscarinic), long-acting bronchodilators, and the like.

Another bronchodilator class is Muscarinic Antagonist-Beta2 Agonists (MABA). These are bifunctional molecules that includes a beta-agonist and Muscarinic antagonist (e.g., a M3 muscarinic antagonist), typically connected by a linker.

Suitable short-acting $beta_2$ agonists include albuterol, epinephrine, pirbuterol, levalbuterol, metaproteronol, maxair, and the like. A combination of a short activing $beta_2$ agonist and an anticholinergic is albuterol and ipatropium bromide (Combivent®; Boehringer Ingelheim).

Examples of albuterol sulfate formulations (also called salbutamol) include Inspiryl (AstraZeneca Plc), Salbutamol SANDOZ (Sanofi-Aventis), Asmasal clickhaler (Vectura Group Plc.), Ventolin® (GlaxoSmithKline Plc), Salbutamol GLAND (GlaxoSmithKline Plc), Airomir® (Teva Pharmaceutical Industries Ltd.), ProAir HFA (Teva Pharmaceutical Industries Ltd.), Salamol (Teva Pharmaceutical Industries Ltd.), Ipramol (Teva Pharmaceutical Industries Ltd), Albuterol sulfate TEVA (Teva Pharmaceutical Industries Ltd), and the like. Examples of epinephrine include Epinephine Mist KING (King Pharmaceuticals, Inc.), and the like. Examples of pirbuterol as pirbuterol acetate include Maxair® (Teva Pharmaceutical Industries Ltd.), and the like. Examples of levalbuterol include Xopenex® (Sepracor or Dainippon Sumitomo), and the like. Examples of metaproteronol formulations as metaproteronol sulfate include Alupent® (Boehringer Ingelheim GmbH), and the like.

Suitable LABAs include salmeterol, formoterol and isomers (e.g., arformoterol), clenbuterol, tulobuterol, vilanterol (GSK642444, also referred to Revolair™), indacaterol, carmoterol, isoproterenol, procaterol, bambuterol, milveterol, olodaterol, AZD3199 (AstraZeneca), and the like.

Examples of salmeterol formulations include salmeterol xinafoate as Serevent® (GlaxoSmithKline Plc), salmeterol as Inaspir (Laboratorios Almirall, S.A.), Advair® HFA (GlaxoSmithKline PLC), Advair Diskus® (GlaxoSmithKline PLC, Theravance Inc), Plusvent (Laboratorios Almirall, S.A.), VR315 (Novartis, Vectura Group PLC) and the like. Examples of formoterol and isomers (e.g., arformoterol) include Foster (Chiesi Farmaceutici S.p.A), Atimos (Chiesi Farmaceutici S.p.A, Nycomed Intemaional Management), Flutiform® (Abbott Laboratories, SkyePharma PLC), MFF258 (Novartis AG), Formoterol clickhaler (Vectura Group PLC), Formoterol HFA (SkyePharma PLC), Oxis® (Astrazeneca PLC), Oxis pMDI (Astrazeneca), Foradil® Aerolizer (Novartis, Schering-Plough Corp, Merck), Foradil® Certihaler (Novartis, SkyePharma PLC), Symbicort® (AstraZeneca), VR632 (Novartis AG, Sandoz International GmbH), MFF258 (Merck & Co Inc, Novartis AG), Alvesco® Combo (Nycomed International Management GmbH, Sanofi-Aventis, Sepracor Inc), Mometasone furoate (Schering-Plough Corp), and the like. Examples of clenbuterol include Ventipulmin® (Boehringer Ingelheim), and the like. Examples of tulobuterol include Hokunalin Tape (Abbott Japan Co., Ltd., Maruho Co., Ltd.), and the like. Examples of vilanterol include Revolair™ (GlaxoSmithKline PLC), GSK64244 (GlaxoSmithKline PLC), and the like. Examples of indacaterol include QAB149 (Novartis AG, SkyePharma PLC), QMF149 (Merck & Co Inc) and the like. Examples of carmoterol include CHF4226 (Chiese Farmaceutici S.p.A., Mitsubishi Tanabe Pharma Corporation), CHF5188 (Chiesi Farmaceutici S.p.A), and the like. Examples of isoproterenol sulfate include Aludrin (Boehringer Ingelheim GmbH) and the like. Examples of procaterol include Meptin clickhaler (Vectura Group PLC), and the like. Examples of bambuterol include Bambec (AstraZeneca PLC), and the like. Examples of milveterol include GSK159797C (GlaxoSmithKline PLC), TD3327 (Theravance Inc), and the like. Examples of olodaterol include BI1744CL (Boehringer Ingelheim GmbH) and the like. Other LABAs include Almirall—LAS100977 (Laboratorios Almirall, S.A.), and UK-503590 (Pfizer).

Examples of LAMAs include tiotroprium (Spiriva), trospium chloride, glycopyrrolate, aclidinium, ipratropium, darotropium, and the like.

Examples of tiotroprium formulations include Spiriva® (Boehringer-Ingleheim, Pfizer), and the like. Examples of glycopyrrolate include Robinul® (Wyeth-Ayerst), Robinul® Forte (Wyeth-Ayerst), NVA237 (Novartis), and the like. Examples of aclidinium include Eklira® (Forest Labaoratories, Almirall), and the like. Examples of darotropium include GSK233705 (GlaxoSmithKline PLC). Examples of other LAMAs include BEA2180BR (Boehringer-Ingleheim), Ba 679 BR (Boehringer-Ingleheim), GSK573719 (GlaxoSmithKline PLC), GSK1160724 (GlaxoSmithKline PLC and Theravance), GSK704838 (GlaxoSmithKline PLC), QAT370 (Novartis), QAX028 (Novartis), AZD8683 (AstraZeneca), and TD-4208 (Theravance).

Examples of combinations of LABAs and LAMAs include indacaterol with glycopyrrolate, formoterol with glycopyrrolate, indacaterol with tiotropium, olodaterol and tiotropium, formoterol and tiotropium, vilanterol with a LAMA, and the like. Examples of combinations of formoterol with glycopyrrolate include PT003 (Pearl Therapeutics) and the like. Examples of combinations of olodaterol with tiotropium include BI1744 with Spirva (Boehringer Ingelheim) and the like. Examples of combinations of vilanterol with a LAMA include GSK573719 with GSK642444 (GlaxoSmithKline PLC), and the like. Another example of a LABA with a LAMA is vilanterol with Anoro Ellipta umeclidinium bromide (GlaxoSmithKline PLC and Theravance Inc.)

Examples of combinations of indacaterol with glycopyrrolate include QVA149A (Novartis), and the like.

Examples of methylxanthine include aminophylline, ephedrine, theophylline, oxtriphylline, and the like.

Examples of aminophylline formulations include Aminophylline BOEHRINGER (Boehringer Ingelheim GmbH) and the like. Examples of ephedrine include Bronkaid® (Bayer AG), Broncholate (Sanofi-Aventis), Primatene® (Wyeth), Tedral SA®, Marax (Pfizer Inc) and the like. Examples of theophylline include Euphyllin (Nycomed International Management GmbH), Theo-dur (Pfizer Inc, Teva Pharmacetuical Industries Ltd) and the like. Examples of oxtriphylline include Choledyl SA (Pfizer Inc) and the like.

Examples of short-acting anticholinergic agents include ipratropium bromide, and oxitropium bromide.

Examples of ipratropium bromide formulations include Atrovent®/Apovent/Inpratropio (Boehringer Ingelheim GmbH), Ipramol (Teva Pharmaceutical Industries Ltd) and the like. Examples of oxitropium bromide include Oxivent (Boehringer Ingelheim GmbH), and the like.

Suitable anti-inflammatory agents include leukotriene inhibitors, phosphodiesterase 4 (PDE4) inhibitors, other anti-inflammatory agents, and the like.

Suitable leukotriene inhibitors include montelukast formulations (cystinyl leukotriene inhibitors), masilukast, zafirleukast (leukotriene D4 and E4 receptor inhibitors), pranlukast, zileuton (5-lipoxygenase inhibitors), GSK256066 (GlaxoSmithKline PLC), and the like.

Examples of montelukast (cystinyl leukotriene inhibitor) include Singulair® (Merck & Co Inc), Loratadine, montelukast sodium SCHERING (Schering-Plough Corp), MK0476C (Merck & Co Inc), and the like. Examples of masilukast include MCC847 (AstraZeneca PLC), and the like. Examples of zafirlukast (leukotriene D4 and E4 receptor inhibitor) include Accolate® (AstraZeneca PLC), and the like. Examples of pranlukast include Azlaire (Schering-Plough Corp). Examples of zileuton (5-LO) include Zyflo® (Abbott Laboratories), Zyflo CR® (Abbott Laboratories, SkyePharma PLC), Zileuton ABBOTT LABS (Abbott Laboratories), and the like.

Suitable PDE4 inhibitors include cilomilast, roflumilast, oglemilast, tofimilast, arofylline (Almirall), and the like.

Examples of cilomilast formulations include Ariflo (GlaxoSmithKline PLC), and the like. Examples of roflumilast include Daxas® (Nycomed International Management GmbH, Pfizer Inc), APTA2217 (Mitsubishi Tanabe Pharma Corporation), and the like. Examples of oglemilast include GRC3886 (Forest Laboratories Inc), and the like. Examples of tofimilast include Tofimilast PFIZER INC (Pfizer Inc), and the like.

Other anti-inflammatory agents include omalizumab (anti-IgE immunoglobulin Daiichi Sankyo Company, Limited), Zolair (anti-IgE immunoglobulin, Genentech Inc, Novartis AG, Roche Holding Ltd), Solfa (LTD4 antagonist and phosphodiesterase inhibitor, Takeda Pharmaceutical Company Limited), IL-13 and IL-13 receptor inhibitors (such as AMG-317, MILR1444A, CAT-354, QAX576, IMA-638, Anrukinzumab, IMA-026, MK-6105, DOM-0910, and the like), IL-4 and IL-4 receptor inhibitors (such as Pitrakinra, AER-003, AIR-645, APG-201, DOM-0919, and the like), IL-1 inhibitors such as canakinumab, CRTh2 receptor antagonists such as AZD1981 (CRTh2 receptor antagonist, AstraZeneca), neutrophil elastase inhibitor such as AZD9668 (neutrophil elastase inhibitor, from AstraZeneca), P38 mitogen-activated protein kinases inhibitor, e.g, GW856553X Losmapimod, GSK681323, GSK 856553, and GSK610677 (all P38 kinase inhibitors, GlaxoSmithKline PLC), and PH-797804 (p38 kinase inhibitor; Pfizer), Arofylline LAB ALMIRALL (PDE-4 inhibitor, Laboratorios Almirall, S.A.), ABT761 (5-LO inhibitor, Abbott Laboratories), Zyflo® (5-LO inhibitor, Abbott Laboratories), BT061 (anti-CD4 mAb, Boehringer Ingelheim GmbH), BIBW 2948 BS (map kinase inhibitor), Corus (inhaled lidocaine to decrease eosinophils, Gilead Sciences Inc), Prograft (IL-2-mediated T-cell activation inhibitor, Astellas Pharma), Bimosiamose PFIZER INC (selectin inhibitor, Pfizer Inc), R411 (alpha4beta1/alpha4beta7 integrin antagonist, Roche Holdings Ltd), Tilade® (inflammatory mediator inhibitor, Sanofi-Aventis), Orenica® (T-cell co-stimulation inhibitor, Bristol-Myers Squibb Company), Soliris® (anti-C5, Alexion Pharmaceuticals Inc), Entorken® (Farmacija d.o.o.), Excellair® (Syk kinase siRNA, ZaBeCor Pharmaceuticals, Baxter International Inc), KB003 (anti-GMCSF mAb, KaloBios Pharmaceuticals), Cromolyn sodiums (inhibit release of mast cell mediators): Cromolyn sodium BOEHRINGER (Boehringer Ingelheim GmbH), Cromolyn sodium TEVA (Teva Pharmaceutical Industries Ltd), Intal (Sanofi-Aventis), BI1744CL (oldaterol (beta-2-adrenoceptor antagonist) and tiotropium, Boehringer Ingelheim GmbH), NFkappa-B inhibitors, CXR2 antagaonists, HLE inhibitors, HMG-CoA reductase inhibitors and the like.

Anti-inflammatory agents also include compounds that inhibit/decrease cell signaling by inflammatory molecules like cytokines (e.g., IL-1, IL-4, IL-5, IL-6, IL-9, IL-13, IL-18 IL-25, IFN-α, IFN-β, and others), CC chemokines CCL-1-CCL28 (some of which are also known as, for example, MCP-1, CCL2, RANTES), CXC chemokines CXCL1-CXCL17 (some of which are also know as, for example, IL-8, MIP-2), CXCR2, growth factors (e.g., GM-CSF, NGF, SCF, TGF-β, EGF, VEGF and others) and/or their respective receptors.

Some examples of the aforementioned anti-inflammatory antagonists/inhibitors include ABN912 (MCP-1/CCL2, Novartis AG), AMG761 (CCR4, Amgen Inc), Enbrel® (TNF, Amgen Inc, Wyeth), huMAb OX40L GENENTECH (TNF superfamily, Genentech Inc, AstraZeneca PLC), R4930 (TNF superfamily, Roche Holding Ltd), SB683699/Firategrast (VLA4, GlaxoSmithKline PLC), CNT0148 (TNFalpha, Centocor, Inc, Johnson & Johnson, Schering-Plough Corp); Canakinumab (IL-Obeta, Novartis); Israpafant MITSUBISHI (PAF/IL-5, Mitsubishi Tanabe Pharma Corporation); IL-4 and IL-4 receptor antagonists/inhibitors: AMG317 (Amgen Inc), BAY169996 (Bayer AG), AER-003 (Aerovance), APG-201 (Apogenix); IL-5 and IL-5 receptor antagonists/inhibitors: MEDI563 (AstraZeneca PLC, MedImmune, Inc), Bosatria® (GlaxoSmithKline PLC), Cinquil® (Ception Therapeutic), TMC120B (Mitsubishi Tanabe Pharma Corporation), Bosatria (GlaxoSmithKline PLC), Reslizumab SCHERING (Schering-Plough Corp); MEDI528 (IL-9, AstraZeneca, MedImmune, Inc); IL-13 and IL-13 receptor antagonists/inhibitors: TNX650 GENENTECH (Genentech), CAT-354 (AstraZeneca PLC, MedImmune), AMG-317 (Takeda Pharmaceutical Company Limited), MK6105 (Merck & Co Inc), IMA-026 (Wyeth), IMA-638 Anrukinzumab (Wyeth), MILR1444A/Lebrikizumab (Genentech), QAX576 (Novartis), CNTO-607 (Centocor), MK-6105 (Merck, CSL); Dual IL-4 and IL-13 inhibitors: AIR645/ISIS369645 (ISIS Altair), DOM-0910 (GlaxoSmithKline, Domantis), Pitrakinra/AER001/Aerovant™ (Aerovance Inc), AMG-317 (Amgen), and the like. CXCR2 antagonists include, for example, Reparixin (Dompe S.P.A.), DF2162 (Dompe, S.P.A.), AZ-10397767 (AstraZeneca), SB656933 (GlaxoSmithKline PLC), SB332235 (GlaxoSmithKline PLC), SB468477 (GlaxoSmithKline PLC), and SCH527123 (Shering-Plough Corp).

Suitable steroids include corticosteroids, combinations of corticosteroids and LABAs, combinations of corticosteroids and LAMAs, combinations of corticosteroids, LABAs and LAMAs, and the like. In a preferred aspect of the invention, a corticosteroid is combined with a MABA.

Suitable corticosteroids include budesonide, fluticasone, flunisolide, triamcinolone, beclomethasone, mometasone, ciclesonide, dexamethasone, and the like.

Examples of budesonide formulations include Captisol-Enabled® Budesonide Solution for Nebulization (AstraZeneca PLC), Pulmicort® (AstraZeneca PLC), Pulmicort® Flexhaler (AstraZeneca Plc), Pulmicort® HFA-MDI (Astra-Zeneca PLC), Pulmicort Respules® (AstraZeneca PLC), Inflammide (Boehringer Ingelheim GmbH), Pulmicort® HFA-MDI (SkyePharma PLC), Unit Dose Budesonide ASTRAZENECA (AstraZeneca PLC), Budesonide Modulite (Chiesi Farmaceutici S.p.A), CHF5188 (Chiesi Farmaceutici S.p.A), Budesonide ABBOTT LABS (Abbott Laboratories), Budesonide clickhaler (Vestura Group PLC), Miflonide (Novartis AG), Xavin (Teva Pharmaceutical Industries Ltd.), Budesonide TEVA (Teva Pharmaceutical Industries Ltd.), Symbicort® (AstraZeneca K.K., AstraZeneca PLC), VR632 (Novartis AG, Sandoz International GmbH), and the like.

Examples of fluticasone propionate formulations include Flixotide Evohaler (GlaxoSmithKline PLC), Flixotide Nebules (GlaxoSmithKline Plc), Flovent® (GlaxoSmithKline Plc), Flovent® Diskus (GlaxoSmithKline PLC), Flovent® HFA (GlaxoSmithKline PLC), Flovent® Rotadisk (GlaxoSmithKline PLC), Advair® HFA (GlaxoSmithKline PLC, Theravance Inc), Advair Diskus® (GlaxoSmithKline PLC, Theravance Inc.), VR315 (Novartis AG, Vectura Group PLC, Sandoz International GmbH), and the like. Other formulations of fluticasone include fluticasone as Flusonal (Laboratorios Almirall, S.A.), fluticasone furoate as GW685698 (GlaxoSmithKline PLC, Thervance Inc.), Plusvent (Laboratorios Almirall, S.A.), Flutiform® (Abbott Laboratories, SkyePharma PLC), and the like.

Examples of flunisolide formulations include Aerobid® (Forest Laboratories Inc), Aerospan® (Forest Laboratories Inc), and the like. Examples of triamcinolone include Triamcinolone ABBOTT LABS (Abbott Laboratories), Azmacort® (Abbott Laboratories, Sanofi-Aventis), and the like. Examples of beclomethasone dipropionate include Beclovent (GlaxoSmithKline PLC), QVAR® (Johnson & Johnson, Schering-Plough Corp, Teva Pharmacetucial Industries Ltd), Asmabec clickhaler (Vectura Group PLC), Beclomethasone TEVA (Teva Pharmaceutical Industries Ltd), Vanceril (Schering-Plough Corp), BDP Modulite (Chiesi Farmaceutici S.p.A.), Clenil (Chiesi Farmaceutici S.p.A), Beclomethasone dipropionate TEVA (Teva Pharmaceutical Industries Ltd), and the like. Examples of mometasone include QAB149 Mometasone furoate (Schering-Plough Corp), QMF149 (Novartis AG), Fomoterol fumarate, mometoasone furoate (Schering-Plough Corp), MFF258 (Novartis AG, Merck & Co Inc), Asmanex® Twisthaler (Schering-Plough Corp), and the like. Examples of cirlesonide include Alvesco® (Nycomed International Management GmbH, Sepracor, Sanofi-Aventis, Tejin Pharma Limited), Alvesco® Combo (Nycomed International Management GmbH, Sanofi-Aventis), Alvesco® HFA (Nycomed Intenational Management GmbH, Sepracor Inc), and the like. Examples of dexamethasone include DexPak® (Merck), Decadron® (Merck), Adrenocot, CPC-Cort-D, Decaject-10, Solurex and the like. Other corticosteroids include Etiprednol dicloacetate TEVA (Teva Pharmaceutical Industries Ltd), and the like.

Other corticosteroids include TPI 1020 (Topigen Pharmaceuticals), GSK685698 also know as fluticasone furoate (GlaxoSmithKline PLC), and GSK870086 (glucocorticoid agonist; GlaxoSmithKline PLC)

Combinations of corticosteroids and LABAs include salmeterol with fluticasone, formoterol with budesonide, formoterol with fluticasone, formoterol with mometasone, indacaterol with mometasone, vilanterol with fluticasone furoate, formoterol and ciclesonide, and the like.

Examples of salmeterol with fluticasone include Plusvent (Laboratorios Almirall, S.A.), Advair® HFA (GlaxoSmithKline PLC), Advair® Diskus (GlaxoSmithKline PLC, Theravance Inc), VR315 (Novartis AG, Vectura Group PLC, Sandoz International GmbH) and the like. Examples of formoterol with budesonide include Symbicort® (AstraZeneca PLC), VR632 (Novartis AG, Vectura Group PLC), and the like. Examples of vilanterol with fluticasone include GSK642444 with fluticasone and the like. Examples of formoterol with fluticasone include Flutiform® (Abbott Laboratories, SkyePharma PLC), and the like. Examples of formoterol with mometasone include Dulera®/MFF258 (Novartis AG, Merck & Co Inc), and the like. Examples of indacaterol with mometasone include QAB149 Mometasone furoate (Schering-Plough Corp), QMF149 (Novartis AG), and the like. Combinations of corticosteroids with LAMAs include fluticasone with tiotropium, budesonide with tiotropium, mometasone with tiotropium, salmeterol with tiotropium, formoterol with tiotropium, indacaterol with tiotropium, vilanterol with tiotropium, and the like. Examples of vilanterol with fluticasone furoate include Revolair® (GSK642444 and GSK685698; GlaxoSmithKline PLC), and the like. Examples of formoterol and ciclesonide are formoterol and ciclesonide (Forest/Nycomed), and the like. Combinations of corticosteroids with LAMAs and LABAs include, for example, fluticasone with salmeterol and tiotropium.

Other anti-asthma molecules include: ARD111421 (VIP agonist, AstraZeneca PLC), AVE0547 (anti-inflammatory, Sanofi-Aventis), AVE0675 (TLR agonist, Pfizer, Sanofi-Aventis), AVE0950 (Syk inhibitor, Sanofi-Aventis), AVE5883 (NK1/NK2 antagonist, Sanofi-Aventis), AVE8923 (tryptase beta inhibitor, Sanofi-Aventis), CGS21680 (adenosine A2A receptor agonist, Novartis AG), ATL844 (A2B receptor antagonist, Novartis AG), BAY443428 (tryptase inhibitor, Bayer AG), CHF5407 (M3 receptor inhibitor, Chiesi Farmaceutici S.p.A.), CPLA2 Inhibitor WYETH (CPLA2 inhibitor, Wyeth), IMA-638 (IL-13 antagonist, Wyeth), LAS100977 (LABA, Laboratorios Almirall, S.A.), MABA (M3 and beta-2 receptor antagonist, Chiesi Farmaceutici S.p.A), R1671 (mAb, Roche Holding Ltd), CS003 (Neurokinin receptor antagonist, Daiichi Sankyo Company, Limited), DPC168 (CCR antagonist, Bristol-Myers Squibb), E26 (anti-IgE, Genentech Inc), HAE1 (Genentech), IgE inhibitor AMGEN (Amgen Inc), AMG853 (CRTH2 and D2 receptor antagonist, Amgen), IPL576092 (LSAID, Sanofi-Aventis), EPI2010 (antisense adenosine 1, Chiesi Farmaceutici S.p.A.), CHF5480 (PDE-4 inhibitor, Chiesi Farmaceutici S.p.A.), K104204 (corticosteroid, Abbott Laboratories), SVT47060 (Laboratorios Salvat, S.A.), VML530 (leukotriene synthesis inhibitor, Abbott Laboratories), LAS35201 (M3 receptor antagonist, Laboratorios Almirall, S.A.), MCC847 (D4 receptor antagonist, Mitsubishi Tanabe Pharma Corporation), MEM1414 (PDE-4 inhibitor, Roche), TA270 (5-LO inhibitor, Chugai Pharmaceutical Co Ltd), TAK661 (eosinophil chemotaxis inhibitor, Takeda Pharmaceutical Company Limited), TBC4746 (VLA-4 antagonist, Schering-Plough Corp), VR694 (Vectura Group PLC), PLD177 (steroid, Vectura Group PLC), K103219 (corticosteroid+LABA, Abbott Laboratories), AMG009 (Amgen Inc), AMG853 (D2 receptor antagonist, Amgen Inc);

AstraZeneca PLC: AZD1744 (CCR3/histamine-1 receptor antagonist, AZD1419 (TLR9 agonist), Mast Cell inhibitor ASTRAZENECA, AZD3778 (CCR antagonist), DSP3025 (TLR7 agonist), AZD1981 (CRTh2 receptor antagonist), AZD5985 (CRTh2 antagonist), AZD8075 (CRTh2 antagonist), AZD1678, AZD2098, AZD2392, AZD3825 AZD8848, AZD9215, ZD2138 (5-LO inhibitor), AZD3199 (LABA); AZD2423 (CCR2b antagonist); AZD5069 (CXCR2 antagonist); AZD5423 (Selective glucocorticoid receptor agonist (SEGRA)); AZD7594; AZD2115.

GlaxoSmithKline PLC: GW328267 (adenosine A2 receptor agonist), GW559090 (alpha4 integrin antagonist), GSK679586 (mAb), GSK597901 (adrenergic beta2 agonist), AM103 (5-LO inhibitor), GSK256006 (PDE4 inhibitor), GSK256066, GW842470 (PDE-4 inhibitor), GSK870086 (glucocorticoid agonist), GSK159802 (LABA), GSK256066 (PDE-4 inhibitor), GSK642444 (vilanterol, LABA, adrenergic beta2 agonist), GSK685698 (ICS, fluticasone furoate), Revolair® (GSK64244/vilanterol and GSK685698/fluticasone furoate), GSK799943 (corticosteroid), GSK573719 (mAchR antagonist), GSK2245840 (SIRT1 Activator); Mepolizumab (anti-IL-5 mAb); and GSK573719 (LAMA), and GSK573719 (LAMA) and vilanterol (LABA);

Pfizer Inc: PF3526299, PF3893787, PF4191834 (FLAP antagonist), PF610355 (adrenergic beta2 agonist), CP664511 (alpha4beta1/VCAM-1 interaction inhibitor), CP609643 (inhibitor of alpha4beta1/VCAM-1 interactions), CP690550 (JAK3 inhibitor), SAR21609 (TLR9 agonist), AVE7279 (Th1 switching), TBC4746 (VLA-4 antagonist); R343 (IgE receptor signaling inhibitor), SEP42960 (adenosine A3 antagonist);

Sanofi-Aventis: MLN6095 (CrTH2 inhibitor), SAR137272 (A3 antagonist), SAR21609 (TLR9 agonist), SAR389644 (DP1 receptor antagonist), SAR398171 (CRTH2 antagonist), SSR161421 (adenosine A3 receptor antagonist);

Merck & Co Inc: MK0633, MK0633, MK0591 (5-LO inhibitor), MK886 (leukotriene inhibitor), BI01211 (VLA-4 antagonist); Novartis AG: QAE397 (long-acting corticosteroid), QAK423, QAN747, QAP642 (CCR3 antagonist), QAX935 (TLR9 agonist), NVA237 (LAMA).

The therapeutic agent can also be selected from the group consisting of transient receptor potential (TRP) channel agonists. In certain embodiments, the TRP agonist is a TRPC, TRPV, TRPM and/or TRPA1 subfamily agonist. In some embodiments, the TRP channel agonist is selected from the group consisting of TRPV2, TRPV3, TRPV4, TRPC6, TRPM6, and/or TRPA1 agonist. Suitable TRP channel agonists may be selected from the group consisting of allyl isothiocyanate (AITC), benyzl isothiocyanate (BITC), phenyl isothiocyanate, isopropyl isothiocyanate, methyl isothiocyanate, diallyl disulfide, acrolein (2-propenal), disulfiram (Antabuse®), farnesyl thiosalicylic acid (FTS), farnesyl thioacetic acid (FTA), chlodantoin (Sporostacin®, topical fungicidal), (15-d-PGJ2), 5,8,11,14 eicosatetraynoic acid (ETYA), dibenzoazepine, mefenamic acid, fluribiprofen, keoprofen, diclofenac, indomethacin, SC alkyne (SCA), pentenal, mustard oil alkyne (MOA), iodoacetamine, iodoacetamide alkyne, (2-aminoethyl) methanethiosulphonate (MTSEA), 4-hydroxy-2-noneal (HNE), 4-hydroxy xexenal (HHE), 2-chlorobenzalmalononitrile, N-chloro tosylamide (chloramine-T), formaldehyde, isoflurane, isovelleral, hydrogen peroxide, URB597, thiosulfinate, Allicin (a specific thiosulfinate), flufenamic acid, niflumic acid, carvacrol, eugenol, menthol, gingerol, icilin, methyl salicylate, arachidonic acid, cinnemaldehyde, super sinnemaldehyde, tetrahydrocannabinol (THC or $\Delta^9$-THC), cannabidiol (CBD), cannabichromene (CBC), cannabigerol (CBG), THC acid (THC-A), CBD acid (CBD-A), Compound 1 (AMG5445), 4-methyl-N-[2,2,2-trichloro-1-(4-chlorophenylsulfanyl) ethyl]benzamide, N-[2,2,2-trichloro-1-(4-chlorophenylsulfanyl)ethyl]acetamid, AMG9090, AMG5445, 1-oleoyl-2-acetyl-sn-glycerol (OAG), carbachol, diacylglycerol (DAG), 1,2-Didecanoylglycerol, flufenamate/flufenamic acid, niflumate/niflumic acid, hyperforin, 2-aminoethoxydiphenyl borate (2-APB), diphenylborinic anhydride (DPBA), delta-9-tetrahydrocannabinol ($\Delta^9$-THC or THC), cannabiniol (CBN), 2-APB, 0-1821, 11-hydroxy-$\Delta$9-tetrahydrocannabinol, nabilone, CP55940, HU-210, HU-211/dexanabinol, HU-331, HU-308, JWH-015, WIN55, 212-2, 2-Arachidonoylglycerol (2-AG), Arvil, PEA, AM404, 0-1918, JWH-133, incensole, incensole acetate, menthol, eugenol, dihydrocarveol, carveol, thymol, vanillin, ethyl vanillin, cinnemaldehyde, 2 aminoethoxydiphenyl borate (2-APB), diphenylamine (DPA), diphenylborinic anhydride (DPBA), camphor, (+)-bomeol, (−)-isopinocampheol, (−)-fenchone, (−)-trans-pinocarveol, isoborneol, (+)-camphorquinone, (−)-α-thujone, α-pinene oxide, 1,8-cineole/eucalyptol, 6-butyl-m-cresol, carvacrol, p-sylenol, kreosol, propofol, p-cymene, (−)-isoppulegol, (−)-carvone, (+)-dihydrocarvone, (−)-menthone, (+)-linalool, geraniol, 1-isopropyl-4-methylbicyclo[3.1.0]hexan-4-ol, 4αPDD, GSK1016790A, 5'6'Epoxyeicosatrienoic (5'6'-EET), 8'9'Epoxyeicosatrienoic (8'9'-EET), APP44-1, RN1747, Formulation Ib WO200602909, Formulation IIb WO200602909, Formulation IIc WO200602929, Formulation IId WO200602929, Formulation IIIb WO200602929, Formulation IIIc WO200602929, arachidonic acid (AA), 12-O-Tetradecanoylphorbol-13-acetate (TPA)/phorbol 12-myristate 13-acetate (PMA), bisandrographalide (BAA), incensole, incensole acetate, Compound IX WO2010015965, Compound X WO2010015965, Compound XI WO2010015965, Compound XII WO2010015965, WO2009004071, WO2006038070, WO2008065666, Formula VII WO2010015965, Formula IV WO2010015965, dibenzoazepine, dibenzooxazepine, Formula I WO2009071631, N-{(1S)-1-[({(4R)-1-[(4-chlorophenyl)sulfonyl]-3-oxohexahydro-Hazepin-4-yl}amino)carbonyl]-3-methylbutyl}-1-benzothiophen-2-carboxamide, N-{(1S)-1-[({(4R)-1-[(4-fluorophenyl)sulfonyl]-3-oxohexahydro-1H-azepin-4-yl}amino)carbonyl]-3-methylbutyl}-1-benzothiophen-2-carboxamide, N-{(1S)-1-[({(4R)-1-[(2-cyanophenyl)sulfonyl]-3-oxohexahydro-1H-azepin-4-yl}amino)carbonyl]-3-methylbutyl}-1-methyl-1H-indole-2-carboxamide, and N-{(1S)-1-[({(4R)-1-[(2-cyanophenyl)sulfonyl]hexahydro-1H-azepin-4-yl}amino)carbonyl]-3-methylbutyl}-1-methyl-1H-indole-2-carboxamide.

Suitable expectorants include guaifenesin, guaiacolculfonate, ammonium chloride, potassium iodide, tyloxapol, antimony pentasulfide and the like.

Suitable vaccines include nasally inhaled influenza vaccines and the like.

Suitable macromolecules include proteins and large peptides, polysaccharides and oligosaccharides, DNA and RNA nucleic acid molecules and their analogs having therapeutic, prophylactic or diagnostic activities. Proteins can include growth factors, hormones, cytokines (e.g., chemokines), and antibodies. As used herein, antibodies can include: all types of immunoglobulins, e.g. IgG, IgM, IgA, IgE, IgD, etc., from any source, e.g. human, rodent, rabbit, cow, sheep, pig, dog, other mammals, chicken, other avian, aquatic animal species etc., monoclonal and polyclonal antibodies, single chain antibodies (including IgNAR (single-chain antibodies derived from sharks)), chimeric antibodies, bifunctional/bispecific antibodies, humanized antibodies, human antibodies, and complementary determining region (CDR)-grafted antibodies, that are specific for the target protein or fragments thereof, and also include antibody fragments, including Fab, Fab', F(ab')2, scFv, Fv, camelbodies, microantibodies, nanobodies, and small-modular immunopharmaceuticals (SMIPs). Nucleic acid molecules include DNA, e.g. encoding genes or gene fragments, or RNA, including mRNA, antisense molecules, such as antisense RNA, RNA molecules involved in RNA interference (RNAi), such as microRNA (miRNA), small interfering RNA (siRNA) and small hairpin RNA (shRNA), ribozymes or other molecules capable of inhibiting transcription and/or translation. Preferred macromolecules have a molecular weight of at least 800 Da, at least 3000 Da or at least 5000 Da.

In preferred embodiments, the respirable dry powder or respirable dry particle comprises a therapeutic antibody. In certain preferred embodiments, the antibody is a monoclonal antibody. In certain preferred embodiments, the antibody is a single chain antibody, a chimeric antibody, a bifunctional/bispecific antibody, a humanized antibody, or a combination thereof. In preferred embodiments, the antibody is selected from the group consisting of: monoclonal antibodies, e.g. Abciximab (ReoPro®, chimeric), Adalimumab (Humira®, human), Alemtuzumab (Campath®, humanized), Basiliximab (Simulect®, chimeric), Belimumab (Benlysta®, human), Bevacizumab (Avastin®, humanized), Brentuximab vedotin (Adcetris®, chimeric), Canakinumab (Ilaris®, human), Cetuximab (Erbitux®, chimeric), Certolizumab pegol (Cimzia®, humanized), Daclizumab (Zenapax®, humanized), Denosumab (Prolia®, Xgeva®, human), Eculizumab (Soliris®, humanized), Efalizumab (Raptiva®, humanized), Gemtuzumab (Mylotarg®, humanized), Golimumab (Simponi®, human), Ibritumomab tiuxetan (Zevalin®, murin), Infliximab (Remicade®, chimeric), Ipilimumab (MDX-101) (Yervoy®, human), Muromonab-CD3 (Orthoclone OKT3, murine), Natalizumab (Tysabri®, humanized), Ofatumumab (Arzerra®, human), Omalizumab (Xolair®, humanized), Palivizumab (Synagis®, humanized), Panitumumab (Vectibix®, human), Ranibizumab (Lucentis®, humanized), Rituximab (Rituxan®, Mabthera®, chimeric), Tocilizumab (or Atlizumab) (Actemra® and RoActemra®, humanized), Tositumomab (Bexxar®, murine), Trastuzumab (Herceptin®, humanized), and bispecific antibodies, e.g. catumaxomab (Removab®, rat-mouse hybrid monoclonal antibody).

Selected macromolecule therapeutic agents for systemic applications include, but are not limited to: Ventavis® (Iloprost), Calcitonin, Erythropoietin (EPO), Factor IX, Granulocyte Colony Stimulating Factor (G-CSF), Granulocyte Macrophage Colony, Stimulating Factor (GM-CSF), Growth Hormone, Insulin, TGF-beta, Interferon Alpha, Interferon Beta, Interferon Gamma, Luteinizing Hormone Releasing Hormone (LHRH), follicle stimulating hormone (FSH), Ciliary Neurotrophic Factor, Growth Hormone Releasing Factor (GRF), Insulin-Like Growth Factor, Insulinotropin, Interleukin-1 Receptor Antagonist, Interleukin-3, Interleukin-4, Interleukin-6, Macrophage Colony Stimulating Factor (M-CSF), Thymosin Alpha 1, IIb/IIIa Inhibitor, Alpha-1 Antitrypsin, Anti-RSV Antibody, palivizumab, motavizumab, and ALN-RSV, Cystic Fibrosis Transmembrane Regulator (CFTR) Gene, Deoxyribonuclease (DNase), Heparin, Bactericidal/Permeability Increasing Protein (BPI), Anti-Cytomegalovirus (CMV) Antibody, Interleukin-1 Receptor Antagonist, and the like, alpha-defensins (e.g. human neutrophil proteins (HNPs): HNP1, 2, 3, and 4; human defensins 5 and 6 (HD5 and HD6)), beta-defensins (HBD1, 2, 3, and 4), or Θ-defensins/retrocyclins, GLP-1 analogs (liraglutide, exenatide, etc.), Domain antibodies (dAbs), Pramlintide acetate (Symlin), Leptin analogs, Synagis (palivizumab, MedImmune) and cisplatin. In certain preferred embodiments, the respirable dry powder or respirable dry particle comprises a macromolecule involved in intra- or inter-cellular signaling, such as a growth factor, a cytokine, a chemokine or a hormone. In preferred embodiments, the respirable dry powder or respirable dry particle comprises a hormone. In certain preferred embodiments, the hormone is insulin.

Selected therapeutics helpful for chronic maintenance of CF include antibiotics/macrolide antibiotics, bronchodilators, inhaled LABAs, and agents to promote airway secretion clearance. Suitable examples of antibiotics/macrolide antibiotics include tobramycin, azithromycin, ciprofloxacin, colistin, aztreonam and the like. Another exemplary antibiotic/macrolide is levofloxacin. Suitable examples of bronchodilators include inhaled short-acting $bet_{a2}$ agonists such as albuterol, and the like. Suitable examples of inhaled LABAs include salmeterol, formoterol, and the like. Suitable examples of agents to promote airway secretion clearance include Pulmozyme (dornase alfa, Genentech) hypertonic saline, DNase, heparin, and the like. Selected therapeutics helpful for the prevention and/or treatment of CF include VX-770 (Vertex Pharmaceuticals) and amiloride.

Selected therapeutics helpful for the treatment of idiopathic pulmonary fibrosis include Metelimumab (CAT-192) (TGF-beta1 mAb inhibitor, Genzyme), Aerovant™ (AER001, pitrakinra) (Dual IL-13, IL-4 protein antagonist, Aerovance), Aeroderm™ (PEGylated Aerovant, Aerovance), microRNA, RNAi, and the like.

If desired, the respirable salt particles and respirable dry powders can contain Meropenem (an anti infective therapeutic, for example, a bacterial), long acting corticosteroids (LAICS), the class of therapeutics known as MABAs (Bifunctional Muscarinic Antagonist-Beta2 Agonists), beclomethasone dipropionate (BDP)/formoterol (combination formulation), caffeine citrate (a citrate salt of caffeine) for short-term treatment of apnea of prematurity (lack of breathing in premature infants), surfactants for treatment of neonatal respiratory distress syndrome (RDS) (difficulty to breathe), the class of therapeutics know as caspase inhibitors (for example, for the treatment of Neonatal Brain injury), and the class of therapeutics known as Gamma secretase Modulators (for example, for the treatment of Alzheimer disease, etc.)

Examples of MABAs are AZD 2115 (AstraZeneca), GSK961081 (GlaxoSmithKline), and LAS190792 (Almirall). Other examples are PF4348235 (Pfizer) and PF3429281 (Pfizer).

In preferred embodiments, the respirable dry powder or respirable dry particle comprises an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-mycobacterium antibiotics, tobramycin, azithromycin, ciprofloxacin, colistin, and the like. In a preferred embodiment, the respirable dry powder or respirable dry particle comprises levofloxacin. In another preferred embodiment, the respirable dry powder or respirable dry particle comprises aztreonam or a pharmaceutically acceptable salt thereof (i.e., Cayston®). In a further preferred embodiment, the respirable dry powder or respirable dry particle does not comprise tobramycin. In another embodiment, the respirable dry powder or respirable dry particle does not comprise levofloxacin. In another embodiment, the respirable dry powder or respirable dry particle does not comprise Cayston®.

In preferred embodiments, the respirable dry powder or respirable dry particle comprises a LABA, such as salmeterol, formoterol and isomers (e.g., arformoterol), clenbuterol, tulobuterol, vilanterol (Revolair™), indacaterol, carmoterol, isoproterenol, procaterol, bambuterol, milveterol, and the like. In a further preferred embodiment, the respirable dry powder or respirable dry particle comprises formoterol. In a further preferred embodiment, the respirable dry powder or respirable dry particle comprises salmeterol. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

In preferred embodiments, the respirable dry powder or respirable dry particle comprises a LAMA, such as tiotropium, glycopyrrolate, aclidinium, ipratropium and the like. In a further preferred embodiment, the respirable dry powder or respirable dry particle comprises tiotropium.

In preferred embodiments, the respirable dry powder or respirable dry particle comprises a corticosteroid, such as budesonide, fluticasone, flunisolide, triamcinolone, beclomethasone, mometasone, ciclesonide, dexamethasone, and the like. In a further preferred embodiment, the respirable dry powder or respirable dry particle comprises fluticasone.

In preferred embodiments, the respirable dry powder or respirable dry particle comprises a combination of two or more of the following; a LABA, a LAMA, and a corticosteroid. In a further preferred embodiment, the respirable dry powder or respirable dry particle comprises fluticasone and salmeterol. In a further preferred embodiment, the respirable dry powder or respirable dry particle comprises fluticasone, salmeterol, and tiotropium.

When an additional therapeutic agent is administered to a patient with a dry powder or dry particles disclosed herein, the agent and the dry powder or dry particles are administered to provide overlap of the therapeutic effect of the additional therapeutic agent with the administration of the dry powder or dry particles. For example, a LABA such as formoterol, or a short-acting beta agonist such as albuterol can be administered to the patient before a dry powder or dry particle, as described herein, is administered.

In preferred embodiments, the respirable dry powder or respirable dry particle does not comprise a surfactant, such as L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, or alkylated sugars.

The therapeutic agents mentioned herein are listed only for illustrative purposes, and it must be emphasized that any given therapeutic agent identified by a structural or functional class may be replaced with another therapeutic agent of the same structural or functional class.

Excipients

If desired, the respirable dry particles described herein can include a physiologically or pharmaceutically acceptable excipient. For example, a pharmaceutically-acceptable excipient includes any of the standard carbohydrates, sugar alcohols, and amino acids that are known in the art to be useful excipients for inhalation therapy, either alone or in any desired combination. These excipients are generally relatively free-flowing particulates, do not thicken or polymerize upon contact with water, are toxicologically innocuous when inhaled as a dispersed powder and do not significantly interact with the therapeutic agent in a manner that adversely affects the desired physiological action. Carbohydrate excipients that are useful in this regard include the mono- and polysaccharides. Representative monosaccharides include carbohydrate excipients such as dextrose (anhydrous and the monohydrate; also referred to as glucose and glucose monohydrate), galactose, mannitol, D-mannose, sorbose and the like. Representative disaccharides include lactose, maltose, sucrose, trehalose and the like. Representative trisaccharides include raffinose and the like. Other carbohydrate excipients include maltodextrin and cyclodextrins, such as 2-hydroxypropyl-beta-cyclodextrin can be used as desired.

Representative sugar alcohols include mannitol, sorbitol and the like.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cysteine, glycine, glutamine, serine, threonine, and tyrosine. Representative examples of polar, positively charged amino acids include arginine, histidine and lysine. Representative examples of negatively charged amino acids include aspartic acid and glutamic acid. These amino acids can be in the D or L optical isomer form, or a mixture of the two forms. These amino acids are generally available from commercial sources that provide pharmaceutical-grade products such as the Aldrich Chemical Company, Inc., Milwaukee, Wis. or Sigma Chemical Company, St. Louis, Mo.

For dry particles, one or more amino acid excipients, such as the hydrophobic amino acid leucine, one or more carbohydrate excipients, such as maltodextrin and trehalose, and one or more preferred sugar alcohol, such as mannitol, and a mixture thereof can be present in the dry particles in an amount of about 99% or less by weight of respirable dry particles. For example, one or more excipients may be present in an amount of about 1% to about 20% by weight of the dry particles, greater than about 20% to about 60% by weight of the dry particles, or greater than about 60% to about 99% by weight of the dry particles. For example, the dry particles can include one or more excipients in an amount of between about 1% and about 5%, greater than about 5% to about 10%, greater than about 10% to about 15%, greater than about 15% to about 20%, greater than about 20% to about 30%, greater than about 30% to about 40%, greater than about 40% to about 50%, greater than about 50% to about 60%, greater than about 60% to about 70%, greater than about 70% to about 80%, greater than about 80% to about 90%, or greater than about 90% to 95%, greater than about 95% to about 99%, or greater than about 99% to about 100%, all percentages are by weight of the dry particles.

Alternatively, the excipient may be present in an amount less than about 90%, in an amount less than about 80%, in an amount less than about 70%, in an amount less than about 60%, in an amount less than about 50%, in an amount less than about 40%, in an amount less than about 35%, in an amount less than about 30%, in an amount less than about 25%, in an amount less than about 20%, in an amount less than about 17.5%, in an amount less than about 15%, in an amount less than about 12.5%, in an amount less than about 10%, in an amount less than about 8%, in an amount less than about 6%, in an amount less than about 5%, in an amount less than about 4%, in an amount less than about 3%, in an amount less than about 2%, or in an amount less than about 1%, all percentages are by weight of the dry particles.

In some preferred aspects, the dry particles contain an excipient selected from leucine, maltodextrin, mannitol and any combination thereof. In particular embodiments, the excipient is leucine, maltodextrin, or mannitol.

Coatings

In some aspects, the respirable dry particles and dry powders is contained in a capsule. The capsule can be a hard or soft gelatin capsule, a starch capsule, or a cellulosic capsule. Such dosage forms can further be coated with, for example, a seal coating, an enteric coating, a film coating, a barrier coating, or a compressed coating. As a result, the capsule can provide a layer of protection from moisture ingress, light degradation, or the like.

Solubility and Molecular Weight

Solubility of therapeutic agents and excipients: The formulation may contain components that are hydrophobic or hydrophilic.

A "hydrophobic" component describes a compound that that has a log P value greater than 1.0, where P is the partition coefficient of the compound between octanol and water. (See, for example, Exploring QSAR, Fundamentals and Applications in Chemistry and Biology, by Corwin Hansch and Albert Leo, 1995, American Chemical Society.) Typically, a hydrophobic component will have solubility below 5 mg/ml, usually below 1 mg/ml, or will have an aqueous solubility of in electronically neutral, non-ionized form, of generally less than 1% by weight, and typically less than 0.1% or 0.01% by weight.

Exemplary hydrophobic drugs include certain steroids, such as budesonide, testosterone, progesterone, estrogen, flunisolide, triamcinolone, beclomethasone, betamethasone, dexamethasone, fluticasone, methylprednisolone, prednisone, hydrocortisone, and the like; certain peptides, such as cyclosporin cyclic peptide, retinoids, such as all-cis retinoic acid, 13-trans retinoic acid, and other vitamin A and beta carotene derivatives; vitamins D, E, and K and water insoluble precursors and derivatives thereof; prostagladins and leukotrienes and their activators and inhibitors including prostacyclin (epoprostanol), and prostaglandins $E_1$, $E_2$; tetrahydrocannabinol; lung surfactant lipids; lipid soluble antioxidants; hydrophobic antibiotics and chemotherapeutic drugs such as amphotericin B and adriamycin and the like.

A "hydrophilic" component describes a compound that has a log P value less than 1.0, where P is the partition coefficient of the compound between octanol and water. (See, for example, Exploring QSAR, Fundamentals and Applications in Chemistry and Biology, by Corwin Hansch and Albert Leo, 1995, American Chemical Society.) Typical aqueous solubilities of hydrophilic components will be greater than 5 mg/ml, usually greater than 50 mg/ml, often greater than 100 mg/ml and often much higher, or of apparent water solubilities of at least 0.1% by weight, and typically at least 1% by weight. Exemplary hydrophilic excipients include carbohydrates and other materials selected from the group consisting of lactose, sodium citrate, mannitol, povidone, pectin, citric acid, sodium chloride, water soluble polymers, and the like.

Of course, certain hydrophobic therapeutic agents may be readily converted to and are commercially available in hydrophilic form, e.g., by ionizing a non-ionized therapeutic agent so as to form a pharmaceutically acceptable, pharmacologically active salt. Conversely, certain hydrophilic therapeutic agents may be readily converted to and are commercially available in hydrophobic form, e.g., by neutralization, esterification, and the like.

The solubility of selected active therapeutic agents can be found, for example in PCT Publication No. WO/2004/062643 "Dry dispersions." The following is a listing of therapeutic agents that are slightly soluble, sparingly soluble or insoluble in water. The format is (1) Drug Name, (2) Therapeutic Class, and (3) Solubility In Water. Alprazolam CNS Insoluble; Amiodarone Cardiovascular Very Slightly; Amlodipine Cardiovascular Slightly; Astemizol Respiratory Insoluble; Atenolol Cardiovascular Slightly; Azathioprine Anticancer Insoluble; Azelastine Respiratory Insoluble; Beclomethasone Respiratory Insoluble; Budesonide Respiratory Sparingly; Buprenorphine CNS Slightly; Butalbital CNS Insoluble; Carbamazepine CNS Insoluble; Carbidopa CNS Slightly; Cefotaxime Anti-infective Sparingly; Cephalexin Anti-infective Slightly; Cholestyramine Cardiovascular Insoluble; Ciprofloxacin Anti-infective Insoluble; Cisapride Gastrointestinal Insoluble; Cisplatin Anticancer Slightly; Clarithromycin Anti-infective Insoluble; Clonazepam CNS Slightly; Clozapine CNS Slightly; Cyclosporin Immunosuppressant Practically Insoluble; Diazepam CNS Slightly; Diclofenac sodium NSAID Sparingly; Digoxin Cardiovascular Insoluble; Dipyridamole Cardiovascular Slightly; Divalproex CNS Slightly; Dobutamine Cardiovascular Sparingly; Doxazosin Cardiovascular Slightly; Enalapril Cardiovascular Sparingly; Estradiol Hormone Insoluble; Etodolac NSAID Insoluble; Etoposide Anticancer Very Slightly; Famotidine Gastrointestinal Slightly; Felodipine Cardiovascular Insoluble; Fentanyl citrate CNS Sparingly; Fexofenadine Respiratory Slightly; Finasteride Genito-urinary Insoluble; Fluconazole Antifungal Slightly; Flunosolide Respiratory Insoluble; Flurbiprofen NSAID Slightly; Fluvoxamine CNS Sparingly; Furosemide Cardiovascular Insoluble; Glipizide Metabolic Insoluble; Glyburide Metabolic Sparingly; Ibuprofen NSAID Insoluble; Isosorbide dinitrate Cardiovascular Sparingly; Isotretinoin Dermatological Insoluble; Isradipine Cardiovascular Insoluble; Itraconzole Antifungal Insoluble; Ketoconazole Antifungal Insoluble; Ketoprofen NSAID Slightly; Lamotrigine CNS Slightly; Lansoprazole Gastrointestinal Insoluble; Loperamide Gastrointestinal Slightly; Loratadine Respiratory Insoluble; Lorazepam CNS Insoluble; Lovastatin Cardiovascular Insoluble; Medroxyprogesterone Hormone Insoluble; Mefenamic acid Analgesic Slightly; Methylprednisolone Steroid Insoluble; Midazolam Anesthesia Insoluble; Mometasone Steroid Insoluble; Nabumetone NSAID Insoluble; Naproxen NSAID Insoluble; Nicergoline CNS Insoluble; Nifedipine Cardiovascular Practically Insoluble; Norfloxacin Anti-infective Slightly; Omeprazole Gastrointestinal Slightly; Paclitaxel Anticancer Insoluble; Phenytoin CNS Insoluble; Piroxicam NSAID Sparingly; Quinapril Cardiovascular Insoluble; Ramipril Cardiovascular Insoluble; Risperidone CNS Insoluble; Sertraline CNS Slightly; Simvastatin Cardiovascular Insoluble; Terbinafine Antifungal Slightly; Terfenadine Respiratory Slightly; Triamcinolone Steroid Insoluble; Valproic acid CNS Slightly; Zolpidem CNS Sparingly.

The following is a listing of therapeutic agents that are slightly soluble, sparingly soluble or insoluble in water, and have low bioavailability. The format is (1) Drug Name, (2) Therapeutic Class, (3) Solubility In Water, and (4) Bioavailability. Astemizol Allergic Rhinitis Insoluble Low-moderate; Cyclandelate Peripheral vascular disease Insoluble Low; Perphenazine Psychotic disorder Insoluble Low; Testosterone Androgen Replacement Insoluble Low; Famotidine GERD Slightly soluble Low; Budesonide Allergic Rhinitis Sparingly soluble Low; Mesalamine Irritable Bowel Syndrome Slightly soluble Low; Clemastine Allergic Rhinitis Slightly soluble Low; Buprenorphine Pain Slightly soluble Low; Sertraline Anxiety Slightly soluble Low; Auranofin Arthritis Slightly soluble Low; Felodipine Hypertension Insoluble Low; Isradipine Hypertension Insoluble Low; Danazol Endometriosis Insoluble Low; Loratadine Allergic Rhinitis Insoluble Low; Isosorbide dinitrate Angina Sparingly soluble Low; Fluphenazine Psychotic disorder Insoluble Low; Spironolactone Hypertension, Edema Insoluble Low; Biperiden Parkinson's disease Sparingly soluble Low; Cyclosporin Transplantation Slightly soluble Low; Norfloxacin Bacterial Infection Slightly soluble Low; Cisapride GERD Insoluble Low; Nabumetone Arthritis Insoluble Low; Dronabinol ANTIEMETIC Insoluble Low; Lovastatin Hyperlipidemia Insoluble Low; Simvastatin Hyperlipidemia Insoluble Low.

Solubility of Salts: The solubility of some common monovalent and divalent metal cation salts is shown in Table 1. Suitable monovalent metal cation salts, e.g. sodium, potassium and lithium salts, and suitable divalent metal cation salts, e.g. calcium and magnesium salts, can have desired solubility characteristics. For example, sodium, potassium, calcium, and magnesium salts that are contained in the dry particles can have a solubility in distilled water at room temperature (20-30° C.) and 1 bar of at least about 0.4 g/L, at least about 0.85 g/L, at least about 0.90 g/L, at least about 0.95 g/L, at least about 1.0 g/L, at least about 2.0 g/L, at least about 5.0 g/L, at least about 6.0 g/L, at least about 10.0 g/L, at least about 20 g/L, at least about 50 g/L, at least about 90 g/L, at least about 120 g/L, at least about 500 g/L, at least about 700 g/L or at least about 1000 g/L. The sodium and potassium salts can have solubility greater than about 0.90 g/L, greater than about 2.0 g/L, or greater than about 90 g/L. Alternatively, the sodium and potassium salts that are contained in the dry particles can have a solubility in distilled water at room temperature (20-30° C.) and 1 bar of between at least about 0.4 g/L to about 200 g/L, between about 1.0 g/L to about 120 g/L, between 5.0 g/L to about 50 g/L.

Dry particles can be prepared, if desired, that contain mono- and/or divalent metal cation salts that are not highly soluble in water. As described herein, such dry particles can be prepared, e.g. using a feed stock of a different, more soluble salt, and permitting anion exchange to produce the desired mono- and/or divalent metal cation salts prior to or concurrently with spray drying. Alternatively, a suspension may also be fed to the spray dryer to make dry particles.

TABLE 1

Solubilities of monovalent and divalent salts
Mono and Divalent Salt Solubility

| Salt | Water solubility at 20-30° C., 1 bar; |
|---|---|
| Potassium chloride | 1 g/2.8 mL[1] |
| Potassium citrate | Monohydrate, 1 g/0.65 mL[1] |
| Sodium ascorbate | 62 g/100 mL[1] |
| Sodium bicarbonate | Soluble in 10 parts[1] |
| Sodium carbonate | Soluble in 3.5 parts[1]; 503[3] g/L |
| Sodium chloride | 1 g/2.8 mL[1]; 360[3] g/L |
| Sodium citrate | Dihydrate, soluble in 1.3 parts[1]; 910[3] g/L |
| Sodium lactate | Commercially available as 70-80% in water[1] |
| Dibasic sodium phosphate | Soluble in ~8 parts[1] |
| Sodium propionate | 1 g/~1 mL[1] |
| Sodium sulfate | Soluble in 3.6 parts[1]; 194[3] g/L |
| Calcium chloride | 1368[2,3] g/L |
| Calcium acetate | 347[3] g/L |
| Calcium lactate | 105[3] g/L |
| Calcium gluconate | 33.23[1] g/L |
| Calcium sulfate | 2.98[3] g/L |
| Calcium citrate | 0.96[3] g/L |
| Calcium phosphate dibasic | 0.2[3] g/L |
| Calcium carbonate | Pract. Insol.[2] |
| Calcium stearate | Pract. Insol.[2] |
| Calcium alginate | Not applicable |
| Magnesium lactate | 1 g/25 mL in cold water[1] (about 40 g/L) |
| Magnesium carbonate | 4.5 in 100 parts[2] |
| Magnesium carbonate hydroxide | Soluble in 3300 parts of $CO_2$ free water[1] |
| Magnesium chloride | Hexahydrate, 1 g/0.6 mL[1] |
| Magnesium citrate | Partially soluble in cold water[3] |
| Magnesium sulfate | Heptahydrate, 71 g/100 mL[1] |

[1]O'Neil, Maryadele J. *The Merck Index: an Encyclopedia of Chemicals, Drugs, and Biologicals*. 14th ed. Whitehouse Station, N.J.: Merck, 2006. Print.
[2] Solubility at 60° C.
[3]Perry, Robert H., Don W. Green, and James O. Maloney. *Perry's Chemical Engineers' Handbook*. 7th ed. New York: McGraw-Hill, 1997. Print.
[4]U.S. Pharmacopeia, USP29, Feb. 26, 2013 on-line access edition
[5]Higashiyama, Takanobu (2002). "Novel functions and applications of trehalose". *Pure Appl. Chem.* 74 (7): 1263-1269

Solubility of Excipients: The solubility of leucine in water is 24.26 g/L at 25 C[1], the solubility of mannitol in water is 1 g in about 5.5 mL of water[1] (about 182 g/L) ("freely soluble in water[4]), maltodextrin is "freely soluble or readily dispersible in water"[4], and the solubility of trehalose is 68.9 g per 100 g of water at 20 C[5].

Molecular Weights of Some Mono and Divalent Metal Cation Salts

It is generally preferred that the metal cation salt (e.g., a sodium, magnesium, potassium or calcium salt) is a salt with a low molecular weight. It is generally preferred that the metal cation salt (e.g., a sodium, magnesium, potassium or calcium salt) has a molecular weight of less than about 5000 g/mol, less than about 4000 g/mol, less than about 3000 g/mol, less than about 2000 g/mol, less than about 1500 g/mol, less than about 1000 g/mol, less than about 950 g/mol, less than about 900 g/mol, less than about 850 g/mol, less than about 800 g/mol, less than about 750 g/mol, less than about 700 g/mol, less than about 650 g/mol, less than about 600 g/mol, less than about 550 g/mol, less than about 510 g/mol, less than about 500 g/mol, less than about 450 g/mol, less than about 400 g/mol, less than about 350 g/mol, less than about 300 g/mol, less than about 250 g/mol, less than about 200 g/mol, less than about 150 g/mol, less than about 125 g/mol, less than about 100 g/mol; or between about 2000 g/mol to about 5000 g/mol, or between about 500 g/mol to about 2000 g/mol, or between about 100 g/mol and about 500 g/mol. In addition or alternatively, the metal cation (e.g., a sodium, magnesium, potassium, or calcium ion) preferably contributes about 10% to about 60% of the weight of the overall salt; or about 10% to about 25%, about 25% to about 45%, about 45% to about 60%; or about 10% to about 15%, about 15% to about 20%, about 20% to about 25%, about 25% to about 30%, about 30% to about 35%, about 35% to about 40%, about 40% to about 45%, about 45% to about 50%, or about 50% to about 60% of the weight of the overall metal cation salt (e.g., a sodium, magnesium, potassium, or calcium salt).

Alternatively or in addition, the respirable dry particles of the invention can include a suitable metal cation salt (e.g., a sodium, magnesium, potassium, or calcium salt) that provides metal cation (a sodium, magnesium, potassium, or calcium ion), wherein the weight ratio of metal cation to the overall weight of said salt is between about 0.1 to about 0.6. For example, the weight ratio of metal cation to the overall weight of said salt is between about 0.15 to about 0.55, between about 0.18 to about 0.5, between about 0.2 to about 5, between about 0.25 to about 0.5, between about 0.27 to about 0.5, between about 0.3 to about 5, between about 0.35 to about 0.5, between about 0.37 to about 0.5, between about 0.4 to about 0.5, between about 0.1 and 0.4, between about 0.1 and about 0.2, between about 0.15 and 0.4, or between about 0.2 to about 0.3.

The molecular weight of some common monovalent and divalent metal cation salts is listed in Table 2.

TABLE 2

Weight Percent Cation in Metal Salt Molecules

| Salt | Molecular Formula | MW (g/mol) | Weight % of cation in molecule |
|---|---|---|---|
| Potassium chloride | KCl | 74.55 | 52.45 |
| Potassium citrate | $C_6H_5K_3O_7$ | 306.39 | 38.28 |
| Sodium ascorbate | $C_6H_7NaO_6$ | 198.11 | 20.23 |
| Sodium bicarbonate | $CHNaO_3$ | 84.01 | 47.71 |
| Sodium carbonate | $CNa_2O_3$ | 105.99 | 43.38 |
| Sodium chloride | NaCl | 58.44 | 39.34 |
| Sodium citrate | $C_6H_5Na_3O_7$ | 258.07 | 26.73 |
| Sodium lactate | $C_3H_5NaO_3$ | 112.06 | 20.52 |
| Dibasic sodium phosphate | $HNa_2O_4P$ | 141.96 | 28.23 |
| Sodium propionate | $C_3H_5NaO_2$ | 96.06 | 41.72 |
| Sodium sulfate | $Na_2O_4S$ | 142.04 | 32.37 |
| Calcium carbonate | $CaCO_3$ | 100.09 | 40.0 |
| Calcium chloride | $CaCl_2$ | 110.98 | 36.0 |
| Calcium phosphate dibasic | $CaHPO_4$ | 136.06 | 29.4 |
| Calcium sulfate | $CaSO_4$ | 136.14 | 29.4 |
| Calcium acetate | $Ca(C_2H_3O_2)_2$ | 158.17 | 25.3 |
| Calcium citrate | $Ca_3(C_6H_5O_7)_2$ | 498.46 | 24.1 |
| Calcium lactate | $Ca(C_3H_5O_3)_2$ | 218.218 | 18.3 |
| Calcium sorbate | $CaC_{12}H_{14}O_4$ | 262.33 | 15.2 |

TABLE 2-continued

Weight Percent Cation in Metal Salt Molecules

| Salt | Molecular Formula | MW (g/mol) | Weight % of cation in molecule |
|---|---|---|---|
| Calcium gluconate | $CaC_{12}H_{22}O_{14}$ | 430.373 | 9.3 |
| Calcium stearate | $CaC_{36}H_{70}O_4$ | 607.02 | 6.6 |
| Calcium alginate | $[Ca(C_6H_7O_6)_2]_n$ | NA | NA |
| Magnesium carbonate | $MgCO3$ | 84.31 | 28.8 |
| Magnesium carbonate hydroxide | $(MgCO3)4 \cdot Mg(OH)2$ | 395.61 | 30.7 |
| Magnesium chloride | $MgCl2$ | 95.21 | 25.5 |
| Magnesium citrate tribasic | $Mg3(C6H5O7)2$ | 451.11 | 16.2 |
| Magnesium lactate | $Mg(C3H5O3)2$ | 202.45 | 12.0 |
| Magnesium sulfate | $MgSO4$ | 120.37 | 20.2 |

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, spray freeze drying, milling (e.g., jet milling), blending, solvent extraction, solvent evaporation, phase separation, simple and complex coacervation, interfacial polymerization, suitable methods that involve the use of supercritical carbon dioxide (C02), sonocrystalliztion, nanoparticle aggregate formation and other suitable methods, including combinations thereof. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

The respirable dry particles are preferably spray dried. Suitable spray drying techniques are described, for example, by K. Masters in “Spray Drying Handbook”, John Wiley & Sons, New York (1984). Generally, during spray drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by GEA Group (Niro, Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the invention, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions.

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD, or between 0.5 to about 5 micron VMGD.

The invention also relates to respirable dry powders or respirable dry particles produced by preparing a feedstock solution, emulsion or suspension and spray drying the feedstock according to the methods described herein, and to the methods described herein. The feedstock can be prepared, for example, using (a) monovalent salt, such as sodium chloride or potassium chloride, in an amount of about 1% to 100% by weight (e.g., of total solutes used for preparing the feedstock), an excipient, such as leucine, in an amount of about 0% to 99% by weight (e.g., of total solutes used for preparing the feedstock), and optionally a pharmaceutically therapeutic agent in an amount of about 0.001% to 99% by weight (e.g., of total solutes used for preparing the feedstock), and one or more suitable solvents for dissolution of the solute and formation of the feedstock. In another example, the feedstock can be prepared using a divalent salt or a combination of a monovalent salt and a divalent salt.

Any suitable method can be used for mixing the solutes and solvents to prepare feedstocks (e.g., static mixing, bulk mixing). If desired, additional components that cause or facilitate the mixing can be included in the feedstock. For example, carbon dioxide produces fizzing or effervescence and thus can serve to promote physical mixing of the solute and solvents. Various salts of carbonate or bicarbonate can promote the same effect that carbon dioxide produces and, therefore, can be used in preparation of the feedstocks of the invention.

In an embodiment, the respirable dry powders or respirable dry particles of the invention can be produced through an ion exchange reaction. In certain embodiments of the invention, two saturated or sub-saturated solutions are fed into a static mixer in order to obtain a saturated or supersaturated solution post-static mixing. Preferably, the post-mixed solution is supersaturated. The post-mixed solution may be supersaturated in all components or supersaturated in one, two, or three of the components.

The two solutions may be aqueous or organic, but are preferably substantially aqueous. When the therapeutic agent is dissolved in an organic solvent, then one feed solution may be organic while the other one may be aqueous, or both feed solutions may be organic. The post-static mixing solution is then fed into the atomizing unit of a spray dryer. In a preferable embodiment, the post-static mixing solution is immediately fed into the atomizer unit. Some examples of an atomizer unit include a two-fluid nozzle, a rotary atomizer, or a pressure nozzle. Preferably, the atomizer unit is a two-fluid nozzle. In one embodiment, the two-fluid nozzle is an internally mixing nozzle, meaning that the gas impinges on the liquid feed before exiting to most outward orifice. In another embodiment, the two-fluid nozzle is an externally mixing nozzle, meaning that the gas impinges on the liquid feed after exiting the most outward orifice.

Dry Powder Properties

Geometric or Volume Diameter. Volume median diameter (VMD) (×50), which may also be referred to as volume median geometric diameter (VMGD) and Dv(50), may be determined using a laser diffraction technique. For example, a HELOS diffractometer and a RODOS dry powder disperser (Sympatec, Inc., Princeton, N.J.) may be employed. The RODOS disperser applies a shear force to a sample of particles, controlled by the regulator pressure (typically set at 1.0 bar with maximum orifice ring pressure) of the incoming compressed dry air. The pressure settings may be varied to vary the amount of energy used to disperse the powder. For example, the regulator pressure may be varied from 0.2 bar to 4.0 bar. A powder sample is dispensed from a microspatula into the RODOS funnel. The dispersed particles travel through a laser beam where a resulting diffracted light pattern is produced and collected, typically using an R1 lens, by a series of detectors. The ensemble diffraction pattern is then translated into a volume-based particle size distribution using the Fraunhofer diffraction model, on the basis that smaller particles diffract light at larger angles. Using this method, geometric standard deviation (GSD) for the volume mean geometric diameter may also determined. Other operating principles and measurement tools may also be employed to measure the VMGD For example, VMGD can be measured using an electrical zone sensing instrument such as a Multisizer IIe, (Coulter Electronic, Luton, Beds, England), or as with the HELOS, laser diffraction may be used as in the Mastersizer system (Malvern, Worcestershire, UK). Other instruments for measuring particle geometric diameter are well known in the art. The diameter of dry particles in a sample will range depending upon factors such as particle composition and methods of synthesis.

In certain aspects, the dry particles have a VMGD as measured by HELOS/RODOS at 1.0 bar of about 10 μm or less (e.g., about 0.1 μm to about 10 μm). The dry particles can have a VMGD of about 9 μm or less (e.g., about 0.1 μm to about 9 μm), about 8 μm or less (e.g., about 0.1 μm to about 8 μm), about 7 μm or less (e.g., about 0.1 μm to about 7 μm), about 6 μm or less (e.g., about 0.1 μm to about 6 μm), about 5 μm or less (e.g., less than 5 μm, about 0.1 μm to about 5 μm), about 4 μm or less (e.g., 0.1 μm to about 4 μm), about 3 μm or less (e.g., 0.1 μm to about 3 μm), about 2 μm or less (e.g., 0.1 μm to about 2 μm), about 1 μm or less (e.g., 0.1 μm to about 1 μm), about 1 μm to about 6 μm, about 1 μm to about 5 μm, about 1 μm to about 4 μm, about 1 μm to about 3 μm, or about 1 μm to about 2 μm as measured by HELOS/RODOS at 1.0 bar.

The Dv50 of the respirable dry powders and dry particles can be expressed as the Dv50 of a respirable size, e.g., between about 0.5 μm and about 10 μm, between about 0.5 μm and about 7 μm, between about 0.5 μm and about 5 μm, between about 1 μm and about 5 μm, between about 1 μm and about 3 μm, between about 3 μm and about 5 μm, between about 2 μm and about 4 μm, that is emitted from a dry powder inhaler when a total inhalation energy of less than about 20 Joules or less than about 10 Joules, of less than about 2 Joules or less than about 1 Joule, or less than about 0.8 Joule, or less than about 0.5 Joule, or less than about 0.3 Joule is applied to the dry powder inhaler, or when the inhalation flowrate is 60 LPM, 30 LPM, 20 LPM, or 15 LPM. The dry powder can fill the unit dose container, or the unit dose container can be at least 10% full, at least 20% full, at least 30% full, at least 40% full, at least 50% full, at least 60% full, at least 70% full, at least 80% full, or at least 90% full. The unit dose container can be a capsule (e.g., size 000, 00, 0E, 0, 1, 2, 3, and 4, with respective volumetric capacities of 1.37 ml, 950 μl, 770 μl, 680 μl, 480 μl, 360 μl, 270 μl, and 200 μl).

In order to compare the dispersion of powder at different flow rates, volumes, and from inhalers of different resistances, the energy required to perform the inhalation maneuver can be calculated. Inhalation energy is defined as $E=R^2Q^2V$ where E is the inhalation energy in Joules, R is the inhaler resistance in $kPa^{1/2}/LPM$ (also expressed as sqrt (kPa)/liters per minutes), Q is the steady flow rate in LPM and V is the inhaled air volume in L. For example, with an RS-01HR inhaler with a resistance of 0.034 kPa$^{1/2}$/LPM, the inhalation energy for the case of 60 LPM and 2 L inhalation is 8.3 Joules.

Additionally, the capsule emitted powder mass (CEPM) can be determined using suitable methods. Preferably the respirable dry powders have a CEPM of at least 80% when emitted from a passive dry powder inhaler that has a resistance of about 0.036 sqrt(kPa)/liters per minute under the following conditions: an inhalation energy of 1.15 Joules at a flow rate of 30 LPM using a size 3 capsule that contains a total mass of 25 mg. Preferably, the total mass contained within the capsule consists of the respirable dry particles that comprise a divalent metal cation salt, and the volume median geometric diameter of the respirable dry particles emitted from the inhaler is 5 microns or less.

Dispersibility Ratio. The respirable dry powders and dry particles are characterized by a 1 bar/4 bar ratio or the 0.5 bar/4 bar ratio, that is less than 2.0, and preferably, close to 1.0. The dry particles of the invention have 1 bar/4 bar and/or 0.5 bar/4 bar of less than 1.9, less than 1.8, less than 1.7, less than 1.6, less than 1.5, less than 1.4, less than 1.35, less than 1.3, less than 1.25, less than 1.2, less than 1.15, less than 1.1. For the values listed above, the lower range of the 1 bar/4 bar ratio or 0.5 bar/4 bar ratio is about 1.0, but can go as low as 0.9. Alternatively, the lower range of the 1 bar/4 bar ratio or 0.5 bar/4 bar ratio is about 0.9, preferably about 0.95, and most preferably about 1.0. Preferably, the 1 bar/4 bar ratio or 0.5 bar/4 bar ratio is less than 1.7, less than 1.35, or less than 1.2, and, for all three values, greater than 0.9. Preferably 1 bar/4 bar and/or 0.5 bar/4 bar are measured by laser diffraction using a HELOS/RODOS system.

Alternatively, the respirable dry powders and dry particles are characterized by a Dv50 at the 60 LPM/15 LPM ratio or at the 60 LPM/20 LPM ratio that is less than 2.0, and preferably, close to 1.0. The dry particles of the invention have 1 bar/4 bar and/or 0.5 bar/4 bar of less than 1.9, less than 1.8, less than 1.7, less than 1.6, less than 1.5, less than 1.4, less than 1.35, less than 1.3, less than 1.25, less than 1.2, less than 1.15, less than 1.1. For the values listed above, the lower range of the 1 bar/4 bar ratio or 0.5 bar/4 bar ratio is about 1.0, but can go as low as 0.9.

Density

Tapped Density. Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture, high particle cohesiveness and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopeia convention, Rockville, Md., 10th Supplement, 4950-4951, 1999. For the purposes of this specification, the words "tap density" and "tapped density" are synonymous.

A dry powder comprising the dry particles can have a tap density of about 0.1 $g/cm^3$ to about 1.0 $g/cm^3$. For example, the dry particles can have a tap density of about 0.1 $g/cm^3$ to about 0.9 $g/cm^3$, about 0.2 $g/cm^3$ to about 0.9 $g/cm^3$, about 0.2 $g/cm^3$ to about 0.9 $g/cm^3$, about 0.3 $g/cm^3$ to about 0.9 $g/cm^3$, about 0.4 $g/cm^3$ to about 0.9 $g/cm^3$, about 0.5 $g/cm^3$ to about 0.9 $g/cm^3$, or about 0.5 $g/cm^3$ to about 0.8 $g/cm^3$, greater than about 0.4 g/cc, greater than about 0.45 g/cc, greater than about 0.5 g/cc, greater than about 0.55 g/cc, greater than about 0.6 g/cc, greater than about 0.7 g/cc, about 0.1 $g/cm^3$ to about 0.8 $g/cm^3$, about 0.1 $g/cm^3$ to about 0.7 $g/cm^3$, about 0.1 $g/cm^3$ to about 0.6 $g/cm^3$, about 0.1 $g/cm^3$ to about 0.5 $g/cm^3$, about 0.1 $g/cm^3$ to about 0.4 $g/cm^3$, about 0.1 $g/cm^3$ to about 0.3 $g/cm^3$, less than 0.3 $g/cm^3$. In one embodiment, tap density is preferably greater than about 0.45 $g/cm^3$, more preferably greater than 0.55 $g/cm^3$. Alternatively, tap density is less than about 0.4 $g/cm^3$.

In another aspect of the invention, the dry powder comprising the dry particles can have a tap density of greater than 0.4 $g/cm^3$ to about 1.4 $g/cm^3$. For example, the dry particles can have a tap density of about 0.45 $g/cm^3$ to about 1.35 $g/cm^3$, about 0.5 $g/cm^3$ to about 1.3 $g/cm^3$, about 0.55 $g/cm^3$ to about 1.25 $g/cm^3$, about 0.6 $g/cm^3$ to about 1.2 $g/cm^3$, about 0.65 $g/cm^3$ to about 1.15 $g/cm^3$, about 0.7 $g/cm^3$ to about 1.1 $g/cm^3$, about 0.75 $g/cm^3$ to about 1.05 $g/cm^3$, about 0.8 $g/cm^3$ to about 1.0 $g/cm^3$.

Bulk Density. Bulk density, also referred to as the "apparent density", may be estimated prior to tap density measurement by dividing the weight of the powder by the volume of the powder, as estimated using the volumetric measuring device.

A dry powder comprising the dry particles can have a bulk density of about 0.1 $g/cm^3$ to about 1.0 $g/cm^3$. For example, the dry particles can have a bulk density of at least about 0.15 g/ml, at least about 0.18 g/ml, at least about 0.2 g/ml, at least about 0.3 g/ml, at least about 0.4 g/ml.

In another aspect of the invention, the dry powder comprising the dry particles can have a bulk density of greater than 0.1 $g/cm^3$ to about 1.0 $g/cm^3$. For example, the dry particles can have a bulk density of about 0.15 $g/cm^3$ to about 0.95 $g/cm^3$, about 0.2 $g/cm^3$ to about 0.9 $g/cm^3$, about 0.25 $g/cm^3$ to about 0.8 $g/cm^3$, about 0.3 $g/cm^3$ to about 0.7 $g/cm^3$, about 0.35 $g/cm^3$ to about 0.65 $g/cm^3$, about 0.4 $g/cm^3$ to about 0.6 $g/cm^3$, about 0.45 $g/cm^3$ to about 0.6 $g/cm^3$. In preferred aspects of the invention, the bulk density is about 0.15 $g/cm^3$ to about 0.6 $g/cm^3$, or about 0.2 $g/cm^3$ to about 0.55 $g/cm^3$.

Skeletal Density. Skeletal Density, sometimes called true density, may be determined by the Accupyc II 1340 (Micrometrics, Norcross, Ga.), which uses a gas displacement technique to determine the volume of sample under test. The density is calculated using the sample weight which is determined using a balance. The instrument measures the volume of the sample, excluding interstitial voids in bulk powders and any open porosity in the individual particles, to which the gas has access. Internal (closed) porosity is still included in the volume.

A dry powder comprising the dry particles can have a skeletal density of about 0.5 $g/cm^3$ to about 2.5 $g/cm^3$. For example, the dry particles can have a skeletal density of about of about 0.5 $g/cm^3$ to about 2.25 $g/cm^3$, of about 0.8 $g/cm^3$ to about 2.1 $g/cm^3$, of about 0.9 $g/cm^3$ to about 2.0 $g/cm^3$, of about 1.0 $g/cm^3$ to about 1.9 $g/cm^3$, of about 1.1 $g/cm^3$ to about 1.8 $g/cm^3$, about 1.2 $g/cm^3$, about 1.3 $g/cm^3$, about 1.4 $g/cm^3$, about 1.5 $g/cm^3$, about 1.6 $g/cm^3$, about 1.7 $g/cm^3$.

Flowability

Angle of Repose. An experimentally derived assessment for a powder's flow properties is called the static angle of repose or "Angle of Repose". The angle of repose is also denoted the angle of slip and is a relative measure of the friction between the particles as well as a measure of the cohesiveness of the particles. It is the constant, three-dimensional angle (relative to the horizontal base) assumed by a cone-like pile of material formed by any of several different methods. See USP <1174> for a further description of this method. In general, a cohesive powder has an angle of repose of at least 40°, e.g., in the range of 40° to 50°. A freely flowing powder tends to possess an Angle of Repose of 30°, or less, although an Angle of Repose between 30° and 40° should lead to a powder which can be processed further without much difficultly.

A suitable dry powder comprising the dry particles can have an Angle of Repose of about 50° or less, about 45° or less, about 40° or less, about 35° or less, about 30° or less.

Hausner Ratio. The Hausner Ratio is a dimensionless number, which is calculated by dividing the tap density by the bulk density. It is a number that is correlated to the flowability of a powder or granular material. See USP29 <1174> for a further description of this method. There it is noted that dry powders with a Hausner Ratio greater than 1.35 are poor flowing powders. Flow properties and dispersibility are both negatively affected by particle agglomeration or aggregation. It is therefore unexpected that powders with Hausner Ratios that are higher than 1.7 would still be flowable.

A suitable dry powder comprising the dry particles can have a Hausner Ratio that is at least 1.5, and can be at least 1.6, at least 1.7, at least 1.8, at least 1.9, at least 2.0, at least 2.1, at least 2.2, at least 2.3, at least 2.4, at least 2.5, at least 2.6 or at least 2.7; or, between 1.5 and 2.7, between 1.6 and 2.6, between 1.7 and 2.5, between 1.8 and 2.4, between 1.9 and 2.3. In a further aspect, the Hausner Ratio is about 1.1, about 1.2, about 1.3, about 1.4; or, the dry powder comprising the dry particles can have a Hausner Ratio that is between 1.0 and 1.5, between 1.1 and 1.4, about 1.1, about 1.2, about 1.3, about 1.4.

Carr Index. The Carr index is an indication of the compressibility of a powder. It is calculated by dividing the difference between the bulk density and the tapped density by the bulk density, and multiplying the quotient by 100. The Carr index is frequently used in pharmaceutics as an indication of the flowability of a powder. A Carr index greater than 25 is considered to be an indication of poor flowability, and below 15, of good flowability. It is therefore unexpected that powders with Carr Index of greater than 40 would still be flowable.

A suitable dry powder comprising the dry particles can have a Carr Index that is at least 35, at least 40, at least 45, at least 50. Alternatively, the Carr Index can be between about 15 and 50, between 20 and 45, between 20 and 35, between 22 and 32, between 25 and 45, between 30 and 40.

Flow Through an Orifice. Additional insight may be gained with the Flow Through an Orifice test. See USP <1174> for a further description of this method. This method offers insight into a powder's flowability that may not have been determined by the Angle of Repose or by the Hausner Ratio. This method is useful for free-flowing materials. One method of measuring flow through an orifice is to determine the minimum diameter orifice through which powder flow can be observed. The Flowability Index, as defined herein, refers to the minimum diameter orifice through which powder flow can be observed. There are various instruments available to measure the Flowability Index, for example, a Flodex Powder Flowability Test Instrument (model 21-101-000, Hanson Research Corp., Chatsworth, Calif.).

A suitable dry powder comprising the dry particles can have a Flowability Index between about 15 mm to about 32 mm, between about 16 mm to about 30 mm, between about 17 mm to about 28 mm, between about 18 mm to about 26 mm, or equal to or less than about 30 mm, equal to or less than about 28 mm, equal to or less than about 26 mm, equal to or less than about 24 mm, equal to or less than about 22 mm, equal to or less than about 20 mm, equal to or less than about 18 mm, equal to or less than about 16 mm.

Form of the Dry Particles. The form of the dry particles can be observed by microscopy. Visual inspection can also be employed for evaluation of the appearance of the surface of the dry particles and of any agglomeration of the dry particles. The visual inspection may also be employed to observe e.g. a balloon effect, i.e. whether the cores contain air-filled hollow spaces.

Aerosolization Properties

Capsule Emitted Powder Mass (CEPM). The respirable dry powders and dry particles are characterized by a high emitted dose (e.g., CEPM of at least 40%, at least 45%, at least 50%, at least 55%, at least 60%, at least 65%, at least 70%, at least 75%, at least 80%, at least 85%, at least 90%, at least 95%) from a dry powder inhaler when a total inhalation energy of less than about 2 Joules or less than about 1 Joule, or less than about 0.8 Joule, or less than about 0.5 Joule, or less than about 0.3 Joule is applied to the dry powder inhaler. Preferably, the respirable dry powders and dry particles are characterized by a CEPM of at least 90% from a dry powder inhaler when a total inhalation energy of less than about 9 Joules is applied and/or a CEPM of at least 80% from a dry powder inhaler when a total inhalation energy of less than about 0.3 Joules is applied. The dry powder can fill the unit dose container, or the unit dose container can be at least 10% full, at least 20% full, at least 30% full, at least 40% full, at least 50% full, at least 60% full, at least 70% full, at least 80% full, or at least 90% full. The unit dose container can be a capsule (e.g., size 000, 00, 0E, 0, 1, 2, 3, and 4, with respective volumetric capacities of 1.37 ml, 950 μl, 770 μl, 680 μl, 480 μl, 360 μl, 270 μl, and 200 μl).

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 $kPa^{1/2}$/LPM, with a inhalation volume of 2 L based on both FDA guidance documents for dry powder inhalers and on the work of Tiddens et al. (Journal of Aerosol Med, 19(4), p. 456-465, 2006) who found adults averaging 2.2 L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p. 780-783, 2001) was used to predict maximum and minimum achievable PIFR through 2 dry powder inhalers of resistances 0.021 and 0.032 $kPa^{1/2}$/LPM for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention.

An advantage of aspects of the invention is the production of powders that disperse well across a wide range of flow rates and are relatively flow rate independent. In certain aspects, the dry particles and powders of the invention enable the use of a simple, passive DPI for a wide patient population.

Mass Median Aerodynamic Diameter (MMAD). Alternatively or in addition, the respirable dry particles of the invention can have an MMAD of about 10 microns or less, such as an MMAD of about 0.5 micron to about 10 microns. Preferably, the dry particles of the invention have an MMAD of about 5 microns or less (e.g., about 0.5 micron to about 5 microns, preferably about 1 micron to about 5 microns), about 4 microns or less (e.g., about 1 micron to about 4 microns), about 3.8 microns or less (e.g., about 1 micron to about 3.8 microns), about 3.5 microns or less (e.g., about 1 micron to about 3.5 microns), about 3.2 microns or less (e.g., about 1 micron to about 3.2 microns), about 3 microns or less (e.g., about 1 micron to about 3.0 microns), about 2.8 microns or less (e.g., about 1 micron to about 2.8 microns), about 2.2 microns or less (e.g., about 1 micron to about 2.2 microns), about 2.0 microns or less (e.g., about 1 micron to about 2.0 microns) or about 1.8 microns or less (e.g., about 1 micron to about 1.8 microns).

Fine Particle Fraction (FPF). Alternatively or in addition, the respirable dry powders and dry particles of the invention can have an FPF of less than about 5.6 microns (FPF<5.6 µm) of at least about 20%, at least about 30%, at least about 40%, preferably at least about 45%, at least about 50%, at least about 55%, at least about 60%, at least about 65%, or at least about 70%.

Alternatively or in addition, the dry powders and dry particles of the invention have a FPF of less than 5.0 microns (FPF_TD<5.0 µm) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the invention have a FPF of less than 5.0 microns of the emitted dose (FPF_ED<5.0 µm) of at least about 45%, preferably at least about 50%, at least about 60%, at least about 65%, at least about 70%, at least about 75%, at least about 80%, or at least about 85%. Alternatively or in addition, the dry powders and dry particles of the invention can have an FPF of less than about 3.4 microns (FPF<3.4 µm) of at least about 20%, preferably at least about 25%, at least about 30%, at least about 35%, at least about 40%, at least about 45%, at least about 50%, or at least about 55%.

Density and Aerosolization Property Testing Techniques

The diameter of the respirable dry particles, for example, their VMGD, can be measured using an electrical zone sensing instrument such as a Multisizer IIe, (Coulter Electronic, Luton, Beds, England), or a laser diffraction instrument such as a HELOS system (Sympatec, Princeton, N.J.) or a Mastersizer system (Malvern, Worcestershire, UK). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Aerosol Particle Sizer (APS) Spectrometer (TSI Inc., Shoreview, Minn.) can be used to measure aerodynamic diameter. The APS measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor (ACI) and the multi-stage liquid impinger (MSLI) methods. The methods and instruments for measuring particle aerodynamic diameter are well known in the art.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture, high particle cohesiveness and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopeia convention, Rockville, Md., 10th Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade Impactor, is one method of measuring the size distribution, or fine particle fraction, of airborne respirable dry particles. The ACI is an eight-stage Impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages 0 and 2 of the eight-stage ACI, as well as the final collection filter, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on the final collection filter is thus composed of respirable dry particles having an aerodynamic diameter of less than 3.4 microns. The airflow at such a calibration is approximately 60 L/min. The FPF(<5.6) has been demonstrated to correlate to the fraction of the powder that is able to reach the lungs of the patient, while the FPF(<3.4) has been demonstrated to correlate to the fraction of the powder that reaches the deep lung of a patient. These correlations provide a quantitative indicator that can be used for particle optimization.

The FPF(<5.6) has been demonstrated to correlate to the fraction of the powder that is able to make it into the lung of the patient, while the FPF(<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing and analyzing all stages, all stage filters, and the induction port of the ACI to the nominal dose. The FPF_TD(<5.0) is the ratio of the interpolated amount of powder depositing below 5.0 µm on the ACI to the nominal dose. The FPF_RD (<5.0) is the ratio of the interpolated amount of powder depositing below 5.0 µm on the ACI to either the gravimetric recovered dose or the analytical recovered dose.

Another way to approximate emitted dose is to determine how much powder leaves its container, e.g. capture or blister, upon actuation of a dry powder inhaler (DPI). This takes into account the percentage leaving the capsule, but does not take into account any powder depositing on the DPI. The emitted powder mass is the difference in the weight of the capsule with the dose before inhaler actuation and the weight of the capsule after inhaler actuation. This measurement can be called the capsule emitted powder mass (CEPM) or sometimes termed "shot-weight".

A Multi-Stage Liquid Impinger (MSLI) is another device that can be used to measure fine particle fraction. The MSLI operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The geometric particle size distribution can be measured for the respirable dry powder after being emitted from a dry powder inhaler (DPI) by use of a laser diffraction instrument such as the Malvem Spraytec. With the inhaler adapter in the close-bench configuration, an airtight seal is made to the DPI, causing the outlet aerosol to pass perpendicularly through the laser beam as an internal flow. In this way, known flow rates can be drawn through the DPI by vacuum pressure to empty the DPI. The resulting geometric particle size distribution of the aerosol is measured by the photodetectors with samples typically taken at 1000 Hz for the duration of the inhalation and the DV50, GSD, FPF<5.0 µm measured and averaged over the duration of the inhalation.

The invention also relates to a respirable dry powder or respirable dry particles produced using any of the methods described herein.

The respirable dry particles of the invention can also be characterized by the physicochemical stability of the salts or the excipients that the respirable dry particles comprise. The physicochemical stability of the constituent salts can affect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the invention include salts that are generally stable over a long period time.

If desired, the respirable dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. For example, maltodextrin may act as an amorphous phase stabilizer and inhibit the components from converting from an amorphous to crystalline state. Alternatively, a post-processing step to help the particles through the crystallization process in a controlled way (e.g., on the product filter at elevated humidity) can be employed with the resultant powder potentially being further processed to restore their dispersibility if agglomerates formed during the crystallization process, such as by passing the particles through a cyclone to break apart the agglomerates. Another possible approach is to optimize around formulation or process conditions that lead to manufacturing particles that are more crystalline and therefore more stable. Another approach is to use different excipients, or different levels of current excipients to attempt to manufacture more stable forms of the salts.

Crystallinity and Amorphous Content

The respirable dry particles can be characterized by the crystalline and amorphous content of the particles. The respirable dry particles can comprise a mixture of amorphous and crystalline content, in which the monovalent metal cation salt, e.g., sodium salt and/or potassium salt, is substantially in the crystalline phase. As described herein, the respirable dry particles can further comprise an excipient, such as leucine, maltodextrin or mannitol, and/or a therapeutic agent. The excipient and pharmaceutically therapeutic agent can independently be crystalline or amorphous or present in a combination of these forms. In some embodiments, the excipient is amorphous or predominately amorphous. In some embodiments, the respirable dry particles are substantially crystalline.

This provides several advantages. For example, the crystalline phase (e.g., crystalline sodium chloride) can contribute to the stability of the dry particle in the dry state and to the dispersibility characteristics, whereas the amorphous phase (e.g., amorphous therapeutic agent and/or excipient) can facilitate rapid water uptake and dissolution of the particle upon deposition in the respiratory tract. It is particularly advantageous when salts with relatively high aqueous solubilities (such as sodium chloride) that are present in the dry particles are in a crystalline state and when salts with relatively low aqueous solubilities (such as calcium citrate) are present in the dry particles in an amorphous state.

The amorphous phase can be characterized by a high glass transition temperature (Tg), such as a Tg of at least 100° C., at least 110° C., 120° C., at least 125° C., at least 130° C., at least 135° C., at least 140° C., between 120° C. and 200° C., between 125° C. and 200° C., between 130° C. and 200° C., between 120° C. and 190° C., between 125° C. and 190° C., between 130° C. and 190° C., between 120° C. and 180° C., between 125° C. and 180° C., or between 130° C. and 180° C. Alternatively, the amorphous phase can be characterized by a high Tg such as at least 800° C. or at least 900° C.

In some embodiments, the respirable dry particles contain an excipient and/or therapeutic agent rich amorphous phase and a monovalent salt (sodium salt, potassium salt) crystalline phase and the ratio of amorphous phase to crystalline phase (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain an amorphous phase and a monovalent salt crystalline phase and the ratio of amorphous phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain an amorphous phase and a monovalent salt crystalline phase and the ratio of crystalline phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5.

Heat of Solution

In addition to any of the features and properties described herein, in any combination, the respirable dry particles can have a heat of solution that is not highly exothermic. Preferably, the heat of solution is determined using the ionic liquid of a simulated lung fluid (e.g., as described in Moss, O. R. 1979. Simulants of lung interstitial fluid. Health Phys. 36, 447-448; or in Sun, G. 2001. Oxidative interactions of synthetic lung epithelial lining fluid with metal-containing particulate matter. Am J Physiol Lung Cell Mol Physiol. 281, L807-L815) at pH 7.4 and 37° C. in an isothermal calorimeter. For example, the respirable dry particles can have a heat of solution that is less exothermic than the heat of solution of calcium chloride dihydrate, e.g., have a heat of solution that is greater than about −10 kcal/mol, greater than about −9 kcal/mol, greater than about −8 kcal/mol, greater than about −7 kcal/mol, greater than about −6 kcal/mol, greater than about −5 kcal/mol, greater than about −4 kcal/mol, greater than about −3 kcal/mol, greater than about −2 kcal/mol, greater than about −1 kcal/mol or about −10 kcal/mol to about 10 kcal/mol.

Water or Solvent Content

Alternatively or in addition, the respirable dry powders and dry particles of the invention can have a water or solvent content of less than about 25%, less than about 20%, less than about 15% by weight of the dry particle. For example, the dry particles can have a water or solvent content of less than about 25%, less than about 20%, less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The dry particles can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5%, or about 5%.

Targeting Delivery

The respirable dry particles and dry powders described herein are suitable for inhalation therapies. The respirable dry particles may be fabricated with the appropriate material, surface roughness, diameter and density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration.

Storage

Because the respirable dry powders and respirable dry particles described herein contain salts, they may be hygroscopic. Accordingly it is desirable to store or maintain the respirable dry powders and respirable dry particles under conditions to prevent hydration of the powders. For example, if it is desirable to prevent hydration, the relative humidity of the storage environment should be less than 75%, less than 60%, less than 50%, less than 40%, less than 35%, less than 30%, less than 25%, less than 20%, less than 15%, less than 10%, or less than 5% humidity. In other embodiments, the storage environment should be between 20% to 40%, between 25% to 35%, about 30%, between 10% to 20%, or about 15% humidity. The respirable dry powders and respirable dry particles can be packaged (e.g., in sealed capsules, blisters, vials) under these conditions.

In preferred embodiments, the respirable dry powders or respirable dry particles of the invention possess aerosol characteristics that permit effective delivery of the respirable dry particles to the respiratory system without the use of propellants.

The dry particles of the invention can be blended with an active ingredient or co-formulated with an active ingredient to maintain the characteristic high dispersibility of the dry particles and dry powders of the invention.

Devices for Delivery the Dry Powders and Dry Particles to the Respiratory Tract

The following scientific journal articles are incorporated by reference for their thorough overview of the following dry powder inhaler (DPI) configurations: 1) Single-dose Capsule DPI, 2) Multi-dose Blister DPI, and 3) Multi-dose Reservoir DPI. N. Islam, E. Gladki, "Dry powder inhalers (DPIs)—A review of device reliability and innovation", *International Journal of Pharmaceuticals,* 360(2008): 1-11. H. Chystyn, "Diskus Review", *International Journal of Clinical Practice,* June 2007, 61, 6, 1022-1036. H. Steckel, B. Muller, "In vitro evaluation of dry powder inhalers I: drug deposition of commonly used devices", *International Journal of Pharmaceuticals,* 154(1997): 19-29.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, North Carolina), FlowCaps® (Hovione, Loures, Portugal), Inhalators® (Boehringer-Ingelheim, Germany), Aerolizer® (Novartis, Switzerland), high-resistance and low-resistance RS-01 (Plastiape, Italy). Some representative capsule-based DPI units are RS-01 (Plastiape, Italy), Turbospin (PH&T, Italy), Breezhaler (Novartis, Switzerland), Aerolizer (Novartis, Switzerland), Podhaler (Novartis, Switzerland), Handihaler (Boehringer Ingelheim, Germany), AIR (Civitas, Massachusetts), Dose One (Dose One, Maine), and Eclipse (Rhone Poulenc Rorer). Some representative unit dose DPIs are Conix (3M, Minnesota), Cricket (Mannkind, California), Dreamboat (Mannkind, California), Occoris (Team Consulting, Cambridge, UK), Solis (Sandoz), Trivair (Trimel Biopharma, Canada), Twincaps (Hovione, Loures, Portugal). Some representative blister-based DPI units are Diskus (GlaxoSmithKline (GSK), UK), Diskhaler (GSK), Taper Dry (3M, Minnesota), Gemini (GSK), Twincer (University of Groningen, Netherlands), Aspirair (Vectura, UK), Acu-Breathe (Respirics, Minnisota, USA), Exubra (Novartis, Switzerland), Gyrohaler (Vectura, UK), Omnihaler (Vectura, UK), Microdose (Microdose Therapeutix, USA), Multihaler (Cipla, India) Prohaler (Aptar), Technohaler (Vectura, UK), and Xcelovair (Mylan, Pennsylvania). Some representative reservoir-based DPI units are Clickhaler (Vectura), Next DPI (Chiesi), Easyhaler (Orion), Novolizer (Meda), Pulmojet (sanofi-aventis), Pulvinal (Chiesi), Skyehaler (Skyepharma), Duohaler (Vectura), Taifun (Akela), Flexhaler (AstraZeneca, Sweden), Turbuhaler (AstraZeneca, Sweden), and Twisthaler (Merck), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 µl, 770 µl, 680 µl, 480 µl, 360 µl, 270 µl, and 200 µl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using a breath-activated DPI. When this type of device is used, the energy of the subject's inhalation both disperses the respirable dry particles and draws them into the respiratory tract.

Pharmaceutical compositions. The dry powders comprised of dry particles obtained by one of the processes described herein, e.g., spray drying, may be used as such, or it may be further processed, and in either case, used as a oral dosage form for the delivery of an therapeutic agent. The oral dosage form may be designed to provide a rapid delivery of the therapeutic agent, a sustained delivery of the therapeutic agent, or at an in between rate.

In one aspect, the dry powders comprised of dry particles may be provided with a coating to obtain coated particles. Alternatively, an oral dosage form prepared using the dry powder (e.g., a tablet) may be coated, resulting in coated particles, granules, tablets or pellets, for example. Suitable coatings may be employed in order to obtain composition for immediate or modified release of the therapeutic agent and the coating employed is normally selected from the group consisting of film-coatings (for immediate or modified release) and enteric coatings or other kinds of modified release coatings, protective coatings or anti-adhesive coatings.

In one aspect of the invention, the dry powders comprised of dry particles described herein possess suitable properties for tableting purposes, for example, a dry powder that enhances tablet strength, reduces friability, modulates dissolution properties, enhances compressibility, and enhances coatability. In another aspect of the invention, further therapeutic agents (e.g. therapeutically and/or prophylactically therapeutic agents) and/or excipients are added to the particulate material (dry powder) before the manufacture of tablets.

For example, by using a mixture of i) an therapeutic agent contained in modified release coated particles or granules, or granules in the form of modified release matrices, and ii) an therapeutic agent in freely accessible form, an oral dosage formulation with a suitable release pattern can be designed in order to obtain a relatively fast release of an therapeutic agent followed by a modified (i.e., often prolonged) release of the same or a different therapeutic agent. In this example, the dry powders comprised of dry particles could play the role of providing a modified release of an therapeutic agent, or providing a fast release of the therapeutic agent, or both if different formulations of the dry particles are generated.

A dry powder obtained by a process according to the invention may be employed in any kind of inhalation device.

Capsules. Capsules are solid dosage forms in which the drug is enclosed within either a hard or soft soluble container or "shell." The shells are usually formed from gelatin; however, they also may be made from starch, such as hydroxypropyl methylcellulose (HPMC), or other suitable substances.

In capsule filling operations, the body and cap of the capsule are temporarily separated to allow powder to be filled into the capsule and then the capsule halves are reattached. Filling machines use various filling techniques, e.g., forming a powder plug by compression and then ejecting the plug into the empty capsule to fill powder into the capsule.

Various filling machines may be used to fill capsules and other receptacles such as polymer or foil based blister wells. One technology is the Dosator technology. Examples include the ModU C Capsule Filling and Closing Machine (Harro Hofliger, Germany) and the G250 Capsule Filler (MG2, Bologna, Italy) has a 'head' in which the dry powder is mechanically compacted and then discharged into an empty capsule. A technology called the Vacuum Drum Filler technology involves a rotating cylinder at the bottom of a powder hopper. An example includes the Omnidose TT (Harro Hofliger). Another technology is the Vacuum Dosator technology. This uses vacuum compaction to secure powder within a dosing tube prior to discharging the dry powder into a capsule. An example of this is the ModU C with the vacuum dosator system (Harro Hofliger). A further example is the Tamp filling technology. This relies upon tamping pins that push up and down within a powder bed so that a unit dose is transferred into a dosing disc. The dosing disk is then ejected into the capsule body. Another technology is the 'Pepper-shaker' or 'Pepper-pot' principle technology. This system works on the principle that when an inverted pepper shaker is tapped it will dispense a uniform amount of powder on each occasion that the container is tapped. An example of this is the Xcelodose. In a preferred embodiment, the Vacuum Dosator technology or the Vacuum Drum Filler technology is used.

In one aspect of the invention, the dry powder containing dry particles may be used with capsules. The dry powder containing dry particles, in one aspect, may be used to form the pellets that will go into the capsules. In another aspect, it may be directly fed into the capsule. The dry powder containing dry particles may be coated, as described, either directly as particles, as a pellet, or already formed in the capsule. The capsule may additionally contain therapeutic agents and/or one or more excipients. These may be present together with the dry powder comprising dry particles, e.g., in the pellet, or can be separately added to the capsule, e.g., as separate pellets.

Nasal Administration. For application to the nasal mucosa, nasal sprays are suitable compositions for use according to the invention. In a typical nasal formulation, the therapeutic agent, optionally comprising an excipient is present in the form of a dry powder optionally dispersed in a suitable solvent.

Nasal administration may be employed in those cases where an immediate effect is desired. Furthermore, after administration of a nasal formulation according to the invention, the therapeutic agent may be adsorbed on the nasal mucosa.

Processability Parameters

An overview of processability parameters include: i) the ability to fill a relatively small receptacle which holds a unit dose with the dry powder, ii) the ability to fill a relatively low filling mass with the dry powder, iii) the ability to use a metered dosing device on a reservoir-based DPI, and further, iv) the ability to rapidly fill a capsule or blister with the dry powder. For all of these parameters, an assessment for how processable the dry powder is would be if it meets the target parameter, e.g., a certain fill weight or metered dose, about 80% of the time or greater, about 85% of the time or greater, about 90% of the time or greater, about 95% of the time or greater, within an interval around the target weight of between about 80% to about 120%, between about 85% to about 115%, between about 90% to about 110%, between about 95% to about 105%. Particular processability performance parameters are described herein. Supra.

Exemplary Articles of Manufacture

In some aspects, the invention provides an article of manufacture. In some embodiments, the article comprising, a sealed receptacle that has a volume of about 12 cubic millimeters ($mm^3$) or less, about 9 $mm^3$ or less, about 6 $mm^3$ or less, about 3 $mm^3$ or less, about 1 $mm^3$ or less, about 0.5 $mm^3$ to about 0.1 $mm^3$, with a respirable dry powder disposed therein, wherein the respirable dry powder comprises respirable dry particles, the respirable dry particles comprising a) one or more metal cation salts, such as a sodium salt, a potassium salt, a magnesium salt, a calcium salt, or a combination thereof, and b) one or more therapeutic agents; wherein the one or more therapeutic agents provide at least about 25%, at least about 35%, at least about 50%, at least about 65%, at least about 80%, between about 85% and about 99%, of the total mass contained in the sealed receptacle; and the respirable dry particles have a volume median geometric diameter (VMGD) about 10 microns or less, about 7 micrometers or less, between about 5 micrometers and about 0.5 micrometers, or between about 3 micrometers and about 1 micrometer, and a tap density at least about 0.45 g/cc, at least about 0.55 g/cc, at least about 0.65 g/cc, between about 0.45 g/cc and about 1.2 g/cc, between about 0.55 g/cc and about 1.1 g/cc, between about 0.65 g/cc and about 1 g/cc.

In some embodiments, the article comprises, 1) a sealed receptacle and 2) contents disposed within the sealed receptacle, wherein the contents comprise a respirable dry powder and the contents are characterized by a mass, wherein the respirable dry powder comprises respirable dry particles, the respirable dry particles comprising a) one or more metal cation salts, such as a sodium salt, a potassium salt, a magnesium salt, a calcium salt, or a combination thereof, and b) one or more therapeutic agents; wherein the one or more therapeutic agents provide at least about 25%, at least about 35%, at least about 50%, at least about 65%, at least about 80%, between about 85% and about 99%, of the total mass contained in the sealed receptacle; and the respirable dry particles have a volume median geometric diameter (VMGD) about 10 microns or less, about 7 micrometers or less, between about 5 micrometers and about 0.5 micrometers, or between about 3 micrometers and about 1 micrometer, and a tap density at least about 0.45 g/cc, at least about 0.55 g/cc, at least about 0.65 g/cc, between about 0.45 g/cc and about 1.2 g/cc, between about 0.55 g/cc and about 1.1 g/cc, between about 0.65 g/cc and about 1 g/cc.

In another aspect, the invention is a dry powder inhaler comprising, a reservoir that is operatively coupled to a dosing mechanism, with a respirable dry powder disposed in the reservoir, wherein the dosing mechanism has one or more receptacles for containing a unit dose, wherein the volume of each receptacle is 100 cubic millimeters ($mm^3$) or less, 75 $mm^3$ or less, 50 $mm^3$ or less, 35 $mm^3$ or less, 20 $mm^3$ or less, 10 $mm^3$ or less, 5 $mm^3$ or less, or 2.5 $mm^3$ or less; the respirable dry powder comprises respirable dry particles, the respirable dry particles comprising a) one or more metal cation salts, and b) one or more therapeutic agents; wherein the one or more therapeutic agents provide at least about 25% of the total mass contained in the reservoir; and the respirable dry particles have a volume median geometric diameter (VMGD) about 10 micrometers or less, and a tap density at least about 0.45 g/cc.

Therapeutic Uses

In some aspects, the invention provides method for treating a disease or condition, comprising administering to a subject in need thereof an effective amount of the formulations described herein. Any desired disease or condition can be treated using dry powders that contain the appropriate therapeutic agents. The dry powders and articles of manufacture described herein can be used, for example, in the various therapeutic uses disclosed in paragraphs 211-222 of International Patent Application No. PCT/US2001/053829, filed on Sep. 29, 2011, and titled "Monovalent Metal Cation Dry Powders", which is incorporated by reference herein.

Administration to the respiratory tract can be for local activity of the delivered therapeutic agent or for systemic activity. For example, the respirable dry powders can be administered to the nasal cavity or upper airway to provide, for example, anti-inflammatory, anti-viral, or anti-bacterial activity to the nasal cavity or upper airway. The respirable dry powders can be administered to the deep lung to provide local activity in the lung or for absorption into the systemic circulation. Systemic delivery of certain therapeutic agents via the lung is particularly advantageous for agents that undergo substantial first pass metabolism (e.g., in the liver) following oral administration.

The respirable dry powders and respirable dry particles of the present invention may also be administered to the buccal cavity. Administration to the buccal cavity can be for local activity of the delivered therapeutic agent or for systemic activity. For example, the respirable dry powders can be administered to the buccal cavity to provide, for example, anti-inflammatory, anti-viral, or anti-bacterial activity to the buccal cavity.

The dry powders and dry particles of the invention can be administered to a subject in need thereof for systemic delivery of a therapeutic agent, such as to treat an infectious disease or metabolic disease.

The dry powders and dry particles of the invention can be administered to a subject in need thereof for the treatment of respiratory (e.g., pulmonary) diseases, such as respiratory syncytial virus infection, idiopathic fibrosis, alpha-1 antitrypsin deficiency, asthma, airway hyperresponsiveness, seasonal allergic allergy, brochiectasis, chronic bronchitis, emphysema, chronic obstructive pulmonary disease, cystic fibrosis and the like, and for the treatment and/or prevention of acute exacerbations of these chronic diseases, such as exacerbations caused by viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Burkholderis* ssp., *Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, including pollen and cat dander, airborne particulates, and the like).

The dry powders and dry particles of the invention can be administered to a subject in need thereof for the treatment and/or prevention and/or reducing contagion of infectious diseases of the respiratory tract, such as pneumonia (including community-acquired pneumonia, nosocomial pneumonia (hospital-acquired pneumonia, HAP; health-care associated pneumonia, HCAP), ventilator-associated pneumonia (VAP)), ventilator-associated tracheobronchitis (VAT), bronchitis, croup (e.g., postintubation croup, and infectious croup), tuberculosis, influenza, common cold, and viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, airborne particulates, and the like).

In some aspects, the invention provides a method for treating a pulmonary diseases, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention provides a method for the treatment or prevention of acute exacerbations of a chronic pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In some aspects, the invention provides a method for the treatment or prevention of cardiovascular disease, autoimmune disorders, transplant rejections, autoimmune disorders, allergy-related asthma, infections, and cancer. For example, the invention provides a method for the treatment or prevention of postmenopausal osteoporosis, cryopyrin-associated periodic syndromes (CAPS), paroxysmal nocturnal hemoglobinuria, psoriasis, rheumatoid arthritis, psoriatic arthritis, ankylosing spondylitis, multiple sclerosis, and macular degeneration. For example, dry powders or dry particles of the invention are co-formulated or blended with therapeutic antibodies as described herein. The co-formulated or blended dry powders may then be administered to a subject in need of therapy or prevention.

In certain aspects, the invention provides a method for the treatment or prevention of cancer such as acute myeloid leukemia, B cell leukemia, non-Hodgkin's lymphoma, breast cancer (e.g. with HER2/neu overexpression), glioma, squamous cell carcinomas, colorectal carcinoma, anaplastic large cell lymphoma (ALCL), Hodgkin lymphoma, head and neck cancer, acute myelogenous leukemia (AML), melanoma, and chronic lymphocytic leukemia (CLL). Alternatively or in addition, the invention provides a method for the treatment or prevention of cancer by anti-angiogenic cancer therapy. For example, dry powders or dry particles of the invention are co-formulated or blended with therapeutic antibodies as described herein. Therapeutic antibodies can be cancer-specific antibodies, such as a humanized monoclonal antibody, e.g. gemtuzumab, alemtuzumab, trastuzumab, nimotuzumab, bevacizumab, or a chimeric monoclonal antibody, e.g. rituximab and cetuximab. The co-formulated or blended dry powders may then be administered to a subject in need of therapy or prevention.

In certain aspects, the invention provides a method for the treatment or prevention of inflammation such as rheumatoid arthritis, Crohn's disease, ulcerative Colitis, acute rejection of kidney transplants, moderate-to-severe allergic asthma. For example, dry powders or dry particles of the invention are co-formulated or blended with therapeutic antibodies as described herein. Therapeutic antibodies can be inflammation-specific antibodies, such as chimeric monoclonal antibodies, e.g. infliximab, basiliximab, humanized monoclonal antibodies, e.g. daclizumab, omalizumab, or human antibodies, e.g. adalimumab. The co-formulated or blended dry powders may then be administered to a subject in need of therapy or prevention.

In certain aspects, the invention provides a method for the treatment or prevention of RSV infections in children. For example, dry powders or dry particles of the invention are co-formulated or blended with therapeutic antibodies as described herein. Therapeutic antibodies can be RSV infection-specific antibodies, such as the humanized monoclonal antibody palivizumab which inhibits an RSV fusion (F) protein. The co-formulated or blended dry powders may then be administered to a subject in need of RSV infection therapy or prevention.

In certain aspects, the invention provides a method for the treatment or prevention of diabetes. For example, dry powders or dry particles of the invention are co-formulated or blended with insulin as described herein. The co-formulated or blended dry powders may then be administered to a subject in need of insulin therapy or prevention.

The respirable dry particles or dry powders can be delivered by inhalation to tract, as desired. It is well-known that particles with an aerodynamic diameter of about 1 micron to about 3 microns, can be delivered to the deep lung. Larger aerodynamic diameters, for example, from about 3 microns to about 5 microns can be delivered to the central and upper airways.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g. above 5 um, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 microns or less), the size distribution of the inhaled powder may have an MMAD of greater than 5 µm, leading to enhanced oral cavity deposition.

Therefore, it is desirable to have a powder in which the particles are small (e.g., MMAD of 5 microns or less, e.g. between 1 to 5 microns), and are highly dispersible (e.g. 1 bar/4 bar or alternatively, 0.5 bar/4 bar of 2.0, and preferably less than 1.5). More preferably, the respirable dry powder is comprised of respirable dry particles with an MMAD between 1 to 4 microns or 1 to 3 microns, and have a 1 bar/4 bar less than 1.4, or less than 1.3, and more preferably less than 1.2.

The absolute geometric diameter of the particles measured at 1 bar using the HELOS system is not critical provided that the particle's envelope mass density is sufficient such that the MMAD is in one of the ranges listed above, wherein MMAD is VMGD times the square root of the envelope mass density (MMAD=VMGD*sqrt(envelope mass density)). If it is desired to deliver a high unit dose of therapeutic agent using a fixed volume dosing container, then, particles of higher envelop density are desired. High envelope mass density allows for more mass of powder to be contained within the fixed volume dosing container. Preferable envelope mass densities are greater than 0.1 g/cc, greater than 0.25 g/cc, greater than 0.4 g/cc, greater than 0.5 g/cc, greater than 0.6 g/cc, greater than 0.7 g/cc, and greater than 0.8 g/cc.

The respirable dry powders and particles of the invention can be employed in compositions suitable for drug delivery via the respiratory system. For example, such compositions can include blends of the respirable dry particles of the invention and one or more other dry particles or powders, such as dry particles or powders that contain another therapeutic agent, or that consist of or consist essentially of one or more pharmaceutically acceptable excipients.

Respirable dry powders and dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry powders or particles deposit in the deep lung.

In another embodiment of the invention, delivery is primarily to the central airways. In another embodiment, delivery is to the upper airways.

The respirable dry particles or dry powders of the invention can be delivered by inhalation at various parts of the breathing cycle (e.g., laminar flow at mid-breath). An advantage of the high dispersibility of the dry powders and dry particles of the invention is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The highly dispersible powders of the invention can provide advantages for targeting the timing of drug delivery in the breathing cycle and also location in the human lung. Because the respirable dry powders of the invention can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate which diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Elsevier, Amsterdam (1985).

Suitable dosing to provide the desired therapeutic effect can be determined by a clinician based on the severity of the condition (e.g., infection), overall well being of the subject and the subject's tolerance to respirable dry particles and dry powders and other considerations. Based on these and other considerations, a clinician can determine appropriate doses and intervals between doses. Generally, respirable dry particles and dry powders are administered once, twice or three times a day, as needed.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

Another advantage provided by the respirable dry powders and respirable dry particles described herein, is that dosing efficiency can be increased as a result of hygroscopic growth of particles inside the lungs, due to particle moisture growth. The propensity of the partially amorphous, high salt compositions of the invention to take up water at elevated humidities can also be advantageous with respect to their deposition profiles in vivo. Due to their rapid water uptake at high humidities, these powder formulations can undergo hygroscopic growth do the absorbance of water from the humid air in the respiratory tract as they transit into the lungs. This can result in an increase in their effective aerodynamic diameters during transit into the lungs, which will further facilitate their deposition in the airways.

Stability of the Dry Powder and of the Solid Dosage Form

In an aspect of the current invention, the Respirable Dry Powders provide advantages to enhance the stability of Respirable Therapeutic agents. Enhanced stability may be achieved: (i) during the formation of a Respirable Dry Powder, (ii) during storage of the Respirable Dry Powder, (iii) during the formation of a Dosage Form, and/or (iv) during the storage of the Dosage Form.

The enhancement in stability can be observed in at least one of the following scenarios: First, in the chemical integrity of the therapeutic agent, during production of the Respirable Dry Powder and/or during production of the Dosage Form. Second, in the chemical integrity of the Therapeutic agent during storage of the Respirable Dry Powder and/or during storage of the Dosage Form. Third, in the physical properties of the Respirable Dry Powder during production of the Respirable Dry Power and/or during storage of the dry powder, these physical properties include, for example, geometric diameter, flowability, and density. Fourth, in the physical properties of the Dosage Form during production and/or during storage of the Dosage Form, these physical properties include, for example, dosage form integrity.

Certain Preferred Respirable Dry Powders

In some aspects, the respirable dry powder comprises respirable dry particles that comprise a monovalent or divalent metal cation salt, e.g., a sodium salt, a potassium salt, a magnesium salt, a calcium salt, or any combination thereof, one or more therapeutic agents, and optionally an excipient, where the respirable dry particles comprise:

a) about 20% (w/w) to about 90% (w/w) a monovalent or divalent metal cation salt, and about 0.01% (w/w) to about 20% (w/w) therapeutic agent;

b) about 20% (w/w) to about 80% (w/w) a monovalent or divalent metal cation salt, and about 20% (w/w) to about 60% (w/w) therapeutic agent; or c) about 5% (w/w) to about 40% (w/w) a monovalent or divalent metal cation salt, and about 60% (w/w) to about 95% (w/w) therapeutic agent; wherein all components of the respirable dry particles amount to 100 weight %, and wherein the respirable dry particles have a volume median geometric diameter (VMGD) of 10 microns or less, a dispersibility ratio (1/4 bar) of 2.0 or less as measured by laser diffraction (RODOS/HELOS system), and a tap density of about 0.4 g/cc to about 1.2 g/cc, or of at least 0.45 g/cc. In a further aspect, the a monovalent or divalent metal cation is at least 3% (w/w), or at least 5% (w/w).

In other aspects, the respirable dry powder comprises respirable dry particles that comprise at least about 3% (w/w) a monovalent or divalent metal cation, and a) about 5% to about 45% excipient, about 20% to about 90% a monovalent or divalent metal cation salt, and about 0.01% to about 20% therapeutic agent;

b) about 0.01% to about 30% excipient, about 20% to about 80% a monovalent or divalent metal cation salt, and about 20% to about 60% therapeutic agent; or c) about 0.01% to about 20% excipient, about 20% to about 60% a monovalent or divalent metal cation salt, and about 60% to about 99% therapeutic agent, wherein the respirable dry particles have a volume median geometric diameter (VMGD) of 10 microns or less, a dispersibility ratio (0.5/4 bar) of 2.2 or less as measured by laser diffraction (RODOS/HELOS system), and a tap density of about 0.4 g/cc to about 1.2 g/cc. Alternatively, the a monovalent or divalent metal cation is at least about 5% (w/w).

Levofloxacin Powders

Inhaled antibiotics enable delivery of high drug concentrations directly to the site of respiratory infections. Certain antibiotics such as tobramycin, aztreonam, and colistin are currently administered by inhalation to treat bacterial infections in respiratory diseases, e.g. in cystic fibrosis. Many patients with non-CF bronchiectasis (NCFBE) become chronically colonized with bacterial pathogens leading to increased risk of exacerbation of the underlying NCFBE. Inhalable formulations of Levofloxacin would provide an alternative class of antibiotics that may be used in the treatment and/or prevention of bacterial infections in respiratory diseases such as CF and NCFBE. Liquid aerosol formulations of levofloxacin have been described. Dry powder formulations containing levofloxacin would provide more convenient solutions concerning the delivery of the drug to the subject.

The invention, in certain aspects, also relates to dry powder compositions comprising levofloxacin, receptacles and dry powder inhalers comprising such powders, and methods of treating or preventing respiratory diseases (e.g. bacterial infections or exacerbations induced by bacterial infections) comprising administering the dry powder compositions comprising levofloxacin described herein to a subject in need thereof. Additional aspects of the invention relate to the process of manufacturing (including filling) of articles, described herein, comprising dry powder compositions comprising levofloxacin.

The dry powder compositions comprising levofloxacin may comprise or more preferably consist of respirable dry particles described herein. Preferably, the respirable dry particles comprise levofloxacin as a therapeutic agent, one or more metal cation salts which are each individually selected from the group consisting of monovalent metal cation salts, divalent metal cation salts, and combinations thereof, and optionally, one or more excipients (e.g. leucine and maltodextrin). The respirable dry particles may comprise between about 10% and about 90% (w/w) levofloxacin, preferably, between about 20% and about 90% (w/w), more preferably, between about 50% and about 90% (w/w), and most preferably, between about 70% and about 90% (w/w) levofloxacin. In a preferred embodiment, the respirable dry particles comprise no more than about 90% levofloxacin (<90% w/w). Generally, relatively high doses of antibiotics, such as levofloxacin need to be delivered to the respiratory tract to be efficacious for reducing the microbial burden. Dry powders comprising respirable dry particles which comprise high loads of levofloxacin, e.g. about 50%, about 60%, about 70%, about 80%, and about 90% (on a weight basis) are particularly preferred for administration of the antibiotic to the respiratory tract. In a particularly preferred embodiment, the respirable dry particles comprise between about 70% and about 90% (w/w) levofloxacin, e.g. about 70% (w/w) levofloxacin, about 75% (w/w) levofloxacin, about 80% (w/w) levofloxacin, about 82% (w/w) levofloxacin, about 85% (w/w) levofloxacin, or about 90% (w/w) levofloxacin. In preferred embodiments, the respirable dry particles comprise one or more metal cation salts selected from the group consisting of monovalent metal cation salts, divalent metal cation salts, and combinations thereof, and optionally, one or more excipients, wherein the selected salts and/or excipients are soluble or highly soluble in water. It is particularly preferred that the monovalent cation salt, the divalent cation salt and/or the excipient are selected from a group consisting of soluble or highly soluble salts and/or excipients, if desired for making respirable dry particles comprising levofloxacin, as described herein, e.g. by spray-drying. Specifically preferred moderately soluble or highly soluble salts and excipients include the salts sodium chloride and magnesium lactate as well as the excipients leucine and other amino acids, such as, for example alanine, maltodextrin, mannitol, and trehalose. Other moderately soluble or highly soluble sodium salts and magnesium salts may also be selected and may include suitable, soluble or highly soluble, chloride, lactate, citrate, and sulfate sodium or magnesium salts. In certain embodiments, dry powders comprising respirable dry particles that comprise levofloxacin and salts and/or excipients that exhibit low water solubility (e.g., solubility in distilled water at room temperature (20-30° C.) and 1 bar of no more than 0.9 g/L, no more than 5 g/L, no more than 10 g/L, or no more than 20 g/L) are specifically excluded, thus, aspects of the invention relate to dry powders comprising respirable dry particles that comprise levofloxacin and that do not comprise salts and/or excipients that exhibit low water solubility. In preferred embodiments, the monovalent metal cation salt is a sodium salt, specifically sodium chloride. In another preferred embodiment, the divalent metal cation salt is a magnesium salt, specifically magnesium lactate. Preferred excipients, if desired, are leucine and maltodextrin. In certain embodiments, the levofloxicin dry particles do not contain one or more of the following metal cation salts: magnesium chloride, magnesium sulfate, magnesium carbonate, magnesium stearate, calcium chloride, dicalcium phosphate, sodium saccharine, sodium crosscarmellose, sodium acetate, or sodium citrate. When the levoflocixin dry particles of these embodiments include an excipient, the particles do not contain one or more of mannitol, lactose, starch, talcum, cellulose, glucose, gelatin, sucrose, cyclodextrin derivatives, sorbitan monolaurate, triethanolamine acetate, triethanolaminie oleate, gum acacia, polyvinylpyrrolidine. In other embodiments, the levofloxicin dry particles do not contain one or more of mannitol, lactose, starch, talcum, cellulose, glucose, gelatin, sucrose, cyclodextrin derivatives, sorbitan monolaurate, triethanolamine acetate, triethanolaminie oleate, gum acacia, polyvinylpyrrolidine: If desired, in other embodiments including the embodiments that do not include certain excipients, the metal cation salt ist sodium chloride.

When the respirable dry particles comprise levofloxacin and both a metal cation salt and an excipient it is preferred that the respirable dry particles comprise the metal cation salt and the excipient in a ratio of about 1:2 (metal cation salt:excipient, on a weight basis). In other embodiments, the ratio of sodium salt to excipient is about 1:1 or about 2:1 (weight:weight). In yet other embodiments, the ratio of sodium salt to excipient is from about 1:1 to about 1:2 or from about 1:1 to about 2:1 (weight:weight). In a specifically preferred embodiment, the metal cation salt is a monovalent salt. For example, the monovalent salt is sodium chloride. Alternatively, the monovalent salt is sodium citrate or sodium sulfate.

In another embodiment, when the respirable dry particles comprise levofloxacin and both a metal cation salt and an excipient it is preferred that the respirable dry particles comprise the metal cation salt and the excipient in a ratio of about 5:1 (metal cation salt:excipient on a weight basis). In other embodiments, the ratio of magnesium salt to excipient is about 4:1, about 3:1, about 2:1 or about 1:1 (weight:weight). In yet other embodiments, the ratio of magnesium salt to excipient is from about 1:1 to about 5:1 or from about 1:1 to about 1:5 (weight:weight). It is particularly preferred that the metal cation salt is a divalent salt. For example, the divalent salt is magnesium lactate, magnesium citrate or magnesium sulfate. Preferably, the metal cation salt is between about 3% and about 80% (w/w) of the respirable particle, more preferably, between about 3% and 30%, and most preferably, between about 5% and 30% (w/w).

In certain embodiments, the respirable dry particles do not contain an excipient (0% w/w). In other embodiments, the excipient is between about 1% and about 30%, preferably between about 1% and about 25%, most preferably, between about 5% and about 15%. In a specific embodiment, the excipient is about 5% (w/w).

Generally, the dry powder compositions may comprise respirable dry particles consisting of about 20% to about 90% levofloxacin, a monovalent or divalent metal cation salt of about 3% to about 80% and an optional excipient of about 0% to about 77%. Optionally, the respirable dry particles further comprise one or more therapeutic agents in addition to levofloxacin. Preferably, the respirable dry particles have a volume median geometric diameter (VMGD) about 10 micrometers or less, and a tap density at least about 0.45 g/cc.

An exemplary dry powder composition comprising respirable dry particles comprising levofloxacin, a monovalent salt and an excipient in a ratio of about 1:2 (metal cation salt:excipient on a weight basis) is Formulation IX, consisting of 82% levofloxacin, 6.3% sodium chloride, and 11.7% leucine.

An exemplary dry powder composition comprising respirable dry particles comprising levofloxacin, a divalent salt and an excipient in a ratio of about 5:1 (metal cation salt:excipient, on a weight basis) are Formulation XIX, consisting of 70% levofloxacin, 25% magnesium lactate, and 5% leucine, and Formulation XX consisting of 70% levofloxacin, 25% magnesium lactate, and 5% maltodextrin.

An exemplary dry powder composition comprising respirable dry particles comprising levofloxacin, a divalent salt without the optional excipient is Formulation XXI, consisting of 75% levofloxacin and 25% magnesium lactate.

The inventors produced and analyzed a large number of dry powder formulations comprising levofloxacin in a range of 0% to 100% (w/w of the respirable dry particle), comprising monovalent metal cation salts (including potassium chloride, sodium chloride, sodium citrate and sodium sulfate) or divalent metal cation salts (including magnesium lactate, magnesium chloride, magnesium citrate, magnesium sulfate, calcium chloride, calcium acetate, and calcium lactate) in the range of 3% to 60% (w/w of the respirable dry particle) and optionally combined with an excipient (including leucine and other amino acids, such as, for example alanine, mannitol and maltodextrin) in the range of 0% to 66.5% (w/w of the respirable dry particle) for their physical powder properties, aerosol properties and stability characteristics. While most particles were geometrically small by HELOS/RODOS large divergence in performance occurred for the various dry powder compositions using several parameters. For example, in a study in which dry powders were produced and analyzed that comprise divalent metal cation salts, the performance of the powders in various assays ranged from 8% to 67.9% for FPFTD<5.6 microns in ACI-2 testing; 31% to 99% in Spraytec CEPM testing at 20 sLPM, and ranged from 87% to 100% in Spraytec CEPM testing at 60 sLPM. The size of the particles ranged from 2.6 microns to 62 microns in Spraytec Dv50 testing at 20 sLPM, and from 1.89 microns to 47 microns in Spraytec Dv50 testing at 60 sLPM. The glass transition temperature ranged from 59° C. to 108° C. (Tg wet) for DSC analysis; and TGA water loss ranged from 1.48% to 11% for the various divalent metal cation dry powder compositions tested. The most preferred levofloxacin-containing dry powders comprise particles that have one or more of the following characteristics: a) ACI-2: FPFTD<5.6 microns>50%; b) dispersibility measured by Spraytec: CEPM at 60 LPM>90% and CEPM at 20 LPM>80%; c) small particles: Dv50 <5 microns across flow rates; d) RODOS/HELOS dispersibility in bulk across pressures <5 microns; e) tapped density >0.4 g/cc; and/or f) glass transition temperature >70° C.

Surprisingly, it was found that certain dry powder formulations comprising a high load of levofloxacin (e.g. dry powders comprising from about 70% to about 90% levofloxacin (w/w)) and a metal cation salt (e.g. a monovalent metal cation salt such as sodium or a divalent metal cation salt such as magnesium) exhibited powder characteristics that were superior to dry powders that consisted of levofloxacin (100% spray-dried levofloxacin). The formulations comprising levofloxacin and a metal cation salt exhibited flow rate independence when CEPM and VMD were measured while 100% levofloxacin dry powders displayed high flow rate dependency. The formulations comprising levofloxacin and a metal cation salt exhibited complete capsule emission across high capsule fill weights from 40 mg up to 120 mg. An exemplary dry powder composition comprising respirable dry particles comprising levofloxacin and a monovalent metal cation salt is Formulation IX, consisting of 82% levofloxacin, 6.3% sodium chloride, and 11.7% leucine.

Further, it was surprisingly found that certain dry powder formulations comprising a high load of levofloxacin (e.g. dry powders comprising from about 50% to about 90% levofloxacin (w/w)) and a divalent metal cation salt (e.g. magnesium and calcium) exhibited high glass transition temperatures (Tg). Certain formulations, e.g. those comprising magnesium salts exhibited glass transition temperatures from about 80° C. to about 140° C. Dry powder formulations comprising a high load of levofloxacin (e.g. dry powders comprising from about 70% to about 90% levofloxacin (w/w)) and a monovalent (sodium) metal cation salt generally exhibit lower glass transition temperatures of about 65° C. to about 70° C. High glass transition temperatures are generally predictive of and may be related to the physical stability of a composition. Unstable dry powder compositions may, for example, exhibit a glass transition temperature of less than 50° C. above storage condition, e.g., when stored at 20 or 25° C., an unstable Tg would be less than 70 or 75° C. An unstable dry powder composition may be characterized, for example, by particle agglomeration or re-crystallization events over time. It was found that certain powder formulations comprising a high load of levofloxacin and magnesium salts did not exhibit particle agglomeration and/or re-crystallization events over a period of time, e.g. two weeks, preferably under accelerated storage conditions, such as elevated temperature and/or high humidity. Exemplary dry powder composition comprising respirable dry particles comprising levofloxacin, a divalent salt without an optional excipient that exhibit high glass transition temperatures are Formulation XIX, consisting of 70% levofloxacin, 25% magnesium lactate, and 5% leucine; Formulation XX consisting of 70% levofloxacin, 25% magnesium lactate, and 5% maltodextrin and Formulation XXI, consisting of 75% levofloxacin and 25% magnesium lactate. Other powders that exhibit high glass transition temperatures are Formulation XXII consisting of 55% levofloxacin, 25% magnesium lactate, and 20% maltodextrin; and Formulation XXIII consisting of 55% levofloxacin and 10% magnesium lactate and 35% maltodextrin.

While not wishing to be bound by any particular theory, inventors believe that the divalent cations provided by the divalent metal cation salts provide a chelation effect that enhances the thermal stability of the levofloxacin in the dry powder formulation resulting in a higher glass transition temperature and greater stability of the formulation, yet the chelation effect does not negatively affect the antimicrobial properties of levofloxacin, e.g. when tested in vitro against bacterial strains and in vivo in mice infected with bacteria. The most preferred levofloxacin-containing dry powders described herein are relatively stable (e.g. tested under accelerated storage conditions) and biologically active (e.g. tested as antimicrobial activity against certain bacteria strains).

One preferred dry powder composition is Formulation IX, consisting of 82% levofloxacin, 6.3% sodium chloride, and 11.7% leucine. The particles exhibit a volumetric size distribution that is independent of the primary (dispersion) pressure, e.g. the x50% is 1.90 microns for 0.5 bar primary pressure, 1.70 microns for 1.0 bar, and 1.62 microns for 4.0 bar, respectively. The GSD is 2.30 at 0.5 bar, 2.28 at 1.0 bar, and 2.31 at 4.0 bar, respectively. Formulation IX has a 1/4 bar ratio of 0.96 and a 0.5/4 bar ratio of 1.07. The formulation is highly dispersible across flow rates, e.g. the formulation exhibits a CEPM of >94%, a VMD of 2.87 microns and a GSD of 2.46 at 15 sLPM; and a VMD of 1.56 microns and a GSD of 3.01 at 60 sLPM. The formulation is dense, exhibiting a bulk density of 0.33 g/cc and a tap density (USP1) of 0.82 g/cc, respectively. The formulation has a low water content of about 2.4%. The MMAD is in the respirable range, about 4.79 microns, shows low capsule and DPI retention and low IP deposition.

Another preferred dry powder composition is Formulation XIX, consisting of 70% levofloxacin, 25% magnesium lactate, and 5% leucine. Formulation XIX exhibits a CEPM of 63% and a Dv50 of 2.83 microns at 20 sLMP; and a CEPM of 97% and a DV50 of 2.25 microns at 60 sLMP, respectively. Formulation XIX has a 1/4 bar ratio of 1.02 and a 0.5/4 bar ratio of 1.08. The GSD is 2.05 at 0.5 bar, 2.12 at 1.0 bar, and 2.14 at 4.0 bar, respectively. The MMAD is in the respirable range, about 4.42 microns.

Another preferred dry powder composition is Formulation XX consisting of 70% levofloxacin, 25% magnesium lactate, and 5% maltodextrin. Formulation XX exhibits a CEPM of 93% and a Dv50 of 2.59 microns at 20 sLMP; and a CEPM of 100% and a DV50 of 2.21 microns at 60 sLMP, respectively. Formulation XIX has a 1/4 bar ratio of 1.07 and a 0.5/4 bar ratio of 1.27. The GSD is 2.01 at 0.5 bar, 1.98 at 1.0 bar, and 2.03 at 4.0 bar, respectively. The MMAD is in the respirable range, about 4.19 microns.

Another preferred dry powder composition is Formulation XXIV consisting of 65% levofloxacin and 25% magnesium lactate, and 10% leucine. The formulation has a HELOS/RODOS ×50 at 1 bar of 1.89 microns, a tap density of 0.7 g/cc, a ACI-2 FPF TD<5.6 microns of 53.5%, a CEPM at 60 sLPM of 98%, a CEPM at 20 sLPM of 95%, a Dv50 at 20 sLPM of 2.56 microns, a Dv50 at 60 sLPM of 2.07 microns, a DSC (Tg) of 95.3° C., and a DSC (Tc) of 130° C.

Another preferred dry powder composition is Formulation XXV consisting of 65% levofloxacin and 25% magnesium lactate, and 10% maltodextrin. The formulation has a HELOS/RODOS ×50 at 1 bar of 2.00 microns, a tap density of 0.58 g/cc, a ACI-2 FPF TD<5.6 microns of 52.57%, a CEPM at 60 sLPM of 93%, a CEPM at 20 sLPM of 63%, a Dv50 at 20 sLPM of 2.52 microns, a Dv50 at 60 sLPM of 2.12 microns, a DSC (Tg) of 92° C., and a DSC (Tc) of 121.5° C.

Another preferred dry powder composition is Formulation XXVI consisting of 65% levofloxacin and 25% magnesium lactate, and 10% alanine. The formulation has a HELOS/RODOS ×50 at 1 bar of 1.98 microns, a tap density of 0.64 g/cc, a ACI-2 FPF TD<5.6 microns of 44.58%, a CEPM at 60 sLPM of 95%, a CEPM at 20 sLPM of 73%, a Dv50 at 20 sLPM of 2.56 microns, a Dv50 at 60 sLPM of 2.07 microns.

Another preferred dry powder composition is Formulation XXVII consisting of 65% levofloxacin and 25% magnesium lactate, and 10% mannitol. The formulation has a HELOS/RODOS ×50 at 1 bar of 1.73 microns, a tap density of 0.64 g/cc, a ACI-2 FPF TD<5.6 microns of 50.67%, a CEPM at 60 sLPM of 84%, a CEPM at 20 sLPM of 60%, a Dv50 at 20 sLPM of 2.51 microns, a Dv50 at 60 sLPM of 1.84 microns.

Another preferred dry powder composition is Formulation XXI consisting of 75% levofloxacin and 25% magnesium lactate. The formulation has a HELOS/RODOS ×50 at 1 bar of 2.03 microns, a ACI-2 FPF TD<5.6 microns of 43.1%, a Dv50 at 20 sLPM of 2.63 microns, a Dv50 at 60 sLPM of 2.18 microns, a CEPM at 20 sLPM of 76%, a CEPM at 60 sLPM of 90%, a DSC (Tg) of 107.1° C., and a DSC (Tc) of 108.2° C.

Another preferred dry powder composition is Formulation XXVIII consisting of 75% levofloxacin and 25% sodium sulfate. The formulation has a HELOS/RODOS ×50 at 1 bar of 1.75 microns, a ACI-2 FPF TD<5.6 microns of 47.6%, a Dv50 at 20 sLPM of 4.43 microns, a Dv50 at 60 sLPM of 1.92 microns, a CEPM at 20 sLPM of 90%, a CEPM at 60 sLPM of 95%, a DSC (Tg) of 67.5° C., and a DSC (Tc) of 78.9° C.

Another preferred dry powder composition is Formulation XXIX consisting of 75% levofloxacin and 25% sodium citrate. The formulation has a HELOS/RODOS ×50 at 1 bar of 1.62 microns, a ACI-2 FPF TD<5.6 microns of 53.07%, a Dv50 at 20 sLPM of 2.27 microns, a Dv50 at 60 sLPM of 1.72 microns, a CEPM at 20 sLPM of 81%, a CEPM at 60 sLPM of 92%, a DSC (Tg) of 65.8° C., and a DSC (Tc) of 81.5° C.

Another preferred dry powder composition is Formulation XXX consisting of 75% levofloxacin and 25% calcium acetate. The formulation has a HELOS/RODOS ×50 at 1 bar of 2.23 microns, a ACI-2 FPF TD<5.6 microns of 46.96%, a Dv50 at 20 sLPM of 2.63 microns, a Dv50 at 60 sLPM of 2.42 microns, a CEPM at 20 sLPM of 75%, a CEPM at 60 sLPM of 95%, a DSC (Tg) of 129.7° C., and a DSC (Tc) not detected.

Another preferred dry powder composition is Formulation XXXI consisting of 75% levofloxacin and 25% potassium chloride. The formulation has a HELOS/RODOS ×50 at 1 bar of 1.63 microns, a ACI-2 FPF TD<5.6 microns of 44.08%, a Dv50 at 20 sLPM of 2.72 microns, a Dv50 at 60 sLPM of 1.81 microns, a CEPM at 20 sLPM of 92%, a CEPM at 60 sLPM of 97%, a DSC (Tg) of 66° C., and a DSC (Tc) of 77.6° C.

Another preferred dry powder composition is Formulation XXXII consisting of 75% levofloxacin and 25% sodium chloride. Formulation XXXII has a FPF TD<3.4 microns of 36.85%, a FPF_TD<5.6 microns of 57.13%, a Dv50 (Spraytec) at 20 LPM of 2.56 microns, a Dv50 at 60 LPM of 1.84 microns, a GSD (Spraytec) at 20 LPM of 2.79 microns, a GSD at 60 LPM of 4.95 microns, a CEPM at 20 LPM of 95%, and a CEPM at 60 LPM of 98%.

Another preferred dry powder composition is Formulation XXXIII consisting of 75% levofloxacin and 25% calcium lactate. Formulation XXXIII has a FPF TD<3.4 microns of 33.14%, a FPF_TD<5.6 microns of 53.57%, a Dv50 (Spraytec) at 20 LPM of 3.18 microns, a Dv50 at 60 LPM of 2.24 microns, a GSD (Spraytec) at 20 LPM of 4.06 microns, a GSD at 60 LPM of 3.95 microns, a CEPM at 20 LPM of 76%, and a CEPM at 60 LPM of 94%.

Additional preferred dry powder compositions are: Formulation XXXIV consisting of 75% levofloxacin and 25% magnesium citrate, 75% levofloxacin and 25% magnesium sulfate, 75% levofloxacin and 25% magnesium chloride, and 75% levofloxacin and 25% calcium chloride.

In certain embodiments, dry powder compositions comprising respirable dry particles comprising levofloxacin are amorphous. In specific embodiments, the powder compositions comprising respirable dry particles comprising levofloxacin that are amorphous do not undergo a solid state change over time. For example, a change in solid state from amorphous to crystalline or partially crystalline. In certain embodiments, a change in solid change does not occur over the period of at least one week, at least two weeks, at least three weeks, at least four weeks, at least six weeks, at least eight weeks, at least ten weeks, or at least 12 weeks. In specific embodiments, a change in solid change does not occur over 1, 2, 3, 4, 5, 6, 7, 8, 9, 10 or 12 weeks if the powder is exposed to accelerated storage conditions, e.g. to elevated temperature (e.g. 30-40 C) and/or elevated humidity (e.g. 40-70% humidity).

In other embodiments, dry powder compositions comprising respirable dry particles comprising levofloxacin are crystalline or partially crystalline and partially amorphous. In specific embodiments, the powder compositions comprising respirable dry particles comprising levofloxacin that are crystalline or partially crystalline do not undergo a solid state change over time. In certain embodiments, a change in solid state does not occur over the period of at least one week, at least two weeks, at least three weeks, at least four weeks, at least six weeks, at least eight weeks, at least ten weeks, or at least 12 weeks. In specific embodiments, a change in solid state does not occur over 1, 2, 3, 4, 5, 6, 7, 8, 9, 10 or 12 weeks if the powder is exposed to accelerated storage conditions, e.g. to elevated temperature (e.g. 30-40° C.) and/or elevated humidity (e.g. 40-70% humidity).

The respirable dry powders comprising levofloxacin described herein are effective to kill bacteria cultures in vitro and to reduce bacterial load in the lungs of infected animals (e.g. mice experimentally infected with *K. pneumonia*). It was found that the chelating of levofloxacin by divalent metal cations (e.g. magnesium) did not inhibit its antibiotic activity. Provided herein are methods for treating bacterial infections in a subject, preferably bacterial infections of the respiratory tract, the method comprising administering to a subject in need thereof an effective amount of a dry powder comprising levofloxacin described herein.

Also provided herein are methods for preventing bacterial infection, preferably of the respiratory tract. Preferred subjects are humans exhibiting symptoms of or having been diagnosed with cystic fibrosis or non-CF bronchiectasis (NCFBE) who either currently are infected with bacteria, are susceptible of becoming infected or are susceptible of becoming chronically colonized with bacterial pathogens, the method comprising administering to a subject in need thereof an effective amount of a dry powder comprising levofloxacin described herein.

Also provided herein are methods for treating acute exacerbations resulting from bacterial infections, e.g. in a subject with CF, the method comprising administering to a subject in need thereof an effective amount of a dry powder comprising levofloxacin described herein.

The following examples serve to more fully describe the invention. It is understood that these examples in no way serve to limit the true scope of this invention, but rather are presented for illustrative purposes. All references cited herein are incorporated by reference in their entirety.

EXEMPLIFICATION

Methods:

Geometric or Volume Diameter. Volume median diameter (VMD) (×50), which may also be referred to as volume median geometric diameter (VMGD) and Dv(50), was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar with maximum orifice ring pressure) of the incoming compressed dry air. The pressure settings may be varied to vary the amount of energy used to disperse the powder. For example, the regulator pressure may be varied from 0.2 bar to 4.0 bar. Powder sample is dispensed from a microspatula into the RODOS funnel. The dispersed particles travel through a laser beam where the resulting diffracted light pattern produced is collected, typically using an R1 lens, by a series of detectors. The ensemble diffraction pattern is then translated into a volume-based particle size distribution using the Fraunhofer diffraction model, on the basis that smaller particles diffract light at larger angles. Using this method, geometric standard deviation (GSD) for the VMGD was also determined.

Fine Particle Fraction. The aerodynamic properties of the powders dispersed from an inhaler device were assessed with a Mk-II 1 ACFM Andersen Cascade Impactor (Copley Scientific Limited, Nottingham, UK). The instrument was run in controlled environmental conditions of 18 to 25° C. and relative humidity (RH) between 25 and 35%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain. Gravimetric or analytical analysis can then be performed to determine the particle size distribution.

The impaction technique utilized allowed for the collection of eight separate powder fractions. The capsules (Capsugel, Greenwood, S.C.) were filled with approximately 20, 40 or 50 mg powder and placed in a hand-held passive dry powder inhaler (DPI) device, the high resistance RS-01 DPI (Plastiape, Osnago, Italy). The capsule was punctured and the powder was drawn through the cascade impactor operated at a flow rate of 60.0 L/min for 2.0 seconds. At this flow rate, the calibrated cut-off diameters for the eight stages are 8.6, 6.5, 4.4, 3.3, 2.0, 1.1, 0.5 and 0.3 microns. The fractions were collected by placing filters in the apparatus and determining the amount of powder that impinged on them by gravimetric and/or analytical measurements. The fine particle fraction of the total dose of powder (FPF_TD) less than or equal to an effective cut-off aerodynamic diameter was calculated by dividing the powder mass recovered from the desired stages of the impactor by the total particle mass in the capsule. Results are reported as the fine particle fraction of less than 4.4 microns (FPF_TD<4.4 microns), as well as mass median aerodynamic diameter (MMAD) and GSD calculated from the FPF trend across stages. Another standard way of determining the fine particle fraction (FPF) is to calculate the FPF relative to the recovered or emitted dose of powder by dividing the powder mass recovered from the desired stages of the impactor by the total powder mass recovered from the impactor.

If desired, a two-stage collapsed ACI can also be used to measure fine particle fraction. The two-stage collapsed ACI consists of only stages 0 and 2, and the collection filter, all from the eight-stage ACI, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on a collection filter (stage F) is thus composed of respirable dry particles having an aerodynamic diameter of less than 3.4 microns. The airflow at such a calibration is approximately 60 L/min.

Tap Density. Tap density was measured one of two ways, as is specified in a specific example. For Tap Density Method #1, a SOTAX Tap Density Tester model TD1 (Horsham, Pa.) was used in order to follow USP29<616>. For any given run, the entire sample was introduced into a tared 100-mL graduated cylinder using a stainless steel funnel. The powder mass and initial volume ($V_0$) were recorded, and the cylinder was attached to the anvil and run according to the USP Method I. See Table 3 below.

TABLE 3

| USP Method I tapped density parameters | |
| --- | --- |
| Drop height | 14 ± 2 mm |
| Nominal Rate | 300 strokes/min |
| Tap count 1 | 500 |
| Tap count 2 | 750 |
| Tap count 3 | 1250 |

For the first pass, the cylinder was tapped using Tap Count 1 and the resulting volume $V_a$ was recorded. For the second pass, Tap Count 2 was used resulting in the new volume $V_{b1}$. If $V_{b1}$>98% of $V_a$, the test was complete, otherwise Tap Count 3 was used iteratively until $V_{bn}$>98% of $V_{bn-1}$.

Calculations were made to determine the powder bulk density ($d_B$), tap density ($d_T$), Hausner Ratio (H) and Carr index (C).

For Tap Density Method #2, a modified USP method requiring smaller powder quantities by following USP29<616> with the substitution of a 1.5 cc microcentrifuge tube (Eppendorf AG, Hamburg, Germany) or a 0.3 cc section of a disposable serological polystyrene micropipette (Grenier Bio-One, Monroe, N.C.) with polyethylene caps (Kimble Chase, Vineland, N.J.) to cap both ends and hold the powder within the pipette section. The sample was introduced into the micropipette section through a funnel made with weighing paper (VWR International, West Chester, Pa.) and the pipette section was plugged with polyethylene caps (Kimble Chase, Vineland, N.J.) to hold the powder. This modified method was required when less powder was available to perform the desired testing.

Instruments for measuring tap density, known to those skilled in the art, include but are not limited to the Dual Platform Microprocessor Controlled Tap Density Tester (Vankel, Cary, N.C.) or the SOTAX Tap Density Tester model TD1 mentioned above or model TD2. Tap density is a standard measure of the envelope mass density. The envelope mass density of an isotropic particle is defined as the mass of the particle divided by the minimum spherical envelope volume within which it can be enclosed.

Bulk Density. Bulk density was estimated prior to tap density measurement by dividing the weight of the powder by the volume of the powder, as estimated using the volumetric measuring device.

Emitted Geometric or Volume Diameter. The volume median diameter (VMD) (Dv50) of the powder after it emitted from a dry powder inhaler, which may also be referred to as volume median geometric diameter (VMGD) and ×50, was determined using a laser diffraction technique via the Spraytec diffractometer (Malvern, Inc., Westborough, Mass.). Powder was filled into size 3 capsules (V-Caps, Capsugel) and placed in a capsule based dry powder inhaler (RS01 Model 7 High resistance, Plastiape, Italy), or DPI, which was sealed in a container by an airtight fitting. The steady airflow exited through the DPI typically at 60 L/min for a set duration, typically of 2 seconds controlled by a timer controlled solenoid and then passed through the laser beam of the Spraytec as an external flow. Alternatively in a closed bench configuration, the DPI was joined via an airtight connection to the inhaler adapter of the Spraytec and a steady airflow rate was drawn through the DPI typically at 60 L/min for a set duration, typically of 2 seconds controlled by a timer controlled solenoid (TPK2000, Copley, Scientific, UK). The outlet aerosol then passed perpendicularly through the laser beam as an internal flow. The resulting geometric particle size distribution of the aerosol was calculated from the software based on the measured scatter pattern on the photodetectors with samples typically taken at 1000 Hz for the duration of the inhalation. The Dv50, GSD, and FPF<5.0 µm measured were then averaged over the duration of the inhalation.

Fine Particle Dose. The fine particle dose is determined using the information obtained by the ACI. The cumulative mass deposited on the filter, and stages 6, 5, 4, 3, and 2 for a single dose of powder actuated into the ACI is equal to the fine particle dose less than 4.4 microns (FPD<4.4 µm).

Capsule Emitted Powder Mass. A measure of the emission properties of the powders was determined by using the information obtained from the ACI tests or emitted geometric diameter by Spraytec. The filled capsule weight was recorded at the beginning of the run and the final capsule weight was recorded after the completion of the run. The difference in weight represented the amount of powder emitted from the capsule (CEPM or capsule emitted powder mass). The CEPM was reported as a mass of powder or as a percent by dividing the amount of powder emitted from the capsule by the total initial particle mass in the capsule.

Units. Certain units, which are equivalent, are used interchangeably throughout the examples, e.g., micrometers and microns.

Example 1. Production and Characterization of a Representative Dry Powder

Formulation I comprised of sodium chloride, leucine, fluticasone propionate (FP), and salmeterol xinafoate (SX). The composition of Formulation I was 65.42% (w/w) sodium chloride, 30.0% (w/w) leucine, 4.0% FP, and 0.58% SX. Formulation I was produced by spray drying. A solution of the components was made, and then pumped to a spray dryer, which generated homogenous particles.

The materials used to make the above powder and their sources are as follows. Sodium chloride, L-leucine, fluticasone propionate (FP), and salmeterol xinafoate (SX) were obtained from Spectrum Chemicals (Gardena, Calif.) or USP Pharmacopeia (Rockville, Md.). Ultrapure water was from a water purification system (Millipore Corp., Billerica, Mass.). Ethyl alcohol (200 Proof, ACS/USP Grade) was from Pharmco-Aaper (Shelbyville, Ky.).

Spray drying homogenous particles requires that the ingredients of interest be solubilized in solution or suspended in a uniform and stable suspension. Sodium chloride and leucine are sufficiently water-soluble to prepare suitable spray drying solutions. However, fluticasone propionate (FP) and salmeterol xinafoate (SX) are practically insoluble in water. As a result of these low solubilities, formulation feedstock development work was necessary to prepare solutions or suspensions that could be spray dried. FP and SX are slightly soluble in ethanol, so these were fully solubilized in 99% ethanol prior to mixing with other components dissolved in water to obtain a 10 g/L solids concentration in 60% ethanol solution, with the remainder of the liquid being water. The solution was kept agitated throughout the process until the materials were completely dissolved in the water or ethanol solvent system at room temperature.

Formulation I contained a total solids amount of 30 grams (g), total volume was 3 liters, total solids concentration was 10 grams per liter. The amount of NaCl, leucine, FP, SX, water, and ethanol in one liter was 9.00 g, 19.62 g, 1.20 g and 0.18 g, respectively.

Formulation I was prepared by spray drying on a Büchi B-290 Mini Spray Dryer (BÜCHI Labortechnik AG, Flawil, Switzerland) with powder collection in a 60 mL glass vessel from a High Performance cyclone. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm (667 LPH) and the aspirator rate to 80% (32 m3/hr). Room air was used as the drying gas. Inlet temperature of the process gas was 100° C. and outlet temperature from 39° C. to 43° C. with a liquid feedstock flow rate of 10.2 mL/min.

The spray drying process yield was obtained by calculating the ratio of the weight of dry powder collected after the spray drying process was completed divided by the weight of the starting solid components placed into the spray drying liquid feed. The spray drying process yield for Formulation I was 69.2%. The powder produced was further characterized with regard to density and VMGD. Tapped density was determined using Tap Density Method #2. A SOTAX Tap Density Tester model TD1 was used. For any given run, a sample was introduced to a tared 0.3 cc section of a Grenier disposable serological polystyrene micropipette using a funnel made with weighing paper (VWR International, West Chester, Pa.) and the pipette section was plugged with polyethylene caps (Kimble Chase, Vineland, N.J.) to hold the powder.

The powder mass and initial volume (V0) were recorded and the pipette was attached to the anvil and run according to the USP I method. For the first pass, the pipette was tapped using Tap Count 1 (500 taps) and the resulting volume Va was recorded. For the second pass, Tap Count 2 was used (750 taps) resulting in the new volume Vb1. If Vb1>98% of Va, the test was complete, otherwise Tap Count 3 was used (1250 taps) iteratively until Vbn>98% of Vbn−1. Bulk density was estimated prior to tap density measurement by dividing the weight of the powder by the volume of the powder, as estimated using the volumetric measuring device. Calculations were made to determine the powder bulk density (dB), tap density (dT), and Hausner Ratio (H), which is the tap density divided by the bulk density.

Volume median diameter was determined using a HELOS laser diffractometer and a RODOS dry powder disperser. A microspatula of material (approximately 5 milligrams) was introduced into the RODOS funnel, where a shear force is applied to a sample of particles as controlled by the regulator pressure of the incoming compressed dry air. The pressure setting was set to a 1.0 bar dispersion energy. The dispersed particles traveled through a laser beam where the resulting diffracted light pattern produced is collected, using an R1 or R3 lens, by a series of detectors. The ensemble diffraction pattern is then translated into a volume-based particle size distribution using the Fraunhofer diffraction model, on the basis that smaller particles diffract light at larger angles.

The resulting value for tap density was 0.44 g/cc, bulk density was 0.22 g/cc, Hausner Ratios was 2.03, and VMGD using the HELOS/RODOS on the bulk powder at 1 bar was 1.69 microns with a geometric standard deviation of 2.0. The water content using a Karl Fischer test was about 0.3%, which was below the limit of quantification. The powder appeared to be free flowing both as bulk powder and after being filled into capsules. The chemical content of the Therapeutic agents, FP and SX, was also assessed, and is reported in Table 4. As can be seen from the data, the content of FP and SX in both the bulk powder and in the filled capsules was close to or matched the theoretical loading of 4.0% and 0.58%, respectively.

TABLE 4

Initial chemical content data for the FP and SX using HPLC.

|  | FP Content in the Dry Powder (%) | SX Content in the Dry Powder (%) |
| --- | --- | --- |
| Bulk | 3.96 | 0.58 |
| Capsules | 3.97 | 0.58 |

A dynamic vapor sorption (DVS) ramp mode experiment was conducted to evaluate the hygroscopicity and water uptake potential of Formulation I, which was exposed to 20%-80% relative humidity (RH). In this experiment, the RH was initially held constant at 20% for 0.5 hour and was increased from 20% to 80% continuously over the course of two hours and then it was decreased continuously from 80% to 20% over two hour duration. This low and high humidity ramping was conducted twice in the same experiment. The dm (%) refers to the change in mass of the sample with 100% being the original sample mass, also called the reference mass. The peak in the dm (%), see FIG. 1, occurred shortly after the DVS reached the maximum RH of 80%. The total value at the peak was 101.8%, with an absorbed value of 1.8% in mass of water. This water desorbed completely when the RH was ramped back down toward 20%. The final mass of Formulation I was 0.14% lower than the initial mass. The data is also presented in Table 5 below.

TABLE 5

Change in mass of a sample of Formulation I at varying RH (%) using a DVS.

| Target % RH | RH (%) | Dm (%) (Weight variation with based level as 100%) | Elapsed Time (min) | Weight (mg) |
| --- | --- | --- | --- | --- |
| 20 | 20.46 | 99.992 | 33 | 12.9037 |
| 30 | 30.22 | 99.981 | 54 | 12.9022 |
| 40 | 40.37 | 100.102 | 75 | 12.9179 |
| 50 | 50.42 | 100.151 | 96 | 12.9241 |
| 60 | 60.05 | 100.131 | 116 | 12.9216 |
| 70 | 70.04 | 100.28 | 136 | 12.9408 |
| 80 | 76.98 | 101.182 | 151 | 13.0573 |
| 70 | 70.13 | 101.434 | 166 | 13.0898 |
| 60 | 60.14 | 100.375 | 186 | 12.9531 |
| 50 | 50.45 | 100.214 | 206 | 12.9324 |
| 40 | 40.30 | 100.093 | 228 | 12.9167 |
| 30 | 30.11 | 99.899 | 249 | 12.8916 |
| 20 | 20.19 | 99.876 | 269 | 12.8887 |
| 30 | 30.13 | 99.91 | 323 | 12.8930 |
| 40 | 40.23 | 99.941 | 344 | 12.8971 |
| 50 | 50.33 | 99.978 | 366 | 12.9019 |
| 60 | 60.00 | 100.021 | 386 | 12.9075 |
| 70 | 70.50 | 100.158 | 407 | 12.925 |
| 80 | 77.02 | 100.891 | 420 | 13.0197 |
| 70 | 70.35 | 101.071 | 436 | 13.0429 |
| 60 | 60.33 | 100.147 | 456 | 12.9237 |
| 50 | 50.14 | 100.04 | 477 | 12.9098 |
| 40 | 40.00 | 99.956 | 498 | 12.8990 |
| 30 | 30.31 | 99.897 | 519 | 12.8914 |
| 20 | 20.43 | 99.866 | 539 | 12.8875 |

Note:
The sample temperature was 25.0° C. throughout the study.

Example 2. Long-Term Stability of a Representative Dry Powder

In this example are presented stability data for a three-month stability study performed using Formulation I. The data presented in Example 1 represents the time zero characteristics of the Dry Powder used in this stability study. The three testing conditions used were: (i) long-term, (ii) accelerated, and (iii) refrigerated. For the long-term condition, the powder was stored at 25° C. and 60% RH; for the accelerated condition, the powder was stored at 40° C. and 75% RH; and for refrigerated, the powder was stored at 5° C. The properties that were monitored were (i) powder appearance, (ii) stability of the Therapeutic agents, (iii) stability of the VMGD of the Dry Powder.

The powder appearance over the three months of the stability study was assessed. The test was a pass or fail test where the powder was assessed to see if it was white or off-white in color and that there were no visible particulate matter in the powder. Formulation I passed all powder appearance tests at all conditions for all time points, namely, 0, 0.5, 1.0, and 3.0 months.

FP and SX content were close to the theoretical content of 4.0% and 0.58% at time point 0. The goal for the study was for the content to stay with the 80% to 120% of the time point 0 baseline values. This goal was achieved. See Tables 6 and 7. Notably, the FP content appears to decrease at the 1 month time point, however recovers to near time zero values at the 3 month time point. The values for SX were relatively stable through the 1 month time point, and appear to have decreased by about 10% in the 3 month time point.

TABLE 6

Drug Content of Fluticasone Propionate (FP) in Formulation I using HPLC

| Time Point (months) | FP (%) at (5° C.) storage | FP (%) at (25° C./60% RH) storage | FP (%) at (40° C./75% RH) storage |
|---|---|---|---|
| 0 | 3.97 ± 0.02 | 3.97 ± 0.02 | 3.97 ± 0.02 |
| 0.5 | 3.94 ± 0.11 | 3.95 ± 0.02 | 3.95 ± 0.01 |
| 1.0 | 3.79 ± 0.01 | 3.76 ± 0.05 | 3.89 ± 0.01 |
| 3.0 | 3.91 ± 0.04 | 3.91 ± 0.02 | 3.92 ± 0.01 |

All data points for FP fell within the 80%-120% interval of the baseline value, i.e. 3.97 +/-0.79%.

TABLE 7

Drug Content of Salmeterol Xinafoate (SX) in Formulation I using HPLC

| Time Point (months) | SX (%) at (5° C.) storage | SX (%) at (25° C./60% RH) storage | SX (%) at (40° C./75% RH) storage |
|---|---|---|---|
| 0 | 0.58 ± 0.00 | 0.58 ± 0.00 | 0.58 ± 0.00 |
| 0.5 | 0.59 ± 0.00 | 0.61 ± 0.00 | 0.59 ± 0.00 |
| 1.0 | 0.56 ± 0.00 | 0.57 ± 0.01 | 0.56 ± 0.00 |
| 3.0 | 0.52 ± 0.00 | 0.54 ± 0.03 | 0.52 ± 0.00 |

All data points for SX fell within the 80%-20% interval of the baseline value, i.e. 0.58 +/- 0.12%.

The time point zero (0) baseline VMGD for Formulation I, post-capsule filling, was 1.92 microns. The VMGD dropped at time point 0.5 months by about 10%, but then increased through the rest of the study, as is shown in Table 8. At the accelerated storage condition at time point 3 months, the VMGD is up by about 10% from the baseline value, but still within the 80% to 120% window of the baseline VMGD. Overall, the fluctuation in the VMGD with storage for 3 months at different conditions is minimal.

TABLE 8

VMGD and standard deviation (Stdev) by HELOS/RODOS at 1.0 bar for Form. I

| Time Point (months) | VMGD and Stdev (both in microns) at (5° C.) storage | VMGD and Stdev (both in microns) at (25° C./60% RH) storage | VMGD and Stdev (both in microns) at (40° C./75% RH) storage |
|---|---|---|---|
| 0 | 1.92 ± 0.19 | 1.92 ± 0.19 | 1.92 ± 0.19 |
| 0.5 | 1.70 ± 0.01 | 1.60 ± 0.09 | 1.85 ± 0.05 |
| 1.0 | 1.70 ± 0.01 | 1.80 ± 0.04 | 1.91 ± 0.05 |
| 3.0 | 1.80 ± 0.07 | 1.91 ± 0.05 | 2.15 ± 0.05 |

All VMGD data points fell within the 80%-120% interval of the baseline value, i.e. 1.92 +/- 0.38 micrometers The time point zero (0) baseline MMAAD for Formulation I, post-capsule filling, was 3.49 for FP and 3.40 for SX. The MMAD dropped at time point 0.5 months by about 10%, but then increased through the rest of the study at the to return to baseline values for the 5° C. condition, as is shown in Tables 9+10. At the 25° C./60% RH condition, both the FP and SX gradually increased in MMAD by a total of about 5%. At the accelerated storage condition, there was initial increase in MMAD at the 0.5 month time point, but then the values returned to baseline at the 3 months timepoint. The FPD values for the standard and refrigerated conditions saw a rise at the 0.5 month timepoint, but then returned toward baseline at by the 3 month timepoint. The FPF values for the refrigerated conditions started somewhat high at the 0.5 month timepoint, but returned to near baseline values by the 3 month timepoint. The FPF values stay consistent for the standard stability conditions.

TABLE 9

MMAD with GSD, FPD, and FPF of emitted dose for FP of Formulation I Fluticasone Propionate

| Parameter | Storage Condition | Stability Time Point (Months) | | | |
|---|---|---|---|---|---|
| | | 0 | 0.5 | 1 | 3 |
| MMAD (micrometers) | 25° C./60% RH | 3.49 | 3.59 | 3.63 | 3.71 |
| | 40° C./75% RH | | 3.68 | 3.57 | 3.45 |
| | 5° C. | | 3.23 | 3.36 | 3.48 |
| GSD | 25° C./60% RH | 1.72 | 1.66 | 1.64 | 1.65 |
| | 40° C./75% RH | | 1.64 | 1.65 | 1.69 |
| | 5° C. | | 1.66 | 1.67 | 1.7 |
| FPD (mg) | 25° C./60% RH | 1.22 | 1.3 | 1.19 | 1.28 |
| | 40° C./75% RH | | 1.27 | 1.23 | 1.38 |
| | 5° C. | | 1.46 | 1.32 | 1.34 |
| FPF (as % of emitted dose) | 25° C./60% RH | 53.4 | 57.2 | 56.7 | 54.2 |
| | 40° C./75% RH | | 56.5 | 59.9 | 59.5 |
| | 5° C. | | 63.1 | 60.4 | 57.3 |

TABLE 10

MMAD with GSD, FPD, and FPF of emitted dose for SX of Formulation I Salmeterol Xinafoate

| Parameter | Storage Condition | Stability Time Point (Months) | | | |
|---|---|---|---|---|---|
| | | 0 | 0.5 | 1 | 3 |
| MMAD (micrometers) | 25° C./60% RH | 3.4 | 3.47 | 3.55 | 3.59 |
| | 40° C./75% RH | | 3.56 | 3.42 | 3.32 |
| | 5° C. | | 3.15 | 3.3 | 3.39 |
| GSD | 25° C./60% RH | 1.74 | 1.88 | 1.64 | 1.66 |
| | 40° C./75% RH | | 1.64 | 1.66 | 1.71 |
| | 5° C. | | 1.65 | 1.67 | 1.73 |
| FPD (mg) | 25° C./60% RH | 0.186 | 0.211 | 0.182 | 0.194 |
| | 40° C./75% RH | | 0.192 | 0.184 | 0.189 |
| | 5° C. | | 0.214 | 0.203 | 0.206 |
| FPF (as % of emitted dose) | 25° C./60% RH | 58.7 | 60.5 | 61 | 57.6 |
| | 40° C./75% RH | | 60.2 | 63.8 | 63.5 |
| | 5° C. | | 65.1 | 65 | 60 |

Example 3. Dry Powder Flow Properties

A. Flow Properties of Formulation II, III, IV, and V

The flowability of Formulations II, III, IV and V were assessed using conventional methods in the art for the characterization of powder flowability. See formulations listed in Table 11. Formulations II through V can be found in WO2010/111680 and are hereby incorporated by reference. Formulation VI can be found in PCT/US2011/49333 and is hereby incorporated by reference.

TABLE 11

Formulations tested for their flow properties

| Formulation # in current document | Formulation # in WO2010/111680 | Composition |
|---|---|---|
| Formulation II | Formulation I | 10.0% leucine, 35.1% calcium chloride, 54.9% sodium citrate |
| Formulation III | Formulation II | 10.0% leucine, 39.6% calcium chloride, 50.4% sodium sulfate |
| Formulation IV | Formulation III | 10.0% leucine, 58.6% calcium lactate, 31.4% sodium chloride |
| Formulation V | Formulation XIV | 10.0% maltodextrin, 58.6% calcium lactate, 31.4% sodium chloride |

The Flowability Index for each powder was determined using a Flodex Powder Flowability Test Instrument (Hanson Research Corp., model 21-101-000, Chadsworth, Calif.). For any given run, the entire sample was loaded using a stainless steel funnel aimed at the center of the trap door hole in the cylinder. Care was taken not to disturb the column of powder in the cylinder. After waiting ~30 sec for the potential formation of flocculi, the trap door was released while causing as little vibration to the apparatus as possible. The test was considered a pass if the powder dropped through the trap door so that the hole was visible looking down through the cylinder from the top and the residue in the cylinder formed an inverted cone; if the hole was not visible or the powder fell straight through the hole without leaving a cone-shaped residue, the test failed. Enough flow discs were tested to find the minimum size hole the powder would pass through, yielding a positive test. The minimum-sized flow disc was tested two additional times to obtain 3 positive tests out of 3 attempts. The flowability index (FI) is reported as this minimum-sized hole diameter.

Bulk and tap densities were determined using a SOTAX Tap Density Tester model TD2. For any given run, the entire sample was introduced to a tared 100-mL graduated cylinder using a stainless steel funnel. The powder mass and initial volume (V0) were recorded and the cylinder was attached to the anvil and run according to the USP I method. For the first pass, the cylinder was tapped using Tap Count 1 (500 taps) and the resulting volume Va was recorded. For the second pass, Tap Count 2 was used (750 taps) resulting in the new volume Vb1. If Vb1>98% of Va, the test was complete, otherwise Tap Count 3 was used (1250 taps) iteratively until Vbn>98% of Vbn−1. Calculations were made to determine the powder bulk density (dB), tap density (dT), Hausner Ratio (H) and Compressibility Index (C), the latter two of which are standard measures of powder flowability. "H" is the tap density divided by the bulk density, and "C" is 100*(1-(bulk density divided by the tap density)). Skeletal Density measurement was performed by Micromeritics Analytical Services using an Accupyc II 1340 (Micromeritics, Narcross, N.C.) which used a helium gas displacement technique to determine the volume of the powders. The instrument measured the volume of each sample excluding interstitial voids in bulk powders and any open porosity in the individual particles to which the gas had access. Internal (closed) porosity was still included in the volume. The density was calculated using this measured volume and the sample weight which was determined using a balance. For each sample, the volume was measured 10 times and the skeletal density (dS) was reported as the average of the 10 density calculations with standard deviation.

Results for these density and flowability tests are shown in Tables 12 and 13. All four of the powders tested possess Hausner Ratios and Compressibility Indices that are described in the art as being characteristic of powders with extremely poor flow properties (See, e.g., USP <1174>). It is thus surprising that these powders, in practice, possess good processability, for example, when filling capsules, as described herein.

TABLE 12

Bulk and tap densities and flow properties of Formulations II-V powders.

| Sample | FI (mm) | $d_B$ (g/mL) | $d_T$ (g/mL) | H | C |
|---|---|---|---|---|---|
| Formulation II | 26 | 0.193 | 0.341 | 1.77 | 43.4% |
| Formulation III | 22 | 0.313 | 0.722 | 2.31 | 56.7% |
| Formulation IV | 18 | 0.177 | 0.388 | 2.19 | 54.3% |
| Formulation V | >34 | 0.429 | 0.751 | 1.75 | 42.9% |

TABLE 13

Skeletal density measurements of powders Formulations II-V

| Sample | $d_{S1} \pm \sigma$ (g/mL) | $d_{S2} \pm \sigma$ (g/mL) |
|---|---|---|
| Formulation II | 1.7321 ± 0.0014 | 1.7384 ± 0.0042 |
| Formulation III | 1.6061 ± 0.0007 | 1.6074 ± 0.0004 |
| Formulation IV | 2.1243 ± 0.0011 | 2.1244 ± 0.0018 |
| Formulation V | 1.6759 ± 0.0005 | 1.6757 ± 0.0005 |

USP <1174> mentioned previously notes that dry powders with a Hausner Ratio greater than 1.35 are poor flowing powders. It is therefore unexpected that powders with Hausner Ratios of 1.75 to 2.31 would possess good processability, for example, when filling capsules, as described herein. B. Flow Properties of Formulation VI Formulation VI was tested for its flowability. See Table 14 for the formulation tested.

TABLE 14

Formulation tested for its flow property

| Formulation # in current document | Formulation # in PCT/US2011/49333 | Composition |
|---|---|---|
| Formulation VI | Formulation I | 20.0% leucine, 75.0% calcium lactate, 5.0% sodium chloride |

An experimentally derived assessment for a powder's flow properties called the static angle of repose or "Angle of Repose" was used to assess Formulation VI's flowability. The angle of repose is also denoted the angle of slip and is a relative measure of the friction between the particles as well as a measure of the cohesiveness of the particles. It is the constant, three-dimensional angle (relative to the horizontal base) assumed by a cone-like pile of material formed by any of several different methods. See USP29<1174> for a further description of this method.

The Angle of Repose for Formulations VI was 34.7° with a standard deviation of 3.5°. As per USP29<1174>, a cohesive powder has an angle of repose of at least 400, e.g., in the range of 40° to 500. A freely flowing powder tends to possess an Angle of Repose of 30°, or less, although an Angle of Repose between 30° and 40° should lead to a powder which can be processed further without much difficultly. Based on these ranges, Formulation VI can be characterized as a powder which can be processed without much difficulty.

Example 4. Xcelodose Filling Data

Formulation VI was filled into size 3 HPMC capsules (Capsugel, Greenwood, S.C.) using an Xcelodose 600S (Capsugel, Greenwood, S.C.) automated capsule filler, and demonstrated good powder flow characteristics as measured by both (i) the achievable time to fill a capsule and (ii) the rate of capsules filled. Capsules were filled in separate runs to 10 mg, 20 mg and 40 mg target fill weights at room temperature and under a controlled humidity (30%±5% RH). Additionally, a 10 mg fill weight was filled at room temperature and under a reduced humidity (15%±5% RH) with a 100% inspection of all capsule fill weights held to ±5%. The Xcelodose works to fill capsules by using a solenoid controlled tapper arm to cause bulk powder in the hopper to fall through apertures in a dispensing head at the bottom of the hopper, much like an inverted pepper shaker. A microbalance is used as a feedback system to measure and control the fill weight of each capsule. A pre-determined 2 speed tapping procedure is used to quickly fill the capsule at a high frequency to near its target fill weight and then at a lower frequency to more accurately fill to the target. For the 4 runs shown in Table 15, the Xcelodose filling parameters are given for the high and low tapping frequencies, mass targeted for slow tapping, and dispensing head used. All runs achieved their target fill weight. For each of the four runs, the flow of Formulation VI into the capsules allowed for a mean run fill rate of over 190 capsules per hour, with the maximum mean run fill rate of 253 capsules observed for Run B. In addition, the average time to fill the capsules ranged from 10.0 seconds to fill the 10 mg capsules to 14.0 seconds to fill the 40 mg capsules, with the applied tapping procedures listed.

TABLE 15

Formulation VI was filled into capsules at varying fill weights and conditions listed.

| | | Run | | | |
|---|---|---|---|---|---|
| | | A | B | C | D |
| Number of capsules filled for each Run | | 251 | 318 | 289 | 301 |
| Relative Humidity (%) | | 15 | 30 | 30 | 30 |
| Run Results | | | | | |
| Fill weight (mg) | Target | 10 | 10 | 20 | 40 |
| | Average | 10.029 | 10.054 | 20.155 | 40.422 |
| | St Dev | 0.174 | 0.179 | 0.383 | 0.618 |
| Time to fill Capsule (s) | Average | 11.7 | 10.0 | 10.4 | 14.0 |
| | St Dev | 3.5 | 4.6 | 4.5 | 6.6 |
| Yield | (%) | 95.26 | 80.15 | 83.25 | 77.24 |
| Rate of capsule filling | (#/hour) | 191 | 253 | 207 | 228 |
| Xcelodose Parameters | | | | | |
| High Frequency | (Hz) | 24 | 24 | 27 | 36 |
| Low Frequency | (Hz) | 5 | 5 | 5 | 5 |
| Mass for slow tapping | (mg) | 1.4 | 1.4 | 2.1 | 1.8 |
| Dispense Head | | PQ | RK | RK | RK |
| Dispensing Holes (#) | | 43 | 19 | 19 | 19 |
| Hole Diameter (mm) | | 1 | 1.5 | 1.5 | 1.5 |

Example 5. Xcelodose Filling Data for a Moderately to Large Scale Filling Run Formulation VI was filled into size 3 HPMC capsules (Capsugel, Greenwood, S.C.) using an Xcelodose 600S (Capsugel, Greenwood, S.C.) automated capsule filler and demonstrated good powder flow characteristics as measured by both the rate of capsules filled and the yield of the batch. Capsules were filled to 10 mg in one clinical scale batch at room temperature and a controlled humidity of 30±5%. All capsule fill weights were measured and held to a range of 9.5 to 10.5 mg or 5% tolerance. The Xcelodose fills capsules by using a solenoid controlled tapper arm to cause bulk powder in the hopper to fall through apertures in a dispensing head at the bottom of the hopper, much like an inverted pepper shaker. A microbalance is used as a feedback system to measure and control the fill weight of each capsule. A pre-determined, 2-speed tapping procedure is used to quickly fill the capsule at a high frequency to near its target fill weight and then at a lower frequency to more accurately approach the target. The Xcelodose filling parameters used for production of this batch are given in Table 16. The batch achieved its target 10 mg fill weight with Formulation VI flowing from the hopper into the capsules sufficiently smoothly to achieve an average batch fill rate of 413 capsules per hour from the Xcelodose 600S over a batch size of 6794 acceptable capsules. In addition, the yield from the filling portion of the batch manufacture was 81.3% acceptable capsules.

TABLE 16

Formulation VI was filled into capsules using an Xcelodose 600S Capsule Filler

| | | Formulation VI |
|---|---|---|
| Batch | | A |
| Batch size | (number of capsules) | 6794 |
| Yield of acceptable capsule | (% acceptable/total) | 81.30% |
| Rate of capsule filling per hour | (number/hour) | 413 |
| Xcelodose Filling Parameters | | |
| High Frequency | (Hz) | 24 |
| Low Frequency | (Hz) | 6 |
| Mass for slow tapping | (mg) | 1.6 |
| Dispense Head | (name) | PQ |
| Dispensing Holes | (number of holes) | 43 |
| Hole Diameter | (millimeters) | 1 |

Example 6. High Drug Load, Dry Powder Metal Cation Salt-Based Formulations

A. Powder Preparation.

Feedstock solutions were prepared in order to manufacture dry powders comprised of dry particles containing a metal cation salt, optionally a non-salt excipient, and at least one therapeutic agent, the latter being in relatively high loading in the solution compared to the other components. Table 17 lists the components of the feedstock formulations used in preparation of the dry powders comprised of dry particles. Weight percentages are given on a dry basis.

TABLE 17

| Feedstock compositions of sodium-salt with other therapeutic agents | | | | | | |
|---|---|---|---|---|---|---|
| Formulation | Salt | % Salt load (w/w) | Excipient | % Excipient load (w/w) | Drug | % Drug load (w/w) |
| VII | Sodium sulfate | 6.3 | Leucine | 11.7 | Levofloxacin | 82.0 |
| VIII | Magnesium Lactate | 6.3 | Leucine | 11.7 | Levofloxacin | 82.0 |
| IX | Sodium chloride | 6.3 | Leucine | 11.7 | Levofloxacin | 82.0 |
| X | Sodium chloride | 34.0 | Leucine | 16.0 | Levofloxacin | 50.0 |

The feedstock solutions were made according to the parameters in Table 18.

TABLE 18

| Formulation Conditions | | | | |
|---|---|---|---|---|
| | Formulation: | | | |
| | VII | VIII | IX | X |
| Total solids (g) | 3 | 3 | 3 | 5 |
| Total volume water (L) | 0.3 | 0.3 | 0.3 | 0.5 |
| Total solids concentration (g/L) | 10 | 10 | 10 | 10 |
| Amount of NaCl in 1 L (g) | 0 | 0 | 0.63 | 3.4 |
| Amount of NaSulf in 1 L (g) | 0.63 | 0 | 0 | 0 |
| Amount of MgLact in 1 L (g) | 0 | 0.63 | 0 | 0 |
| Amount leucine in 1 L (g) | 1.17 | 1.17 | 1.17 | 1.6 |
| Amount Levofloxacin in 1 L (g) | 8.2 | 8.2 | 8.2 | 5.0 |

Note:
For all formulations, the liquid feedstock was batch mixed.

Formulation VII through X dry powders were produced by spray drying on the Büchi B-290 Mini Spray Dryer (BÜCHI Labortechnik AG, Flawil, Switzerland) with powder collection from a High Performance cyclone in a 60 mL glass vessel. The system used the Büchi B-296 dehumidifier and only for Formulation X an external LG dehumidifier (model 49007903, LG Electronics, Englewood Cliffs, N.J.) was run constantly given humidity was around 30% in the spray drying room. Atomization of the liquid feed utilized a Büchi two-fluid nozzle with a 1.5 mm diameter. The two-fluid atomizing gas was set at 40 mm (667 LPH). The aspirator rate was set to 90% (35 m3/h) for Formulations VII, VIII and X; to 100% (38 m3/h) for Formulation IX. Air was used as the drying gas and the atomization gas. Table 19 below includes details about the spray drying conditions.

TABLE 19

| Spray Drying Process Conditions | | | | |
|---|---|---|---|---|
| | Formulation | | | |
| Process Parameters | VII | VIII | IX | X |
| Liquid feedstock solids concentration (g/L) | 10 | 10 | 10 | 10 |
| Process gas inlet temperature (° C.) | 180 | 180 | 100 | 180 |
| Process gas outlet temperature (° C.) | 88 | 91 | 59 | 90-93 |
| Process gas flow rate (liter/hr, LPH) | 667 | 667 | 667 | 667 |
| Atomization gas flow rate (meters$^3$/hr) | 35 | 35 | 38 | 35 |
| Liquid feedstock flow rate (mL/min) | 5.8 | 5.8 | 2.8 | 5.6 |

B. Powder Characterization.

Powder physical and aerosol properties are summarized in Tables 20 to 24 below. Values with ± indicate standard deviation of the value reported. Two-stage ACI-2 results are reported in Table 21 for FPFTD<3.4 μm and FPFTD<5.6 μm.

TABLE 20

| Aerodynamic properties | | |
|---|---|---|
| | ACI-2 | |
| Formulation | FPFTD < 3.4 μm % | FPFTD < 5.6 μm % |
| VII | 20.25% ± 5.26% | 48.83% ± 6.32% |
| VIII | 20.40% ± 0.79% | 47.43% ± 0.72% |
| IX | 32.91% ± 0.23% | 61.77% ± 0.82% |
| X | 31.80% ± 3.24% | 59.28% ± 4.41% |

All formulations had a tapped density greater than 0.6 g/cc. All formulations had a Hausner Ratio greater than 1.5.

TABLE 21

| Density properties | | | |
|---|---|---|---|
| | Density | | |
| Formulation | Bulk g/cc | Tapped g/cc | Hausner Ratio |
| VII | 0.44 ± 0.01 | 0.69 ± 0.01 | 1.59 |
| VIII | 0.41 ± 0.03 | 0.65 ± 0.02 | 1.59 |
| IX | 0.42 ± 0.01 | 0.82 ± 0.01 | 1.97 |
| X | 0.45 ± 0.03 | 0.93 ± 0.09 | 2.04 |

Table 22 shows that all formulations had geometric diameters (Dv50) of less than 3.7 microns when emitted from a dry powder inhaler at a flowrate of 60 LPM, and less or equal to 5.3 microns when emitted from a dry powder inhaler at a flowrate of 15 LPM.

TABLE 22

| Geometric Diameters | | | | |
|---|---|---|---|---|
| | Dispersibility - Spraytec | | | |
| | @ 60 LPM | | @ 15 LPM | |
| Formulation | Dv50 (μm) | GSD | Dv50 (μm) | GSD |
| VII | 3.32 ± 0.10 | 5.40 ± 0.39 | 5.30 ± 0.38 | 3.62 ± 0.12 |
| VIII | 3.64 ± 0.02 | 5.76 ± 0.32 | 4.59 ± 0.26 | 2.78 ± 0.08 |
| IX | 1.53 ± 0.12 | 6.07 ± 0.19 | 2.71 ± 0.07 | 2.57 ± 0.23 |
| X | 1.61 ± 0.12 | 5.65 ± 0.55 | 2.55 ± 0.04 | 3.25 ± 0.29 |

Table 23 shows that all formulations had a capsule emitted particle mass (CEPM) of greater than 98% at 60 LPM. All formulations had a CEPM of greater than 70% at 15 LPM.

TABLE 23

| Dispersibility properties | | |
|---|---|---|
| | Dispersibility-CEPM | |
| Formulation | @ 60 LPM CEPM | @ 15 LPM CEPM |
| VII | 98.76% ± 0.15% | 70.73% ± 21.45% |
| VIII | 98.59% ± 0.53% | 74.77% ± 21.23% |
| IX | 98.79% ± 0.58% | 87.79% ± 17.88% |
| X | 99.82% ± 0.05% | 98.25% ± 0.18% |

Table 24 shows that all measured formulations had a Dv50 of less than 2.1 microns when using the RODOS at a 1.0 bar setting. All measured formulations had a RODOS Ratio for 0.5 bar/4 bar of less than 1.3, and a RODOS Ratio for 1 bar/4 bar of less than 1.1.

TABLE 24

Dispersibility properties (Geometric diameter using RODOS)

| | RODOS | | | | | | | |
|---|---|---|---|---|---|---|---|---|
| Form. | 0.5 bar Dv50 (μm) | GSD | 1.0 bar Dv50 (μm) | GSD | 4.0 bar Dv50 (μm) | GSD | 0.5/4 bar | 1/4 bar |
| VII | 2.21 | 2.22 | 1.90 | 2.23 | 1.80 | 2.23 | 1.23 | 1.06 |
| VIII | 2.22 | 2.27 | 2.00 | 2.27 | 1.99 | 2.28 | 1.12 | 1.01 |
| IX | 1.82 | 2.23 | 1.64 | 2.29 | 1.65 | 2.24 | 1.10 | 0.99 |
| X | 1.95 | 2.11 | 2.04 | 2.05 | 2.06 | 2.04 | 0.95 | 0.99 |

Example 7. Dry Powder Metal Cation Salt-Based Formulations Delivered from a Multi-Unit Dose DPI (Diskus® Blister-Based DPI) Increased FPF Compared to Advair®

A spray dried formulation of fluticasone propionate and salmeterol xinafoate with weight percentages matching 500/50 strength Advair was produced (Formulation I) and dispersed from an Advair Diskus dry powder inhaler, obtained from commercial sources. The Diskus multi-unit dose dry powder inhaler was disassembled, the foil lidding of the blister strip was removed, and the remaining Advair 500/50 formulation was discarded. The blister strip was briefly rinsed with a 1:1 v/v mixture of acetonitrile and deionized water to remove any trace amounts of drug and allowed to dry. At controlled humidity conditions (RH=30±5%), a single blister well was filled with approximately 2 mg of Formulation I dry powder. The blister strip was re-inserted into the Diskus dry powder inhaler, ensuring that the filled well was aligned with the mouthpiece inlet. The Diskus dry powder inhaler was fully reassembled and the inhaler mouthpiece was inserted into a custom adapter for connection to the ACI induction port. A total of 4 wells were actuated into each ACI; the Advair Diskus dry powder inhaler was disassembled after each actuation to re-fill the blister well with Formulation I. Equivalent strength Advair powder (500/50 FP/SX, Formulation VII) was obtained from commercial sources and dispersed from the Advair Diskus dry powder inhaler (4 blisters per ACI) according to the manufacturer's instructions. ACI testing was performed at (n=3) at 90 LPM, including a pre-separator for all tests. Stages used for 90 LPM testes were IP, pre-separator, −1, −0, 1, 2, 3, 4, 5, and F with corresponding lower stage cutpoints of: >5.8, 5.8, 4.7, 3.3, 2.1, 1.1, 0.70, 0.40, and 0.0 μm. Stage −2 (lower stage cutpoint of 9.0 μm) was not available at the time of testing and was omitted from the impactor setup for both Formulations I and VII. Since only seven stages were used in the ACI setup, an additional Stage −0 from another impactor was placed after Stage F to be used as a spacer.

ACI8 testing was performed with a pre-separator for all runs. In brief, the method used inverted stage plates with glass microfiber filters as impaction surfaces. These filters were each rinsed with 10 mL of rinse solution consisting of 50% acetonitrile and 50% reagent water. The induction port was rinsed with 30 mL of rinse solution and the mouthpiece adapter rinsed with 10 mL of rinse solution. The pre-separator was filled with 10 mL of the rinse solution prior to the ACI8 run to prevent bounce and re-entrainment of large particles and then following the run, an additional 10 mL of rinse solution was added and the combined 20 mL used for rinsing the pre-separator.

Figure 2:
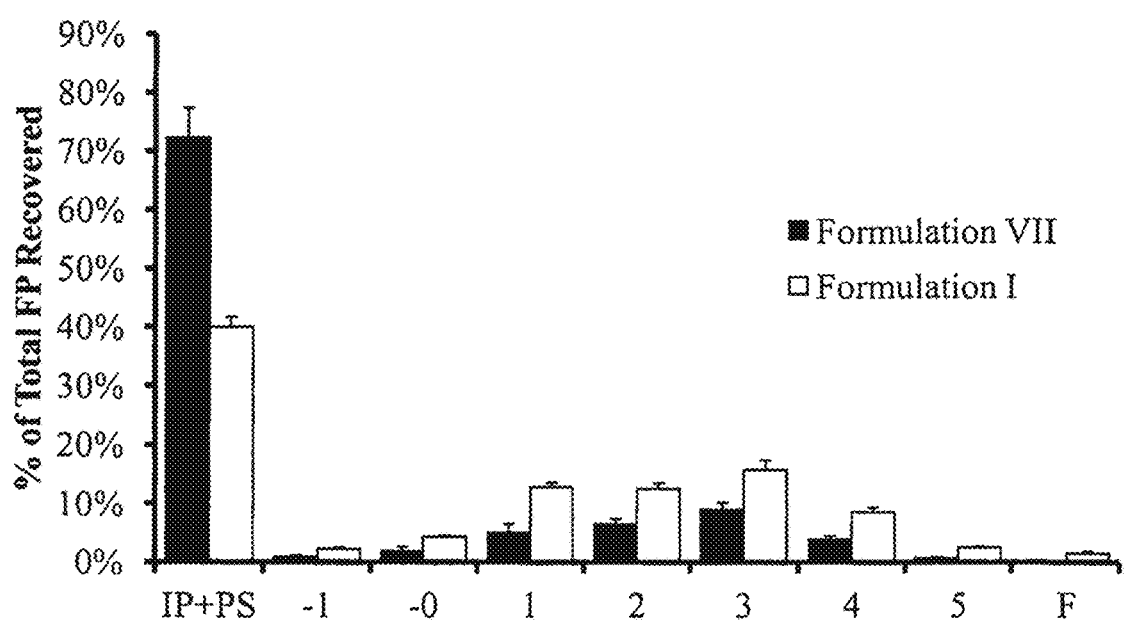
FIG. 2 is a plot of an Andersen Cascade Impactor, 8-stage (ACI-8) distribution for Formulation I, which specifically looks at the fluticasone propionate (FP) distribution when emitted from the Diskus® dry powder inhaler at a flow rate of 90 liters per minute (LPM). See, Example 7.

ACI (n=3) distributions are shown at 90 LPM for FP in FIG. 2 dispersed from the Diskus dry powder inhaler in four actuations. Data is normalized to the total amount of FP and SX recovered from the impactor by dividing the mass of each drug recovered from each component by the total mass of each drug recovered on all components. The fine particle fraction (FPF, percentage of emitted dose less than 4.7 μm) and mass median aerodynamic diameter (MMAD) of FP and SX delivered from the Diskus dry powder inhaler at 90 LPM is reported in 25.

TABLE 25

FPF and MMAD for FP and SX of Formulation I and Formulation VII dry powder from ACI testing at 90 LPM.

| | | FPF (as % of emitted dose) | | MMAD (of dose getting past IP; in microns) | |
|---|---|---|---|---|---|
| | | Average (n = 3) | Standard Deviation | Average (n = 3) | Standard Deviation |
| Formulation I emitted from Diskus ® | FP | 53.5 | 1.9 | 2.28 | 0.17 |
| | SX | 59.4 | 0.5 | 2.17 | 0.17 |
| Formulation VII emitted from Diskus ® | FP | 23.6 | 3.7 | 2.16 | 0.11 |
| | SX | 18.2 | 1.6 | 2.20 | 0.10 |

Formulation I demonstrates the ability to be administered from the Advair Diskus dry powder inhaler. Furthermore Formulation I has a greater delivery efficiency than Formulation VII dry powder. The fine particle fraction was higher for Formulation I because of reduced pre-separator and induction port deposition compared to Formulation VII at 90 LPM. Additionally, there is very good agreement between the Formulation I FP and SX distributions across all stages at both flow rates. This demonstrates that the spray dried powder of Formulation I has a uniform ratio of FP and SX across all measured particle diameters.

The size distribution of the powder mass that passed the pre-separator is similar for Formulation I and Formulation VII dry powders when dispersed from the Advair Diskus at 90 LPM, both in the magnitude of MMAD and in the relative distribution shape by stage.

Example 8. Dry Powder Metal Cation Salt-Based Formulations Delivered a Triple Combination Therapeutic Consistently to Different Stages on the ACI-8 from a Single-Unit Dose DPI (RS-01)

Formulation XI comprised of leucine, sodium citrate, fluticasone propionate (FP), and salmeterol xinafoate (SX), and tiotropium bromide (TioB). The composition of Formulation XI was 50.0% (w/w) leucine, 45.3% (w/w) sodium citrate, 4.0% FP, 0.58% SX, and 0.113% TioB. Formulation XI was produced by spray drying. A solution of the components was made, and then pumped to a spray dryer, which generated homogenous particles. Formulation XI was filled into size 3 HPMC capsules for dispersion in the RS01 HR dry powder inhaler. All capsules were filled with 20 mg of Formulation XI powder with 6 capsules actuated for each ACI8 measurement. ACI8 testing was performed (n=5) at 60 LPM. Stages used for 60 LPM tests were: IP, Entrance Cone, −1, −0, 1, 2, 3, 4, 5, 6, and F with corresponding lower stage cutpoints of: >8.6, 8.6, 6.5, 4.4, 3.3, 2.0, 1.1, 0.54, 0.25, and 0.0 rpm.

In brief, the ACI8 method used inverted stage plates with glass microfiber filters as impaction surfaces. These filters were each rinsed with 10 mL of rinse solution consisting of 50% acetonitrile and 50% reagent water. The induction port was rinsed with 30 mL of rinse solution and the mouthpiece adapter and entrance cone each rinsed with 5 mL of rinse solution. No pre-separator was used for these tests. The capsules were separated into the base and cap and were rinsed in a Petri dish with 10 mL of rinse solution.

Figure 3:
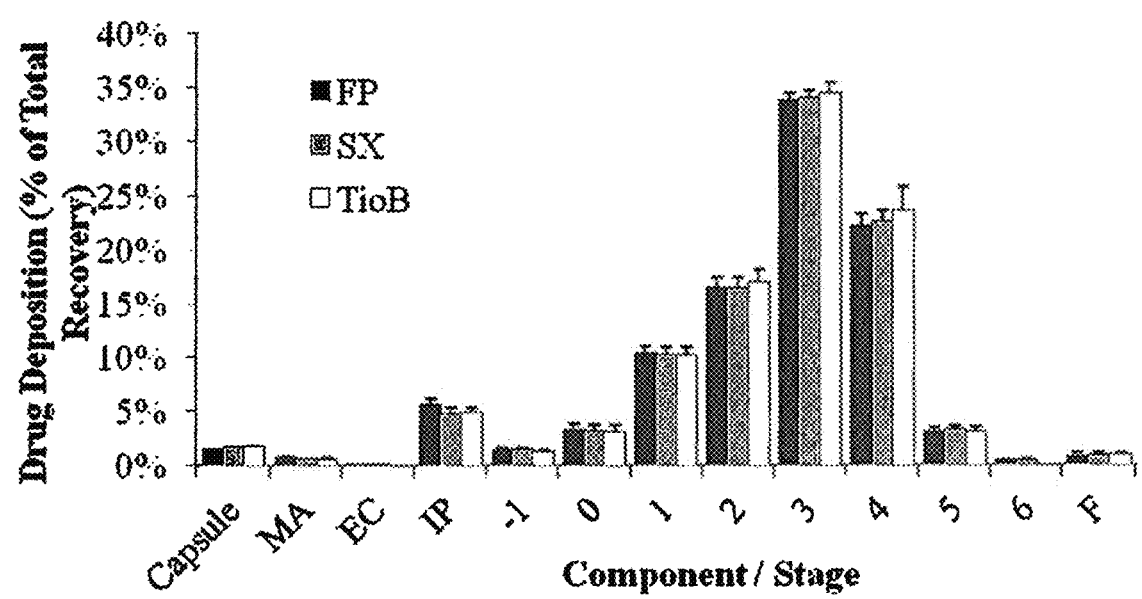
FIG. 3 is a plot of an Andersen Cascade Impactor, 8-stage (ACI-8) distribution for each of the three active agents in Formulation XI. Active agents may also be referred to as therapeutic agents. The RS-01 dry powder was used and a flow rate of 60 liters per minute (LPM) was used. See, Example 8.

ACI8 (n=5) distributions are shown at 60 LPM for FP, SX, and TioB in FIG. 3 as a percentage of the total amount of drug recovered, including the emitted dose (as measured by drug recovered from all sample collection surfaces in the impactor) and the powder retained in the capsules. Powder retained on the DPI could not be assayed due to interactions between the rinse solution and the DPI. The MMAD, GSD, and FPF (percentage of emitted dose less than 4.4 μm) are summarized in Table 26 for FP, SX, and TioB.

TABLE 26

MMAD, GSD, and FPF for FP, SX, and TioB of Formulation XI from ACI8 testing at 60 LPM.

|  | MMAD (micrometers) | | GSD | | FPF (as % of emitted dose) | |
|---|---|---|---|---|---|---|
|  | Average (n = 5) | Standard Deviation | Average (n = 5) | Standard Deviation | Average (n = 5) | Standard Deviation |
| Fluticasone propionate | 2.75 | 0.05 | 1.73 | 0.03 | 78.0 | 1.2 |
| Salmeterol xinafoate | 2.73 | 0.05 | 1.73 | 0.03 | 79.1 | 1.2 |
| Tiotropium bromide | 2.73 | 0.08 | 1.70 | 0.02 | 79.9 | 1.3 |

Visually, the distribution of FP, SX, and TioB across the impactor components and stages is nearly identical when dispersed at 60 LPM suggesting that the Formulation XI powder particles have homogenous compositions of three active ingredients across all measured particle diameters. The relative invariability of MMAD, GSD, and FPF for FP, SX, and TioB further supports that the ratio of the components is maintained across all measured particle diameters. Additionally, the delivery efficiency of the three active ingredients from the RS01 inhaler is high; on average, greater than 78% of the emitted dose is in a respirable size range less than 4.4 μm.

Example 9. Dry Powder Metal Cation Salt-Based Formulations Delivered from a Multi-Unit Dose DPI (Flexhaler Reservoir-Based DPI) Delivered Doses of Consistent Size Over Multiple Uses Formulation I, a spray dried, metal cation salt-based formulation of Fluticasone propionate (FP) and Salmeterol xinafoate (SX) with weight percentages of FP and SX matching the 500 mg of FP and 50 mg of SX strength doses of the dry powder found in the commercial product Advair®, was produced and characterized, as per Example 1 above. A Pulmicort Flexhaler® was obtained by commercial sources and emptied of drug formulation. Formulation I was filled into the empty Flexhaler multi-dose reservoir dry powder inhaler at controlled humidity conditions (30±5% RH). The dry powder was tested for volumetric particle size on a Spraytec Laser Diffraction System [Malvern Instruments, Westborough, Mass.] with the closed bench inhalation cell configuration. Five 2.0 L actuations were performed for each measurement at both pressure drops of 1.0 and 4.0 kPa across the inhaler which corresponded to 33.3 and 66.7 LPM flow rates through the DPI respectively.

Testing was performed at three different device and testing conditions: (1) at room conditions of 30±5% Relative Humidity (RH) when the Flexhaler reservoir was approximately 1/3 filled with Formulation I [30% RH], (2) at room conditions of 30±5% RH when the Flexhaler reservoir had been actuated until it was nearly empty [30% RH—Empty (E)], and (3) at room conditions of 60±5% RH when the Flexhaler reservoir was approximately 1/3 filled with powder [60% RH]. For the 60±5% RH condition, the Flexhaler was equilibrated at room conditions for approximately 2 hours before the beginning of the testing.

Figure 4:
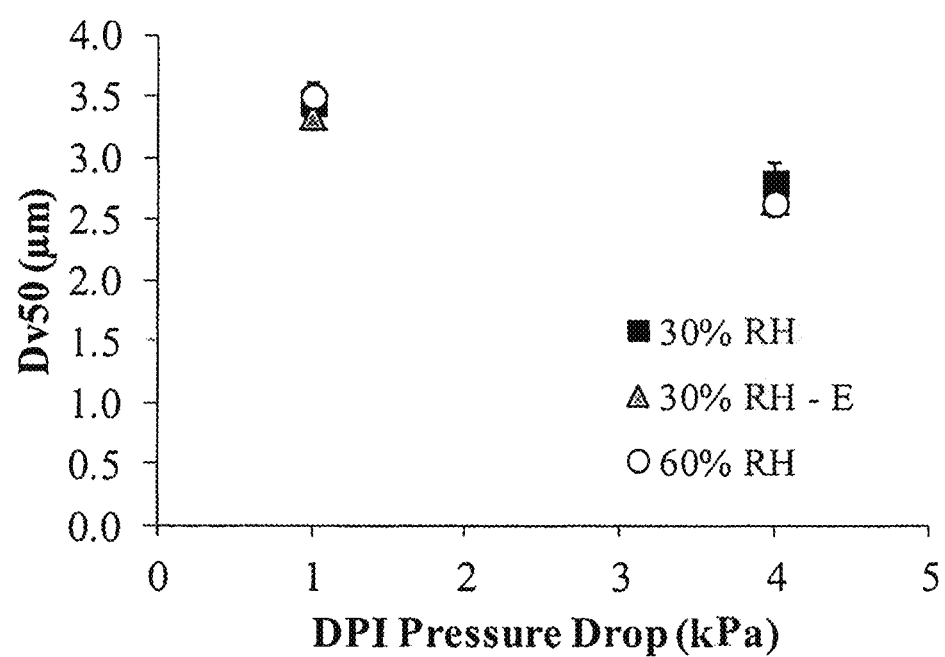
FIG. 4 is plot that contains values obtained from a Spraytec laser diffraction system used to measure geometric particle size distributions such as the average volume median diameter (Dv50). The Flexhaler multi-dose reservoir dry powder inhaler (DPI) was used to actuate Formulation I. The setup was run at simulated inhalation energies of 4.0 kPa and 1.0 kPa for three different testing condition; i) 30% relative humidity (RH) for a well-filled reservoir, ii) 30% RH for a nearly empty reservoir (E), and iii) 60% RH for a well-filled reservoir. See, Example 9.

The average volume median diameter (Dv50) and geometric standard deviation (GSD) of the Formulation I dry powder emitted from the Flexhaler DPI are plotted for the three testing conditions in FIG. 4, and summarized in Table 27.

TABLE 27

Dv50 and GSD of Formulation I emitted from the Flexhaler multi-dose reservoir dry powder inhaler at 1.0 and 4.0 kPa (n = 5).

|  |  | 1.0 kPa | | 4.0 kPa | | Ratio of |
|---|---|---|---|---|---|---|
|  | Condition | Average (n = 5) | Standard deviation | Average (n = 5) | Standard deviation | average Dv50 at 1.0 kPa to 4.0 kPa |
| Dv50 (microns) | 30% RH | 3.455 | 0.061 | 2.791 | 0.161 | 1.238 |
|  | 30% RH - E | 3.342 | 0.123 | 2.641 | 0.120 | 1.266 |
|  | 60% RH | 3.508 | 0.104 | 2.630 | 0.061 | 1.334 |
| GSD | 30% RH | 1.953 | 0.050 | 1.910 | 0.047 | NA |
|  | 30% RH - E | 1.903 | 0.015 | 1.899 | 0.061 |  |
|  | 60% RH | 1.936 | 0.034 | 1.872 | 0.016 |  |
| FPF (as % of emitted dose) | 30% RH | 70.48 | 1.32 | 78.98 | 3.12 | NA |
|  | 30% RH - E | 72.57 | 1.60 | 81.61 | 2.79 |  |
|  | 60% RH | 69.37 | 1.66 | 81.90 | 0.91 |  |

The volumetric particle size of Formulation I dry powder emitted from the Flexhaler inhaler is nearly identical between the each of the three testing conditions. There is very good agreement in the Dv50 and GSD between the conditions, suggesting that Formulation I powder emitted from the Flexhaler reservoir dry powder inhaler is not influenced by the fill volume of the reservoir nor the humidity of the testing environment, up to 60% RH, at inhaler pressure drops of 1.0 and 4.0 kPa. Additionally, powder emitted from the Flexhaler inhaler for each of the thirty actuations, indicating that Formulation I powder routinely flowed into the dosing disk under the influence of gravity alone and could be suitable for use in multi-dose, device metered reservoir dry powder inhalers, such as the Flexhaler. Furthermore, the low standard deviation in the measurements show that the dry powder repeatedly flowed into the dosing disk.

In the Flexhaler, Formulation I dry powder is not significantly flow rate dependent, however, there is a measureable and consistent increase in Dv50 as the flow rate decreases. This decrease in Dv50 may be attributable to the reduction in total inhalation energy at 1.0 kPa compared to 4.0 kPa where the intensity of particle collisions is reduced and hence particle deagglomeration is reduced.

Example 10

Example 10A. Comparison of ACI-8 Distributions of a Metal Cation Salt-Based FP/SX Formulation to a Lactose-Blended FP/SX Formulation I, a spray dried, metal cation salt-based formulation of Fluticasone propionate (FP) and Salmeterol xinafoate (SX) with weight percentages of FP and SX matching the 500 mg of FP and 50 mg of SX strength doses of the dry powder found in the commercial product Advair®, was produced and characterized, as per Example 1 above. An equivalent strength Formulation XVIII dry powder containing 500/50 FP/SX was obtained from commercial sources. Formulation XVIII contained 4% FP, 0.58% SX, and 95.4% lactose, all on a weight/weight basis. The formulations were filled into size 3 HPMC capsules for dispersion in the RS-01 high-resistance dry powder inhaler (RS-01 HR DPI). Formulation XVIII was removed from the blisters in which the product is sold. This removal took place at controlled humidity conditions (RH=30±5%), and both Formulations I and XVIII were hand filled into size 3 HPMC capsules at these controlled humidity conditions of RH=30±5%, for dispersion in the RS-01 HR DPI. All capsules were filled at a dry powder loading of 20 mg per capsule. Andersen Cascade Impactor 8-stage (ACI-8) characterization was run where four capsules were then actuated for each ACI-8 measurement. ACI-8 testing was performed in triplicate (n=3) at both 60 liters per minute (LPM) and 28.3 LPM, including a pre-separator for all tests. Stages used for 60 LPM tests were: an induction port (IP), a Pre-separator (PS), and stages −1, −0, 1, 2, 3, 4, 5, 6, filter (F) with corresponding lower stage cutpoints of: >8.6, 8.6, 6.5, 4.4, 3.3, 2.0, 1.1, 0.54, 0.25, 0.0 microns while for 28.3 LPM testing stages used were IP, PS, 0, 1, 2, 3, 4, 5, 6, 7, F with corresponding lower stage cutpoints of: >9.0, 9.0, 5.8, 4.7, 3.3, 2.1, 1.1, 0.70, 0.40, 0.0 microns.

ACI-8 testing was performed with the addition of a pre-separator for all runs. The method used inverted stage plates with glass microfiber filters as impaction surfaces. These filters were each rinsed with 10 mL of rinse solution consisting of 50% acetonitrile and 50% reagent water. The induction port was rinsed with a different 30 mL of the rinse solution, and the mouthpiece adapter was rinsed with an additional 10 mL of the rinse solution. The pre-separator was filled with 10 mL of the rinse solution prior to the ACI-8 run and then following the run, an additional 10 mL of rinse solution was added and the combined 20 mL used for rinsing the pre-separator.

Figure 5:
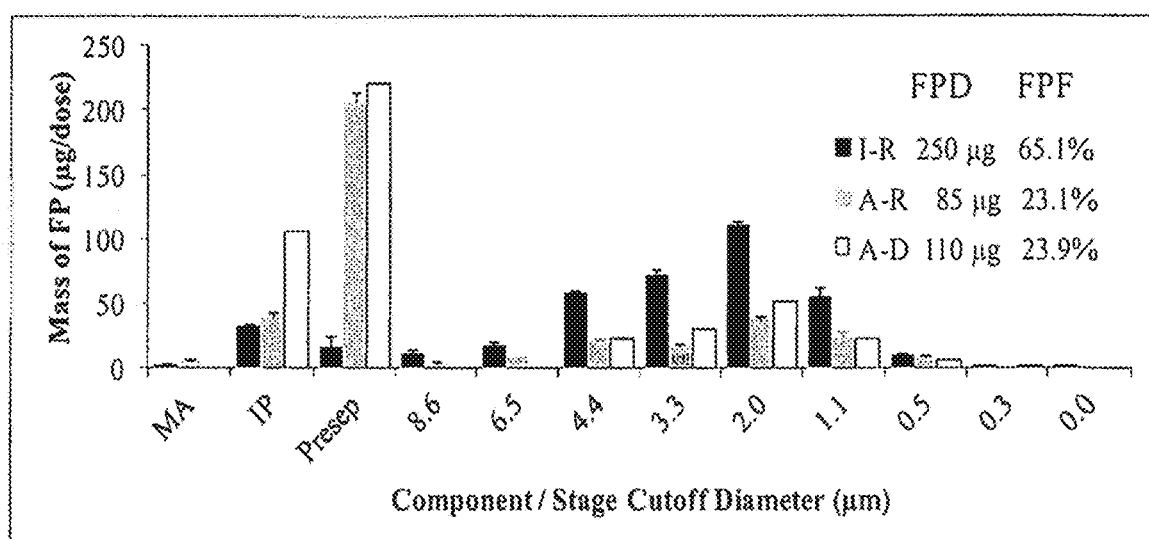
FIG. 5 is a plot of an Andersen Cascade Impactor, 8-stage (ACI-8) distribution. The "I-R" is Formulation I and "A-R" is Formulation FPSX, both run on the RS-01 dry powder inhaler at an inspiratory flow rate of 60 liters per minute (LPM). "A-D" is Formulation FPSX run on the Diskus®. The distribution includes the deposition on the mouthpiece adaptor, induction port (ID) and the pre-separator (PS). Values for fine particle dose and fine particle fraction are also reported on the figure. See, Example 10A.

ACI-8 (n=3) distribution values are shown for results at 60 LPM for FP in FIG. 5 and for both FP and SX in Table 28. The ACI-8 (n=3) distribution values are shown for results at 28.3 LPM for FP and SX in Table 29. For each ACI-8 measurement, 4 capsules of 20 mg fill weight each were used. Data is normalized from the 80 mg delivered to a 12.5 mg dose of 500/50. Data from Advair Diskus® 250/50 from Daley-Yates et al. Clin Ther (2009) at 60 LPM was scaled to 500/50 for comparison (A-D). The Advair 250/50 data was scaled to Advair 500/50 data by multiplying the FP content of the 250/50 data by 2 (there is twice as much FP in Advair 500/50 as there is in Advair 250/50. SX content is identical between the two formulations).). Stages reported by Daley-Yates et al. were: IP, PS+0, 1, 2, 3, 4, 5, 6, 7, F with corresponding lower stage cutpoints of: >6.2, 6.2, 4.0, 3.2, 2.3, 1.4, 0.8, 0.4, 0.3, 0.0 microns. The FPD and FPF reported for A-D are specific to aerodynamic particles sizes of less than 4.0 microns.

TABLE 28

ACI-8 Distribution for Formulation I for FP and SX at 60 LPM

| Formulation # (Dry Power Device) | 60 Liters per minute | | | | | |
|---|---|---|---|---|---|---|
| | Fluticasone propionate | | | Salmeterol xinafoate | | |
| | I RS-01 | XVIII RS-01 | XVIII Diskus® | I RS-01 | XVIII RS-01 | XVIII Diskus® |
| Part of ACI-8 setup | | | | | | |
| Mouth-piece adapter | 2.5 | 5.1 | NR | 0.5 | 0.9 | NR |
| Induction Port | 31.7 | 39.7 | 105.8 | 4 | 6.2 | 16 |
| Pre-separator | 15.7 | 205.3 | 221 | 1.2 | 31 | 33.1 |
| 8.6 | 10.3 | 4 | NR | 1.2 | 0.7 | NR |
| 6.5 | 17 | 7.6 | NR | 2 | 1.1 | NR |
| 4.4 | 57.2 | 20.1 | 22.8 | 6.2 | 2.7 | 3.3 |
| 3.3 | 71.8 | 16.7 | 30.6 | 7.8 | 2 | 4.2 |
| 2 | 110.2 | 36.3 | 51.4 | 12.3 | 4.8 | 7.5 |
| 1.1 | 55.5 | 23.7 | 22 | 6.5 | 3.7 | 2.8 |
| 0.5 | 10 | 7.9 | 5 | 1.3 | 1.4 | 1.7 |
| 0.3 | 1.2 | 0.4 | 1.4 | 0.4 | 0.2 | 0.6 |
| 0 | 1 | 0 | 0 | 0.4 | 0.1 | 0 |

"NR" stands for "not reported", since these values were not reported in the Daley-Yates presentation cited above.

TABLE 29

ACI-8 Distribution for Formulation I for FP and SX at 28.3 LPM

| Formulation # | 28.3 Liters per minute | | | |
|---|---|---|---|---|
| | Fluticasone propionate | | Salmeterol xinafoate | |
| | I | XVIII | I | XVIII |
| (Dry Powder) Device | (RS-01) | (RS-01) | (RS-01) | (RS-01) |
| Part of ACI-8 setup | | | | |
| Mouth-piece adapter | 4.2 | 4.7 | 0.6 | 0.9 |
| Induction Port | 43.1 | 51.6 | 1.9 | 8.1 |
| Pre-separator | 15.7 | 218 | 1.7 | 32.1 |
| 9 | 9.9 | 9.6 | 1.1 | 1.6 |
| 5.8 | 21 | 11.9 | 2.3 | 1.8 |
| 4.7 | 30.1 | 9.4 | 3.2 | 1.4 |
| 3.3 | 85.9 | 22.2 | 9.3 | 3 |
| 2.1 | 101.9 | 27.4 | 11.4 | 3.8 |
| 1.1 | 52.1 | 14.6 | 6.1 | 2.1 |
| 0.7 | 5.5 | 0.9 | 0.8 | 0.3 |
| 0.4 | 0.9 | 0 | 0.2 | 0 |
| 0 | 1.8 | 0 | 0.2 | 0 |

Example 10B. Comparison of FPD and FPF of a Metal Cation Salt-Based FP/SX Formulation to a Lactose-Blended FP/SX Lactose blend formulations are used to administer a discreet subset of available respiratory therapeutics to the respiratory tract. The therapeutic needs to be micronized in order to be of a proper size range for delivery to the respiratory tract, namely between about 1-5 microns. These formulations contain large, non-respirable lactose carrier particles to assist in the aerosolization of micronized therapeutics due to the difficulty in entraining and deagglomerating formulations of just micronized therapeutic due to their relatively high inter-particulate forces. While the lactose is helpful in aerosolizing the micronized therapeutic, one problem that faces these lactose blend formulations is that the lactose takes up a large percentage of the volume and mass in a typical dosage form, leaving only a relatively small volume for the therapeutic. A second problem these lactose blend formulations face is that it is difficult to separate the micronized therapeutic particles from the lactose carriers, which leads to significant amounts of the therapeutic being deposited in the back of the mouth with the lactose carrier, and subsequently swallowed. This effect is magnified when a patient inhales at a lower inspiratory flow rate energy than the standard 4 kPa pressure drop test conditions. A differential pressure across the dry powder inhaler (DPI) of 4 kPa represents a flow rate of approximately 60 LPM using the RS-01 high-resistance (HR) dry powder inhaler (DPI) and approximately 90 LPM using the Diskus® (GlaxoSmithKline (GSK)).

Figure 6:
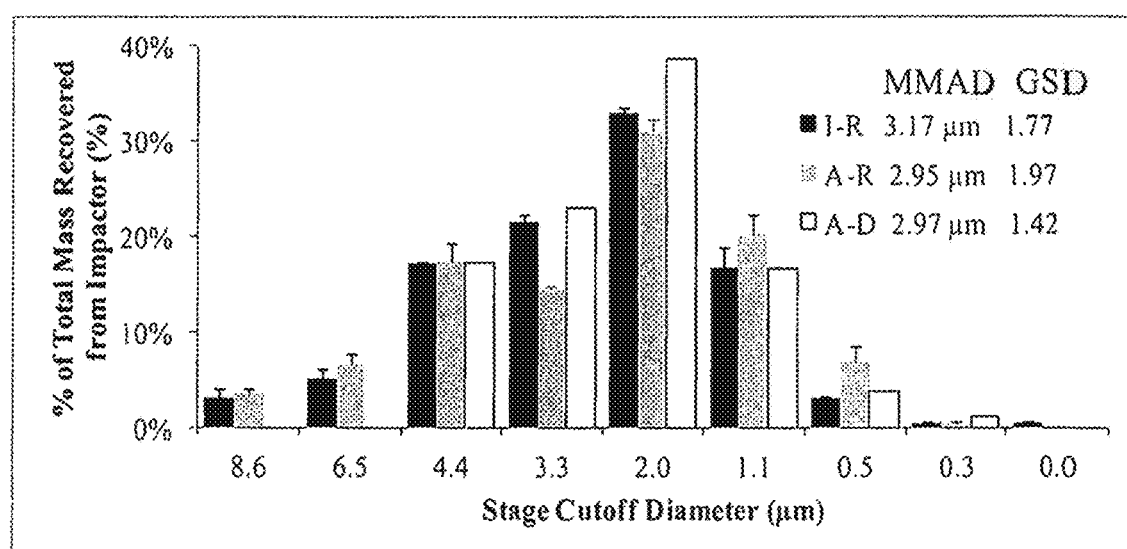
FIG. 6 is a plot of an Andersen Cascade Impactor, 8-stage (ACI-8) distribution. The "I-R" is Formulation I and "A-R" is Formulation FPSX, both run on the RS-01 dry powder inhaler at an inspiratory flow rate of 60 liters per minute (LPM). "A-D" is Formulation FPSX run on the Diskus®. The distribution only includes powder that deposited after the MA, ID and PS. Values for the mass median aerodynamic diameter (MMAD) and the geometric standard deviation (GSD) are also reported on the figure. See, Example 10B.

One way to contrast the effects of lactose carrier particle is to measure the fine particle dose (FPD) and fine particle fraction (FPF) of the starting dose. The FPD less than 4.4 microns at 60 LPM and the FPD less than 4.7 microns at 28.3 LPM are reported in Table 30 for Formulations I and FPSX when administered with the RS-01 DPI. Additionally, values for Formulation FPSX were taken from the literature (in Daley-Yates et al.) when administered with a Diskus® DPI. The data from that article was for FPD less than 4.0 microns. The FPD and FPF for Formulation I when administered with the RS-01 DPI was found to be higher than for Formulation FPSX administered with the RS-01 DPI and with the Diskus®. This was due in large part by the reduced pre-separator deposition for Formulation I compared to Formulation FPSX at both 60 and 28.3 LPM. The FPD data is shown in Table 30 below. Comparison of the losses in the induction port and the pre-separator can be observed in previous Tables 28 and 29 and FIG. 6.

TABLE 30

FPF, FPD, and ED for Fluticasone Propionate Formulations I and XVIII at 60 LPM and 28.3 LPM.

| Therapeutic | Parameter measured | Formulations I (RS-01 DPI) | | Formulation XVIII (RS-01 DPI) | | Formulation XVIII |
|---|---|---|---|---|---|---|
| | | 60 LPM | 28.3 LPM | 60 LPM | 28.3 LPM | (Diskus ® DPI) 60 LPM |
| Fluticasone Propionate (FP) | FPD (micrograms) | 250 | 248 | 85 | 65 | 110 |
| | FPD and FPF stage cutoffs (microns) | <4.4 | <4.7 | <4.4 | <4.7 | <4.0 |
| | Emitted Dose (micrograms) | 384 | 372 | 367 | 370 | 463 |
| | FPF (as % of emitted dose) | 65.1% | 67.3% | 23.1% | 17.6% | 23.9% |

In an in vitro cascade impactor such as the ACI-8, the effect described above is typically detected by observing high quantities of the therapeutic in the induction port and pre-separator components, which is where the lactose carrier particles typically deposit. However, using the dry powder metal cation salt formulations as described herein, such as Formulation I, there is no need to include large carrier particles such as lactose carrier particles to aerosolize the dry powder formulation. Therefore, when delivering a therapeutic with a dry powder metal cation salt Formulation I, for example, only deagglomeration of the particles is required, while when delivering a therapeutic with a lactose carrier particles, both deagglomeration and a secondary detachment step are needed. The avoidance for this secondary detachment step coupled with the particles ability to deagglomerate in a respirable size leads to much lower pre-separator drug deposition for the dry powder metal cation salt-based formulations, and hence a larger portion of the emitted dose being delivered to the lower stages of the ACI-8 in vitro setup. A similar result in the respiratory tract of a patient is predicted by the ACI-8 results. In practice this would allow for reduced amounts of drug to be loaded into a dosage unit in order to achieve the same efficacious dose to the patient. A secondary benefit is that less dose ends up in the oral cavity, digestive tract, and subsequently into systemic circulation, where the therapeutic would be more likely to lead to undesired side effects.

An additional observation that is evident from this experiment is the relative independence of FPD to inhalation energy that was observed for the dry powder salt-based Formulation I, and the relative dependence of FPD to inhalation energy that was observed for the lactose blend Formulation FPSX. The FPD for Formulation I over varying inhalation energies using the RS-01 HR DPI, at the flow rates of 60 LPM and 28.3 LPM, approximately representing inhalation energies of 4.0 kPa and 1.0 kPa, was 250 micrograms and 248 micrograms, respectively. In comparison, the FPD for Formulation FPSX over varying inhalation energies using the RS-01 HR DPI, at the flow rates of 60 LPM and 28.3 LPM, was 85 micrograms and 65 micrograms. The FPD for Formulation FPSX at 28.3 LPM dropped by 20 micrograms, which was greater than a 20% drop, whereas the FPD for Formulation I at 28.3 LPM dropped by 2 micrograms, which was less than a 1% drop. This demonstrated that the dry powder metal cation salt-based formulation had a more uniform delivery over varying simulated inhalation flow rates, and therefore energies, than the lactose-blend of Formulation FPSX.

Example 11. Comparison of MMAD of Formulations I and XVIII after the Induction Port and Pre-Separator The size distribution of the powder mass that passed the pre-separator was compared for the example described in Example 5 above. This data was presented in Tables 14 and 15. In order to compare the size distributions, the MMAD for Formulations I and FPSX was determined, where the MMAD only took into account the dose that passed the pre-separator. The data may be seen in FIG. 2 where just the FP measurements for Formulations I and FPSX were displayed, and in Table 31 below where both the FP and SX measurements were reported.

TABLE 31

Comparison of MMAD of Formulations I vs. XVIII after the Induction Port and Preseperator, for both FP and SX at 60 LPM and 28.3 LPM on the RS-01.

| Therapeutic | Parameter | Formulation I (RS-01 DPI) | | Formulation XVIII (RS-01 DPI) | |
|---|---|---|---|---|---|
| | | 60 LPM | 28.3 LPM | 60 LPM | 28.3 LPM |
| FP | MMAD (micrometers) | 3.17 | 3.21 | 2.95 | 3.62 |
| SX | MMAD (micrometers) | 3.11 | 3.16 | 2.80 | 3.66 |

This data show that the MMAD as measured at 60 LPM for the dry powder salt-based Formulation I was roughly comparable to the MMAD as measured at 60 LPM for the lactose-blend Formulation FPSX. The MMAD for FP and SX at 60 LPM for Formulation I was 3.2 microns and 3.1 microns, respectively, and for Formulation FPSX was 3.0 microns and 2.8 microns, respectively. The MMAD values, as measured at 28.3 LPM for the dry powder salt-based Formulation I, was 3.2 microns for both FP and SX, which was quite consistent as the values measured at 60 LPM, namely 3.1 microns and 3.2 microns, for FP and SX, respectively. However, the MMAD values as measured at 28.3 LPM for the lactose-blend Formulation FPSX increased to 3.6 microns for FP and 3.7 microns for SX, a notable increase from 3.0 microns and 2.8 microns for FP and SX, respectively, at 60 LPM. This data demonstrated that the dry powder metal cation salt-based Formulation I was less dependent on inspiratory flow rate than the lactose blend-based Formulation FPSX.

Example 12. High Therapeutic Agent Loading with High Density

Formulations containing therapeutic agents from some of the common classes of therapeutic agents used to treat respiratory diseases such as COPD and asthma, and a model macromolecule were manufactured. Representative classes included long acting beta-adrenoceptor agonist (LABA), with formoterol fumarate tested, long-acting muscarinic antagonist (LAMA), with tiotropium bromide and glycopyrrolate tested, and antibodies (immunoglobulin G (IgG)).

A. Powder Preparation.

Feedstock solutions were prepared in order to manufacture dry powders comprised of at least one metal cation salt and relatively high amounts of a therapeutic agent. The formulations described below each contained one or two metal cation salts, an excipient, and a therapeutic agent. The therapeutic agent for each formulation was between 50% and 60%, (w/w) of the overall dry powder composition, on a dry basis.

In order to assess if higher load and lower load therapeutic agent formulations could be produced with comparable properties, one of the therapeutic agents was also formulated at 10% and 30% loading. The therapeutic agent chosen was tiotropium bromide.

TABLE 32

Feedstock compositions of respiratory therapeutic agents with metal cation salts.

| Formulation | Salt #1 | Salt #1 (w/w) (%) | Salt #2 | Salt #2 (w/w) (%) | Excipient | Excipient load (w/w) (%) | Therapeutic | Therapeutic load (w/w) (%) |
|---|---|---|---|---|---|---|---|---|
| XII | Sodium chloride | 2.5 | Calcium Lactate | 37.5 | Leucine | 10 | Formoterol Fumarate | 50 |
| XIII | Sodium chloride | 2.5 | Calcium Lactate | 37.5 | Leucine | 10 | Tiotropium Bromide | 50 |
| XIV | Sodium chloride | 2.5 | Calcium Lactate | 37.5 | Leucine | 10 | Glycopyrrolate Bromide | 50 |
| XV | Sodium chloride | 10 | N/A | N/A | Trehalose | 30 | IgG | 60 |
| XVI | Sodium chloride | 3.5 | Calcium Lactate | 52.5 | Leucine | 14 | Tiotropium Bromide | 30 |
| XVII | Sodium chloride | 4.5 | Calcium Lactate | 67.5 | Leucine | 18 | Tiotropium Bromide | 10 |

N/A = not applicable

The feedstock solutions were made according to the parameters in Table 33.

TABLE 33

Formulation Conditions

| Formulation: | XII | XIII | XIV | XV | XVI | XVII |
|---|---|---|---|---|---|---|
| Total solids (g) | 1.5 | 2.0 | 1.5 | 3 | 2 | 2 |
| Total volume water (L) | 1.0 | 0.2 | 0.15 | 0.1 | 0.07 | 0.1 |
| Total volume ethanol (L) | N/A | 0.13 | N/A | N/A | 0.13 | 0.1 |
| Total solids concentration (g/L) | 1.5 | 10 | 10 | 30 | 10 | 10 |
| Amount of NaCl in 1 L (g) | 0.04 | 0.25 | 0.25 | 3 | 0.35 | 0.45 |
| Amount of NaSulf in 1 L (g) | N/A | N/A | N/A | N/A | N/A | N/A |
| Amount of CaLact in 1 L (g) | 0.56 | 3.75 | 3.75 | N/A | 5.25 | 6.75 |
| Amount of MgLact in 1 L (g) | N/A | N/A | N/A | N/A | N/A | N/A |
| Amount leucine in 1 L (g) | 0.15 | 1.0 | 1.0 | N/A | 1.4 | 1.8 |
| Amount Levofloxacin in 1 L (g) | N/A | N/A | N/A | N/A | N/A | N/A |
| Amount Formoterol Fumarate in 1 L (g) | 0.75 | N/A | N/A | N/A | N/A | N/A |

TABLE 33-continued

Formulation Conditions

| Formulation: | XII | XIII | XIV | XV | XVI | XVII |
|---|---|---|---|---|---|---|
| Amount Tiotropium Bromide in 1 L (g) | N/A | 5.0 | N/A | N/A | 3.0 | 5.0 |
| Amount Glycopyrrolate Bromide in 1 L (g) | N/A | N/A | 5.0 | N/A | N/A | N/A |
| Amount of Trehalose in 1 L (g) | N/A | N/A | N/A | 9 | N/A | N/A |
| IgG in 1 L (g) | N/A | N/A | N/A | 18 | N/A | N/A |

Note:
For all formulations, the liquid feedstock was batch mixed. (N/A = not applicable)

Formulation XII through XVII dry powders were produced by spray drying on the Büchi B-290 Mini Spray Dryer (BÜCHI Labortechnik AG, Flawil, Switzerland) with powder collection from a High Performance cyclone in a 60 mL glass vessel. The system used the Büchi B-296 dehumidifier Atomization of the liquid feed utilized a Büchi two-fluid nozzle with a 1.5 mm diameter. The two-fluid atomizing gas was set at 40 mm (667 LPH). The aspirator rate was set to 100% (38 m³/h) for Formulations XII, XIII, XV, XVI and XVII; to 70% (28 m³/h) for Formulation XIV. Air was used as the drying gas and the atomization gas. Table 34 below includes details about the spray drying conditions.

TABLE 34

Spray Drying Process Conditions

| Process Parameters | XII | XIII | XIV | XV | XVI | XVII |
|---|---|---|---|---|---|---|
| Liquid feedstock solids concentration (g/L) | 1.5 | 10 | 10 | 30 | 10 | 10 |
| Process gas inlet temperature (° C.) | 180 | 160 | 180 | 80 | 160 | 160 |
| Process gas outlet temperature (° C.) | 93-95 | 87 | 83 | 46 | 80 | 84 |
| Process gas flow rate (liter/hr, LPH) | 667 | 667 | 667 | 667 | 667 | 667 |
| Atomization gas flow rate (meters³/hr) | 38 | 38 | 28 | 38 | 38 | 38 |
| Liquid feedstock flow rate (mL/min) | 5.5 | 10.0 | 5.5 | 2.5 | 9.5 | 9.5 |

B. Powder Characterization.

Powder physical and aerosol properties are summarized in Tables 35 to 39 below. Values with ± indicate standard deviation of the value reported. Two-stage ACI2 results are reported in Table 35 for fine particle fraction of the total dose less than 3.4 microns or less than 5.6 microns, $FPF_{TD}$<3.4 microns and $FPF_{TD}$<5.6 microns. Formulations XII, XIII and XVI had $FPF_{TD}$<3.4 values above 50% and all formulations has $FPF_{TD}$<5.6 above 50%, with Formulations XII and XIII above 75%.

TABLE 35

Aerodynamic properties

| | ACI2 | |
|---|---|---|
| | $FPF_{TD}$ < 3.4 microns | $FPF_{TD}$ < 5.6 microns |
| Formulation | % | % |
| XII | 55.05 ± 3.14 | 75.26 ± 0.99 |
| XIII | 56.94 ± 1.43 | 76.47 ± 1.47 |
| XIV | 29.50 ± 0.60 | 51.37 ± 0.98 |
| XV | 19.09 ± 1.22 | 50.10 ± 4.26 |

TABLE 35-continued

Aerodynamic properties

| | ACI2 | |
|---|---|---|
| | $FPF_{TD}$ < 3.4 microns | $FPF_{TD}$ < 5.6 microns |
| Formulation | % | % |
| XVI | 50.63 ± 0.80 | 69.28 ± 1.55 |
| XVII | 47.91 ± 0.65 | 66.77 ± 1.09 |

Table 36 reports the tap densities, bulk densities and Hausner Ratios for each of the formulations. All formulations had a tapped density greater than 0.50 g/cc, with Formulations XII, XIV, XVI and XVII all being above 0.65 g/cc. The bulk densities ranged from 0.27 g/cc to 0.46 g/cc. Formulations XII, XIV, XV and XVI had Hausner Ratios above 1.7. Interestingly, Formulation XIII had a Hausner Ratio of 1.23.

TABLE 36

Density properties

| | Density | | |
|---|---|---|---|
| Formulation | Bulk g/cc | Tapped g/cc | Hausner Ratio |
| XII | 0.37 ± 0.02 | 0.67 ± 0.11 | 1.79 |
| XIII | 0.46 ± 0.06 | 0.57 ± 0.05 | 1.23 |
| XIV | 0.31 ± 0.07 | 0.74 ± 0.04 | 2.39 |
| XV | 0.27 ± 0.04 | 0.56 ± 0.05 | 2.09 |
| XVI | 0.35 ± 0.08 | 0.72 ± 0.06 | 2.07 |
| XVII | 0.39 ± 0.07 | 0.67 ± 0.03 | 1.70 |

Table 37 shows that Formulations XII, XIII, XIV, XVI and XVII had geometric diameters (Dv50) of less than 2.2 microns when emitted from a dry powder inhaler at a flowrate of 60 LPM, and less or equal to 3.5 microns when emitted from a dry powder inhaler at a flowrate of 15 LPM.

TABLE 37

Geometric Diameters

| | Dispersibility - Spraytec | | | |
|---|---|---|---|---|
| | @ 60 LPM | | @ 15 LPM | |
| Formulation | Dv50 (microns) | GSD | Dv50 (microns) | GSD |
| XII | 0.87 ± 0.08 | 5.14 ± 0.44 | 2.93 ± 0.06 | 3.43 ± 0.08 |
| XIII | 1.15 ± 0.08 | 5.60 ± 0.22 | 3.20 ± 0.20 | 4.52 ± 0.45 |
| XIV | 2.16 ± 0.14 | 5.19 ± 0.61 | 3.49 ± 0.12 | 3.21 ± 0.18 |
| XV | 3.40 ± 0.07 | 4.42 ± 0.11 | N/A ± | N/A ± |
| XVI | 1.32 ± 0.09 | 2.56 ± 0.15 | 2.87 ± 0.20 | 2.64 ± 0.14 |
| XVII | 1.19 ± 0.08 | 2.76 ± 0.05 | 2.70 ± 0.12 | 2.49 ± 0.16 |

N/A = not available

Table 38 shows that Formulations XII, XIII, XIV, XVI and XVII had a capsule emitted particle mass (CEPM) of greater than 96% at 60 LPM. Formulations XII, XIII, XIV and XVII had a CEPM of greater than 80% at 15 LPM.

TABLE 38

Dispersibility properties

| Formulation | Dispersibility - CEPM | |
|---|---|---|
| | @ 60 LPM CEPM | @ 15 LPM CEPM |
| XII | 97.22 ± 0.71% | 86.69 ± 4.20% |
| XIII | 96.54 ± 0.48% | 80.77 ± 10.97% |
| XIV | 99.10 ± 0.09% | 95.12 ± 4.37% |
| XV | 96.72 ± 1.685 | N/A ± |
| XVI | 97.85 ± 0.31% | 76.92 ± 17.70% |
| XVII | 97.78 ± 0.23% | 92.92 ± 2.31% |

N/A = not available

Table 39 shows that all formulations analyzed had a Dv50 equal or less than 1.8 microns using the RODOS at a 1.0 bar setting. All measured formulations had a RODOS Ratio for 0.5 bar/4 bar of less than 1.2, and a RODOS Ratio for 1 bar/4 bar of less than 1.1.

TABLE 39

Dispersibility properties (Geometric diameter using RODOS)

| | RODOS | | | | | | | |
|---|---|---|---|---|---|---|---|---|
| | 0.5 bar | | 1.0 bar | | 4.0 bar | | | |
| Form. | Dv50 (μm) | GSD | Dv50 (μm) | GSD | Dv50 (μm) | GSD | 0.5/4 bar | 1/4 bar |
| XII | 1.12 | 2.15 | 1.05 | 2.03 | 1.03 | 2.10 | 1.09 | 1.02 |
| XIII | 1.50 | 2.16 | 1.38 | 2.13 | 1.29 | 2.07 | 1.16 | 1.07 |
| XIV | 1.95 | 2.20 | 1.81 | 2.27 | 1.76 | 2.33 | 1.11 | 1.03 |
| XV | 3.14 | 2.27 | 2.91 | 2.31 | 2.69 | 2.35 | 1.17 | 1.08 |
| XVI | 1.62 | 2.19 | 1.61 | 2.21 | 1.49 | 2.18 | 1.08 | 1.09 |
| XVII | 1.57 | 2.24 | 1.48 | 2.25 | 1.35 | 2.23 | 1.10 | 1.16 |

Formulations XII through XV illustrate how dry powders utilizing metal cation salts such as sodium-based salts and calcium-based salts can be formulated with 50% or more therapeutic agent while still maintaining superior performance characteristics. The therapeutics used in Formulations XII through XIV are highly potent. Therefore, only a small volume of the dry powder would be needed in a unit dose to deliver an effective amount of the therapeutic agent to a subject in need thereof.

The data show that a formulation with a higher load of a therapeutic agent (Formulation XIII, 50% tiotropium bromide) and formulations with a lower load of a therapeutic agent (Formulations XVI and XVII, 30% and 10% tiotropium bromide, respectively) exhibited comparable particle and aerosol properties.

Example 13. High Dry Powder Mass Delivery from a Unit Dose

A high load antibiotic Formulation IX was filled into size 3 capsules with fill weights of 40 mg, 100 mg, and 120 mg. Processability and dispersibility were assessed by measuring the CEPM and DV(50) at 60 LPM using the RS-01 dry powder inhaler.

TABLE 40

Fill weights of 40, 100 and 120 mg where tested for CEPM and Dv(50) at 60 LPM.

| Formulation | Fill Weight (mg) | CEPM (at 60 LPM) | Dv(50) (microns) (at 60 LPM) | GSD |
|---|---|---|---|---|
| IX | 40 | 99% ± 0% | 1.56 ± 0.18 | 3.01 ± 0.08 |
| IX | 100 | 100% ± 0% | 1.68 ± 0.20 | 2.96 ± 0.23 |
| IX | 120 | 100% ± 0% | 1.47 ± 0.28 | 3.05 ± 0.20 |

Duration of measurement = 2 seconds, Inhaled energy = 8.32 Joules

Table 41 shows a high load antibiotic Formulation IX was filled into size 3 capsules with fill weights of 40 mg and 80 mg. The aerodynamic size distribution was assessed with an Anderson Cascade Impactor (ACI) run at standard conditions of 60 LPM for 2 seconds using the RS-01 DPI. This represents an inhaled energy of 8.32 Joules. The distributions of therapeutic (Levofloxacin) on the various plates is compared for the two different fill weights to contrast the effect of doubling the powder load in the capsule. Comparing the weight of therapeutic for each plate reveals that the aerodynamic size distributions for the two fill weights is overlapping, a result which is confirmed by the mass median aerodynamic diameter (MMAD) and geometric standard deviation (GSD) measurements. The MMAD and GSD for the 40 mg capsule fill weight was 4.79 and 1.81, respectively. The MMAD and GSD for the 80 mg capsule fill weight was 4.84 and 1.83, respectively. The fine particle dose less than 4.4 microns (FPF(<4.4)) was 13.20 mg and 24.52 mg for the 40 mg and 80 mg capsule fill weights, respectively.

TABLE 41

ACI-8 Distribution

Formulation IX; ACI-8 run at 60.0 LPM
(RS-01 dry powder inhaler; using size 3 capsules)

| Capsule fill weight | 40 mg capsule fill weight | 80 mg capsule fill weight |
|---|---|---|
| Capsule | 0.9% ± 0.1% | 0.5% ± 0.0% |
| Dry Powder Inhaler | 3.7% ± 0.1% | 2.9% ± 0.1% |
| Mouth-piece adapter | 0.7% ± 0.1% | 0.5% ± 0.1% |
| Entrance Cone | 0.2% ± 0.0% | 0.2% ± 0.0% |
| Induction Port | 7.1% ± 0.6% | 7.7% ± 0.4% |
| 8.6 | 6.6% ± 0.8% | 7.1% ± 0.7% |
| 6.5 | 13.3% ± 1.1% | 13.1% ± 0.6% |
| 4.4 | 20.7% ± 0.8% | 17.9% ± 1.7% |
| 3.3 | 12.5% ± 1.0% | 11.7% ± 1.2% |
| 2.0 | 12.4% ± 1.0% | 11.3% ± 1.1% |
| 1.1 | 5.1% ± 0.2% | 4.8% ± 0.2% |
| 0.54 | 1.4% ± 0.1% | 1.2% ± 0.1% |
| 0.25 | 0.8% ± 0.0% | 0.7% ± 0.0% |
| 0.00 | 0.8% ± 0.1% | 0.8% ± 0.0% |
| MMAD | 4.79 ± 0.16 | 4.84 ± 0.11 |
| GSD | 1.81 ± 0.02 | 1.83 ± 0.02 |
| FPD(<4.4 microns) of levofloxacin (mg) | 13.20 ± 0.79 | 24.52 ± 2.01 |

Illustrated in this example is how a formulation comprising a metal cation salt, and excipient, and a high load of a therapeutic agent can deliver high quantities of therapeutic agent to the respiratory tract, as simulated by the ACI.

Example 14. High Masses of Antibiotic (Levofloxacin) in Dry Particles

Illustrated in this example are the advantages of formulating a therapeutic as a dry powder with metal cation salts and optionally other excipients. Formulation IX was processed by spray drying, as described above in Example 6. Formulation 14-A was a 100% Levofloxacin formulation also processed by spray drying, following the process described in Example 6 above for Formulation IX.

Table 42 compares the two spray dried powders. Formulation IX has a higher density (tap density of 0.82 g/cc vs. 0.60 g/cc), has a smaller aerodynamic distribution (FPF<5.6 microns of 61.8% vs. 31.6%), and has a smaller geometric diameter (VMGD of 1.64 microns vs. 2.87 microns) than Formulation 14-A. The dispersibility ratio (0.5 bar/4.0 bar using the RODOS/HELOS) was 1.10 for Formulation IX and 1.39 for Formulation 14-A.

TABLE 42

Comparison of dry powder properties for Formulations IX and 14-A

| Formulation | Tap Density (g/cc) | FPF < 5.6 microns by 2-stage ACI (microns) | VMGD at 1.0 bar by RODOS/ HELOS (microns) | Dispersibility Ratio 0.5 bar/ 4.0 bar (RODOS/ HELOS) |
|---|---|---|---|---|
| IX | 0.82 ± 0.01 | 61.80 ± 0.80 | 1.64 | 1.10 |
| 14-A | 0.60 ± 0.01 | 31.60 ± 1.50 | 2.87 | 1.39 |

Table 43 compares the CEPM and Dv(50) over varying flowrates. This testing technique provides insight both into the processability of a dry powder, (e.g., how it fluidizes in the capsule), and the dispersibility, (e.g., how it de-agglomerates once the powder bed is fluidized). The Dv(50) for Formulation IX was 1.53 microns at 60 LPM and only rose to 2.71 microns at 15 LPM whereas the Dv(50) for Formulation 14-A was 4.96 microns at 60 LPM and rose to 68.68 microns. The CEPM for Formulation IX was 98.79% at 60 LPM and only dropped to 87.79% at 15 LPM. The CEPM for Formulation 14-A was 90.76% at 60 LPM and dropped to 36.73% at 15 LPM.

TABLE 43

Comparison of CEPM and Dv(50) over varying flowrates for Formulations IX and 14-A

| Form | @ 60 LPM (microns) | @ 30 LPM (microns) | @ 20 LPM (microns) | @ 15 LPM (microns) |
|---|---|---|---|---|
| | Dv(50) Over Varying Flowrates | | | |
| IX | 1.53 ± 0.12 | 1.66 ± 0.10 | 2.15 ± 0.07 | 2.71 ± 0.07 |
| 14-A | 4.96 ± 0.43 | 12.23 ± 1.81 | 42.54 ± 3.97 | 68.68 ± 7.26 |
| | CEPM Over Varying Flowrates | | | |
| IX | 98.79 ± 0.58% | 98.16 ± 0.06% | 97.23 ± 0.29% | 87.79 ± 17.88% |
| 14-A | 90.76 ± 19.98% | 49.66 ± 32.76% | 48.21 ± 27.70% | 36.73 ± 20.74% |

Table 44 illustrates the superior aerosol properties of Formulation IX over Formulation 14-A. The Dv(50)-from-DPI Ratio at 15 LPM/60 LPM for Formulation IX vs. 14-A was 1.77 and 13.85, respectively. The CEPM Ratio at 60 LPM/15 LPM for Formulation IX vs. 14-A was 1.13 and 2.47, respectively.

TABLE 44

Dv(50)-from-DPI Ratio and CEPM Ratio

| Formulation | Dv(50)-from-DPI Ratio 15 LPM/60 LPM | Dv(50)-from-DPI Ratio 20 LPM/60 LPM | CEPM Ratio 60 LPM/15 LPM | CEPM Ratio 60 LPM/20 LPM |
|---|---|---|---|---|
| IX | 1.77 | 1.41 | 1.13 | 1.02 |
| 14-A | 13.85 | 8.58 | 2.47 | 1.88 |

Example 15. Rotating Vacuum Dosator Filling of Powder Formulations at Low Fill Weights Formulation VI (75% calcium lactate, 20% leucine, 5% sodium chloride) and Formulation IX (82.0% levofloxacin, 11.7% leucine and 6.3% sodium chloride) were filled into receptacles using a rotating drum vacuum dosator (Omnidose TT, Harro Hofliger, Germany) capsule filler and demonstrated good powder flow characteristics as measured by the ability to fill a low average fill weight with a low relative standard deviation. In the Omnidose TT, powder is placed in a reservoir above a rotating drum so that when vacuum pressure is applied to the drum, a dose of powder from the reservoir is drawn into a small, fixed volume, precision manufactured dosing bore in the drum. The drum is then rotated about 180 degrees and a positive air pressure is applied to the drum to discharge the powder dose into a receptacle held below the drum. For each powder formulation, the Omnidose TT was configured with a dosing bore in the dosing drum that had a volume of 1.43 cubic millimeters with an applied vacuum pressure of −600 mbar. Both powders were dosed with a single actuation into stainless steel receptacles which were weighed gravimetrically before and after dosing to determine individual sample fill weights. For Formulation VI, 19 samples were filled and for Formulation IX, 20 samples were filled. As can be seen from Table 45, Formulation VI had an average fill weight of 0.840 mg with a relative standard deviation (RSD) of 1.45% while similarly Formulation IX had an average fill weight of 0.838 mg with a relative standard deviation (RSD) of 1.64%. These results are significant because they demonstrate that powder fill weights of less than 1 mg are achievable for inhalable powders without the need for large particle carriers such as lactose, compared to standard industry practice of filling greater than 5 mg of powder. In addition, the ability to fill less than 1 mg of powder consistently, as demonstrated by RSD values below typical industry requirements of 3%, with very high pharmaceutical ingredient contents (>70% by weight for both levofloxacin and calcium lactate) and relatively high powder density allows for more much smaller dosage units in dry powder inhalers than would typically be required for either carrier particle blended formulations or large porous particle formulations.

TABLE 45

Rotating vacuum dosator filling of powder formulations at low fill weight

| | Formulation VI | Formulation IX |
|---|---|---|
| Batch Size (n) | 19 | 20 |
| Mean fill weight (mg) | 0.840 mg | 0.838 mg |
| Standard Deviation (mg) | 0.012 mg | 0.014 mg |
| Relative Standard Deviation; RSD (%) | 1.45% | 1.64% |
| Filled powder density (g/mL) | 0.59 g/mL | 0.59 g/mL |

Example 16. Preferred Formulations of
Levofloxacin and their Powder Properties

Table 46 lists some preferred dry powder formulations of levofloxacin. One common feature to these formulations is that they each contain a relatively high percentage by weight of levofloxacin in the formulation, ranging from 55% to 70%, on a dry weight basis. This is an important characteristic because an effective dose of antibiotics such as levofloxacin to the respiratory tract requires tens to hundreds of milligrams. Typically, delivering this quantity of active agent requires multiple unit doses of dry powder, such as multiple capsules, which can lead to poor patient compliance. One way to minimize to total mass and volume of powder that needs to be inhaled is to increase the levofloxacin loading in the formulation.

TABLE 46

Feedstock compositions of levofloxacin magnesium lactate and various excipients

| Formulation | Salt | Salt % | Excipient | Excipient load (w/w) | Therapeutic | Therapeutic load (w/w) |
|---|---|---|---|---|---|---|
| XIX | Magnesium Lactate | 25 | Leucine | 5 | Levofloxacin | 70 |
| XX | Magnesium Lactate | 25 | Maltodextran | 5 | Levofloxacin | 70 |
| XXI | Magnesium Lactate | 25 | N/A | N/A | Levofloxacin | 75 |
| XXII | Magnesium Lactate | 25 | Maltodextran | 20 | Levofloxacin | 55 |
| XXIII | Magnesium Lactate | 10 | Maltodextran | 35 | Levofloxacin | 55 |

Table 47 reports formulations of levofloxacin, sodium chloride and leucine in varying percentages of each. Another way to minimize the number of unit doses of dry powder that need to be administered is to increase the tapped density. Increased tap density leads to less overall filled powder volume needed, and thereby fewer unit doses needed. The maximum tapped density is seen for the 50% and 60% levofloxacin powders with values of 0.93 and 0.92 g/cc, respectively. Values of between 0.63 and 0.8 g/cc are seen for the other powders with levofloxacin loading between 20% and 90%. A challenge faced by these formulations is that as the levofloxacin loading increases the FPF_TD<5.6 microns decreases from 85.6% at 0% levofloxacin loading to 39.3% at one specific 80% levofloxacin formulation. The CEPM stays pretty constant across formulations, even at 15 LPM indicating good dose emission from the capsule, until the 90% levofloxacin formulation where the CEPM values drop considerably. The Dv50 at 60 LPM stays relatively constant from 20% to 70% levofloxacin, and then increases slightly for the 80% and 90% levofloxacin formulations.

TABLE 47

| | Levofloxacin loading range | | | | | | |
|---|---|---|---|---|---|---|---|
| Ratios (leucine/NaCl/ levofloxacin) | Yield (%) | FPF_TD <5.6 μm (%) | CEPM at 60 LPM | CEPM at 15 LPM | Dv50 (microns) At 60 LPM | Dv50 (microns) At 15 LPM | Tapped density (g/cc) |
| 35.6:64.4:0.0 | 39.2 | 85.6 | 100% | 89% | 1.4 | 4.8 | N/A |
| 30.0:60.0:10.0 | 66.4 | 80.6 | 100% | 82% | 1.11 | 3.58 | 0.54 |
| 27.0:53.0:20.0 | 82.4 | 68.8 | 100% | 79% | 1.33 | 2.89 | 0.8 |
| 16.0:34.0:50.0 | 85.3 | 59.3 | 100%, | 98%, | 1.61 | 2.55 | 0.93 |
| 13.0:27.0:60.0 | 72.3 | 57.5 | 98% | 96% | 1.89 | 2.34 | 0.92 |
| 10.0:20.0:70.0 | 74.1 | 46.2 | 98% | 94% | 1.68 | 2.46 | 0.79 |
| 7.0:13.0:80.0 | 71.9 | 48.8 | 98% | 84% | 2.22 | 2.78 | 0.72 |
| 3.0:7.0:90.0 | 71.5 | 55.6 | 97% | 13% | 1.82 | 4.32 | 0.62 |
| 13.0:7.0:80.0 | 66.7 | 39.3 | 99% | 86% | 2.77 | 4.26 | 0.72 |
| 7.0:3.0:90.0 | 68.3 | 51.7 | 98% | 34% | 2.08 | 3.92 | 0.63 |

Table 48 reports multiple formulation of levofloxacin with 80% or greater loading, with sodium chloride and leucine making up the rest of the formulation. The yield, FPF_TD<5.6 microns, CEPM and Dv50 at 60 LPM and bulk and tapped density seemed relatively unaffected by the change in formulation. However the CEPM and Dv50 at 30 LPM showed a marked decrease in CEPM and increase in Dv50 for the 100% levofloxacin formulation, and the deviation was accentuated even more at the 15 LPM values for both CEPM and Dv50, indicating poor dose emission and deagglomeration of the formulation at lower inhalation flow rates. Multiple formulations dropped in CEPM at 15 LPM, possibly showing that this 15 LPM is at the edge of dispersibility for these powders, however for all formulations except for the 100% levofloxacin, the Dv50 of the powder that did emit remained below 5 micrometers, indicating that the powder which was emitted was sufficiently deagglomerated.

TABLE 48

Exemplary high load levofloxacin powders

| Ratios (leucine/NaCl/ levofloxacin) | Yield (%) | FPF_TD <5.6 μm (%) | CEPM, Dv50 at 60 LPM | CEPM, Dv50 at 30 LPM | CEPM, Dv50 at 15 LPM | Bulk density (g/cc) | Tapped density (g/cc) |
|---|---|---|---|---|---|---|---|
| 13.0:7.0:80.0 | 66.7 | 39.3 | 99%, 2.8 μm | 99%, 2.8 μm | 86%, 4.3 μm | 0.39 | 0.72 |
| 7.0:13.0:80.0 | 71.9 | 48.8 | 98%, 2.2 μm | 95%, 2.3 μm | 84%, 2.8 μm | 0.45 | 0.72 |
| 11.7:6.3:82.0 | 80.4 | 55.2 | 99%, 2.8 μm | 99%, 2.7 μm | 95%, 3.7 μm | 0.36 | 0.73 |
| 9.0:9.0:82.0 | 77 | 56.1 | 98%, 1.8 μm | 91%, 2.0 μm | 36%, 3.0 μm | 0.47 | 0.72 |
| 6.3:11.7:82.0 | 76.3 | 54.5 | 98%, 1.6 μm | 95%, 2.0 μm | 29%, 2.8 μm | 0.45 | 0.65 |
| 9.75:5.25:85.0 | 75.8 | 42 | 99%, 2.8 μm | 92%, 3.0 μm | 39%, 4.1 μm | 0.32 | 0.74 |
| 5.25:9.75:85.0 | 73.5 | 54.9 | 96%, 1.8 μm | 78%, 2.1 μm | 46%, 3.2 μm | 0.52 | 0.68 |
| 7.0:3.0:90.0 | 68.3 | 51.7 | 98%, 2.1 μm | 67%, 2.3 μm | 34%, 3.9 μm | 0.35 | 0.63 |
| 3.0:7.0:90.0 | 66.7 | 53.3 | 96%, 1.9 μm | 53%, 2.2 μm | 14%, 4.9 μm | 0.4 | 0.68 |
| 100% Levo | 58.9 | 33.5 | 91%, 5.0 μm | 50%, 12.2 μm | 37%, 68.7 μm | 0.31 | 0.6 |

Table 49 reports dry powder and aerosol performance properties for multiple formulations of 75% levofloxacin and 25% of various monovalent and divalent metal cation salts. Formulations that performed well across all parameters including a CEPM at 20 LPM of 75% or greater and FPF_TD<5.6 of 40% or greater were sodium chloride calcium lactate, magnesium lactate, sodium sulfate, sodium citrate, potassium chloride, and calcium acetate.

TABLE 49

Characteristics of exemplary levo powders

| Formulation | Formulation (ratio: 75:25) | Yield (%) | HELOS/ RODOS: 1 bar (microns) | HELOS/ RODOS: 4 bar (microns) | FPF_TD <5.6 microns | CEPM % at 60 LPM | CEPM % at 20 LPM | Spraytec Dv50 at 60 LPM (microns) | Spraytec Dv50 at 20 LPM (microns) | Tap density (g/cc) |
|---|---|---|---|---|---|---|---|---|---|---|
| XXXII | Levo:NaCl | 69.5 | 1.89 | 1.62 | 57.22 | 98% | 95% | 1.84 | 2.56 | 0.86 |
| XXXIII | Levo:CaLac | 70.6 | 1.9 | 1.77 | 53.57 | 94% | 76% | 2.24 | 3.18 | 0.88 |
| XXI | Levo:MgLac | 70.8 | 2.03 | 2.04 | 43.12 | 90% | 76% | 2.42 | 2.77 | 0.92 |
| XXVIII | Levo:NaSO4 | 55.8 | 1.75 | 1.63 | 47.57 | 95% | 90% | 1.92 | 4.43 | 0.79 |
| XXXIV | Levo:Mg Citrate | 64.7 | 2.12 | 1.96 | 48.2 | 93% | 60% | 2.44 | 2.9 | 0.72 |
| XXXV | Levo:MgSO4 | 79.2 | 1.88 | 1.85 | 34.45 | 80% | 61% | 2.44 | 3.04 | 0.68 |
| XXIX | Levo:Na Citrate | 48.4 | 1.62 | 1.55 | 54.25 | 92% | 81% | 1.72 | 2.27 | 0.63 |

TABLE 49-continued

Characteristics of exemplary levo powders

| Formulation | Formulation (ratio: 75:25) | Yield (%) | HELOS/ RODOS: 1 bar (microns) | HELOS/ RODOS: 4 bar (microns) | FPF_TD <5.6 microns | CEPM % at 60 LPM | CEPM % at 20 LPM | Spraytec Dv50 at 60 LPM (microns) | Spraytec Dv50 at 20 LPM (microns) | Tap density (g/cc) |
|---|---|---|---|---|---|---|---|---|---|---|
| XXXVI | Levo: MgCl2 | 81.6 | 2.18 | 1.89 | 36.08 | 86% | 53% | 2.51 | 3.26 | 0.75 |
| XXXVII | Levo: CaCl2 | 83.4 | 2 | 1.86 | 40.34 | 85% | 33% | 2.28 | 3.57 | 0.8 |
| XXXI | Levo: KCL | 78.5 | 1.63 | 1.78 | 44.08 | 97% | 92% | 1.81 | 2.72 | 0.79 |
| XXX | Levo:Ca Acetate | 44.9 | 2.23 | 1.97 | 46.96 | 95% | 75% | 2.42 | 2.63 | 0.74 |

Table 50 reports differential scanning calorimetry (DSC) results for 75% levofloxacin and 25% of various monovalent and divalent metal cation salts. DSC was performed using a TA Instruments differential scanning calorimeter Q2000 (New Castle, Del.). The samples were placed into a hermetically sealed aluminum DSC pan, and the weight accurately recorded. The following method was employed: Conventional MDSC, Equilibrate at 0.00° C., Modulate±1.00° C. every 60 s, Isothermal for 5.00 min, Ramp 2.00° C./min to target temperature. Indium metal was used as the calibration standard. The glass transition temperature (Tg) is reported from the inflection point of the transition or the half-height of the transition. The Tg indicates the glass transition temperature which is defined as the reversible transition in amorphous materials from a hard and relatively brittle state into a molten or rubber-like state. The crystallization temperature (Tc) is reported from the onset of crystallization. The Tc indicates the crystallization temperature which is defined as the transition from the amorphous to the crystalline state.

A Tg of about 50 degrees celcius above the storage conditions of 25 degrees celcius is preferred in order for the dry powder to stay in the amorphous phase. The levofloxacin formulations with calcium lactate, magnesium citrate, magnesium lactate and magnesium sulfate all had a Tg in excess of 75 degrees celcius. The formulation containing sodium chloride having a Tc of 63 degrees celcius is also acceptable because the dry powder converted to a crystalline phase in a way that the powder's aerosol properties were maintained.

TABLE 50

Contrasting Tg for Various Levofloxacin Formulations

| Formulation | Formulation (ratio: 75:25) | Tg ° C. (inflection) | Tc ° C. (onset) |
|---|---|---|---|
| XXXIII | Levo:Ca Lactate | 85.3 | 97.2 |
| XXXIV | Levo:Mg Citrate | 140.1 | ND |
| XXIX | Levo:Na Citrate | 68.5 | 81.5 |
| XXVIII | Levo:Na Sulfate | 67.5 | 78.9 |
| XXXII | Levo:NaCl | ND | 63 |
| XXI | Levo:Mg Lactate | 107.1 | 111.5 |
| XXXV | Levo:Mg Sulfate | 79.5 | 107.3 |

ND = non-detectable

Figures 7A, 7B:
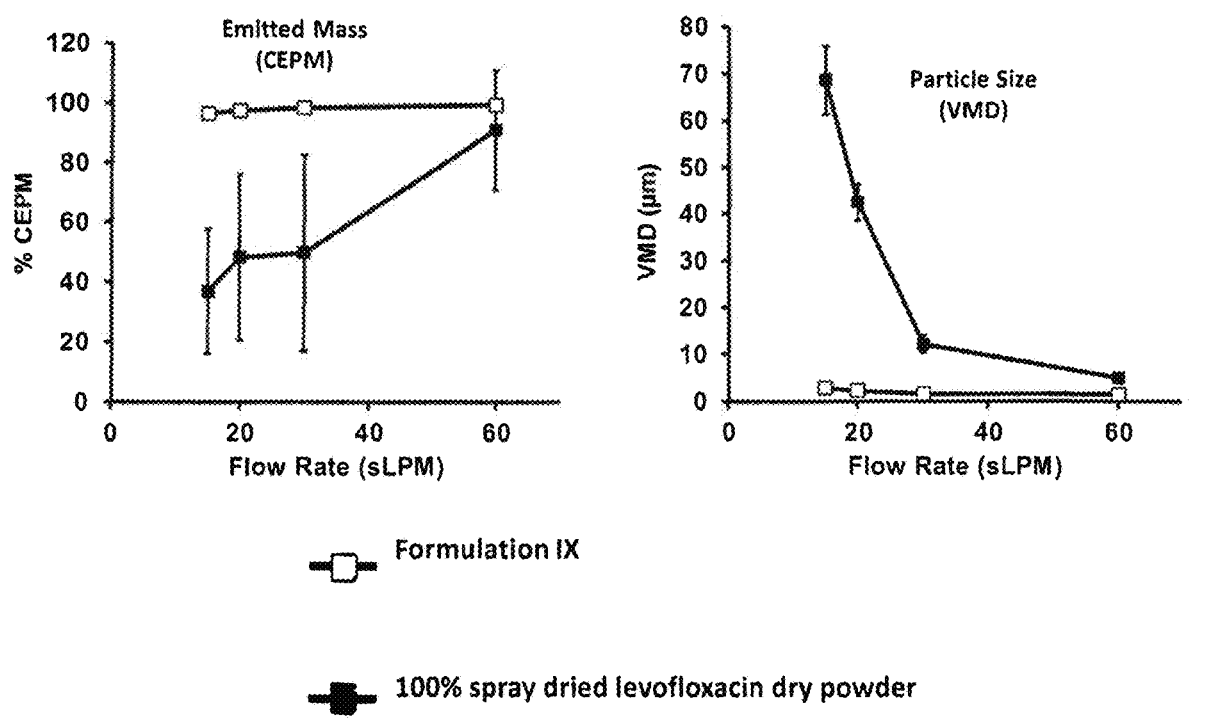

FIG. 7A shows a plot of CEPM and FIG. 7B shows a plot of volume median diameter (VMD; same as Dv50) for Formulation IX and 100% levofloxacin over a range of flowrates from 60 LPM to 15 LPM emitted from a high resistance RS-01 dry powder inhaler. The data show that the CEPM of Formulation IX stays nearly constant around 100% over the full range of flowrates, while the 100% levofloxacin formulation dropped to about 50% CEPM even at 30 LPM. The data show that the Dv50 of Formulation IX stays nearly constant well below about 5 microns, while the 100% levofloxacin rises to about 10 microns at 30 LPM and then to about 40 microns and about 70 microns at 20 and 15 LPM, respectively. This data show that the presence of the sodium chloride and leucine in the levofloxacin Formulation IX plays an important role in making these formulations relatively independent of a patient's inspiratory flowrate and able to emit and deagglomerate the particle even at very low inhalation flow rates.

Figure 8A:
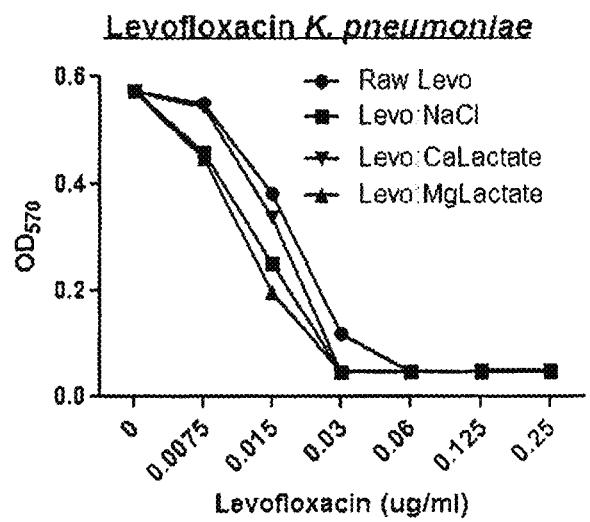
FIG. 8A and FIG. 8B are graphs showing results for Minimum Inhibitory Concentration (MIC) assays of levofloxacin-containing dry powder formulations in *S. pneumoniae* (8A) and *K. pneumoniae* (8B).
Figure 8B:
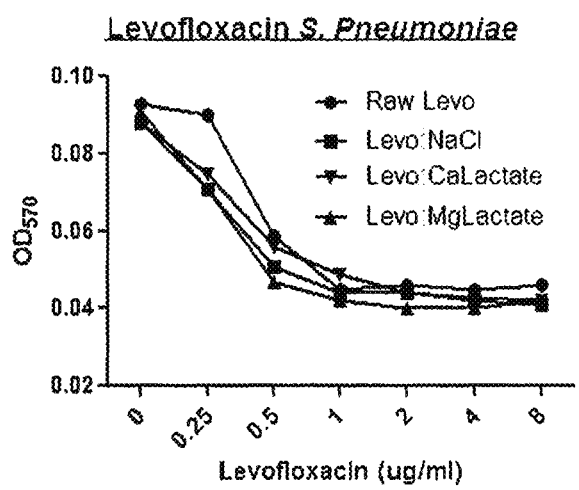

Example 17. In Vitro and In Vivo Examples of Some Preferred Formulations of Levofloxacin Example 17A. Levofloxacin-Containing Dry Powder Formulations Formulation XXXII, Formulation XXXIII, and Formulation XXI Exhibit Antibacterial Activity In Vitro The antibacterial activity of levofloxacin-containing dry powder formulations Formulation XXXII ("Levo:NaCl", 75:25 (% w/w)), Formulation XXXIII ("Levo:CaLactate", 75:25 (% w/w)), and Formulation XXI ("Levo:MgLactate", 75:25 (% w/w)) was tested in a MIC (minimum-inhibitory concentration) assay with two bacterial strains, Klebsiella pneumoniae and Streptococcus pneumoniae. 100% levofloxacin powder as provided by the manufacturer ("raw Levo") served as a positive control. S. pneumoniae and (K. pneumoniae) were grown overnight, harvested, and brought to 1×10$^6$ CFU/ml in Mueller-Hinton Broth (MHB). Bacteria were exposed to a range of both antibiotic and dry powder formulation concentrations, and incubated overnight at 37° C., ±5% $CO_2$. Dilutions of levofloxacin and respective dry powder formulations were prepared in MHB, and bacteria was exposed to 50 microliter of an increasing concentration gradient of levofloxacin or levofloxacin/metal cation salt. Antibiotic load was matched between 100% levofloxacin dry powder and the dry powder formulations Formulation XXXII, Formulation XXXIII, and Formulation XXI. Growth (bacteria only) and sterility (MHB only) controls were also included for comparison. Following 16-20 h incubation, wells were read at $OD_{570}$. Results are shown in FIG. 8A and FIG. 8B (FIG. 8A: K. pneumonia, FIG. 8B: S. pneumonia). MIC values were evaluated and defined as $OD_{570}$ values at or close to the sterility controls. These data demonstrate that the dry powder formulations Formulation XXXII, Formulation XXXIII, and Formulation XXI exhibit antimicrobial activity similar to that of 100% levofloxacin.

Figure 9:
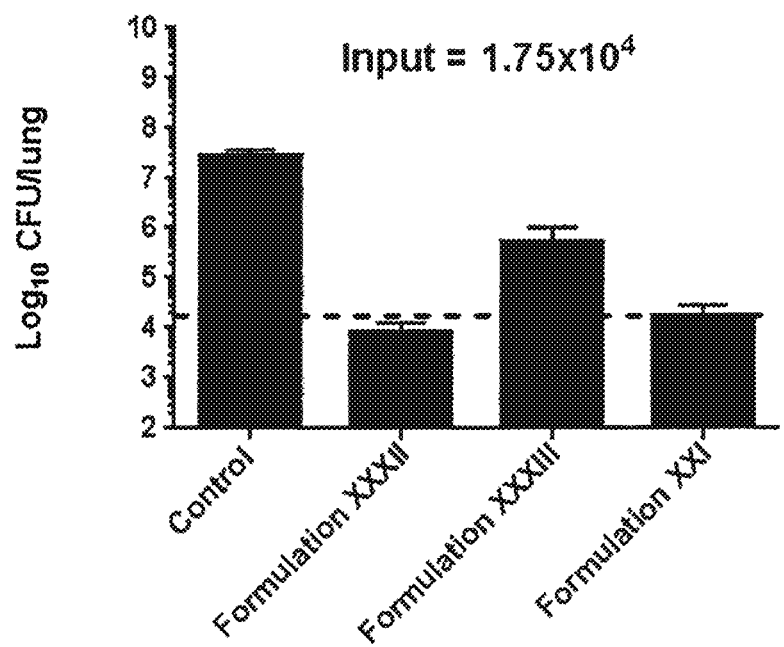
FIG. 9 is a bar graph showing results for CFU/lung homogenate following infection by *K. pneumoniae* and treatment with multiple levofloxacin-containing dry powder formulations.

Example 17B. Levofloxacin-Containing Dry Powder Formulations Formulation XXXII, Formulation XXXIII, and Formulation XXI Exhibit Antibacterial Activity In Vivo The antibacterial activity of levofloxacin-containing dry powder formulations Formulation XXXII ("Levo:NaCl", 75:25 (% w/w)), Formulation XXXIII ("Levo:CalLactate", 75:25 (% w/w)), and Formulation XXI ("Levo:MagLactate", 75:25 (% w/w)) was tested in a mouse model. Mice were infected with 1×10$^4$ CFU/mouse *Klebsiella pneumoniae* IN on Day 0. On Day 2, mice were administered dry powder treatments b.i.d. via whole body exposure of 1.5 mg/kg levofloxacin with Formulation XXXII, Formulation XXXIII, and Formulation XXI. A leucine placebo powder was included for comparison. Lung homogenates were collected on Day 3 for analysis of bacterial load by CFU. Data in FIG. 9 demonstrate that all three levofloxacin-containing dry powder formulations are effective at reducing bacterial load in the lungs of mice following infection by *K. pneumoniae*.

The invention claimed is:

1. A process for producing one or more receptacles with a respirable dry powder disposed therein, comprising
   disposing the respirable dry powder into a plurality of said receptacles at a target fill weight and at a rate of about one receptacle every 4 seconds or less to produce filled receptacles, wherein at least 80% of said filled receptacles contain said respirable dry powder within 85% to 115% of the target fill weight; and
   wherein the respirable dry powder consists of respirable dry particles that have a volume median geometric diameter (VMGD) of about 10 micrometers or less, and a tap density of at least about 0.45 g/cubic centimeters, and wherein the respirable dry particles comprise a sodium salt and an anti-fungal agent that provides at least about 25% of the total mass of the contents disposed within the one or more receptacles, with the proviso that the respirable dry particles do not contain a divalent metal cation salt.

2. The process of claim 1, wherein the respirable dry powder is filled into a plurality of said receptacles at a target fill weight and at a rate of about one receptacle every 1 second or less to produce filled receptacles, wherein at least 80% of said filled receptacles contain said respirable dry powder within 85% to 115% of the target fill weight.

3. The process of claim 1, further comprising sealing the one or more receptacles.

4. The process of claim 1, wherein the sodium salt is at least about 3% by weight of the respirable dry particles.

5. The process of claim 1, wherein the sodium salt is selected from the group consisting of sodium chloride, sodium citrate, sodium sulfate, sodium lactate, sodium acetate, sodium bicarbonate, sodium carbonate, sodium stearate, sodium ascorbate, sodium benzoate, sodium biphosphate, dibasic sodium phosphate, sodium bisulfate, sodium borate, sodium gluconate, sodium metasilicate, and sodium propionate.

6. The process of claim 1, wherein said disposing the respirable dry powder into a plurality of said receptacles is performed with a vacuum dosator.

7. The process of claim 1, wherein said vacuum dosator is a rotating drum vacuum dosator.

8. A process for producing one or more receptacles with a respirable dry powder disposed therein, comprising
   disposing the respirable dry powder into a plurality of said receptacles at a target fill weight and at a rate of about one receptacle every 4 seconds or less to produce filled receptacles, wherein at least 80% of said filled receptacles contain said respirable dry powder within 85% to 115% of the target fill weight; and
   wherein the respirable dry powder consists of respirable dry particles that have a volume median geometric diameter (VMGD) of about 10 micrometers or less, and a tap density of at least about 0.45 g/cubic centimeters, and wherein the respirable dry particles comprise a sodium salt and itraconazole that provides at least about 25% of the total mass of the contents disposed within the one or more receptacles, with the proviso that the respirable dry particles do not contain a divalent metal cation salt.

9. The process of claim 8, wherein the respirable dry powder is filled into a plurality of said receptacles at a target fill weight and at a rate of about one receptacle every 1 second or less to produce filled receptacles, wherein at least 80% of said filled receptacles contain said respirable dry powder within 85% to 115% of the target fill weight.

10. The process of claim 8, further comprising sealing the one or more receptacles.

11. The process of claim 8, wherein the sodium salt is at least about 3% by weight of the respirable dry particles.

12. The process of claim 8, wherein the sodium salt is selected from the group consisting of sodium chloride, sodium citrate, sodium sulfate, sodium lactate, sodium acetate, sodium bicarbonate, sodium carbonate, sodium stearate, sodium ascorbate, sodium benzoate, sodium biphosphate, dibasic sodium phosphate, sodium bisulfate, sodium borate, sodium gluconate, sodium metasilicate, and sodium propionate.

13. The process of claim 8, wherein said disposing the respirable dry powder into a plurality of said receptacles is performed with a vacuum dosator.

14. The process of claim 13, wherein said vacuum dosator is a rotating drum vacuum dosator.

* * * * *